(12) United States Patent
Rajashekara et al.

(10) Patent No.: US 11,660,294 B2
(45) Date of Patent: May 30, 2023

(54) COMPOUNDS, COMPOSITIONS, AND METHODS FOR THE TREATMENT AND PREVENTION OF AVIAN PATHOGENIC E. COLI (APEC)

(71) Applicant: Ohio State Innovation Foundation, Columbus, OH (US)

(72) Inventors: Gireesh Rajashekara, Wooster, OH (US); Dipak Kathayat, Wooster, OH (US); Yosra A. Helmy, Wooster, OH (US); Loïc Deblais, Wooster, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 162 days.

(21) Appl. No.: 17/260,140

(22) PCT Filed: Jul. 15, 2019

(86) PCT No.: PCT/US2019/041876
§ 371 (c)(1),
(2) Date: Jan. 13, 2021

(87) PCT Pub. No.: WO2020/014709
PCT Pub. Date: Jan. 16, 2020

(65) Prior Publication Data
US 2021/0330655 A1  Oct. 28, 2021

Related U.S. Application Data

(60) Provisional application No. 62/697,876, filed on Jul. 13, 2018.

(51) Int. Cl.
| | |
|---|---|
| *A61K 31/445* | (2006.01) |
| *A23K 20/132* | (2016.01) |
| *A23K 20/137* | (2016.01) |
| *A23K 20/195* | (2016.01) |
| *A23K 50/75* | (2016.01) |
| *A23K 20/111* | (2016.01) |
| *A61P 31/04* | (2006.01) |
| *A01N 37/18* | (2006.01) |
| *A01N 37/42* | (2006.01) |
| *A01N 41/10* | (2006.01) |
| *A01N 43/36* | (2006.01) |
| *A01N 43/40* | (2006.01) |
| *A01N 43/42* | (2006.01) |
| *A01N 43/60* | (2006.01) |
| *A01N 43/78* | (2006.01) |
| *A01N 43/82* | (2006.01) |
| *A01N 47/48* | (2006.01) |
| *A01N 43/50* | (2006.01) |
| *A01N 43/52* | (2006.01) |
| *A61K 9/00* | (2006.01) |
| *A61K 31/10* | (2006.01) |
| *A61K 31/166* | (2006.01) |
| *A61K 31/216* | (2006.01) |
| *A61K 31/325* | (2006.01) |
| *A61K 31/40* | (2006.01) |
| *A61K 31/4164* | (2006.01) |
| *A61K 31/4184* | (2006.01) |
| *A61K 31/427* | (2006.01) |
| *A61K 31/4525* | (2006.01) |

(Continued)

(52) U.S. Cl.
CPC ......... *A61K 31/445* (2013.01); *A01N 37/18* (2013.01); *A01N 37/42* (2013.01); *A01N 41/10* (2013.01); *A01N 43/36* (2013.01); *A01N 43/40* (2013.01); *A01N 43/42* (2013.01); *A01N 43/50* (2013.01); *A01N 43/52* (2013.01); *A01N 43/60* (2013.01); *A01N 43/78* (2013.01); *A01N 43/82* (2013.01); *A01N 47/48* (2013.01); *A23K 20/111* (2016.05); *A23K 20/132* (2016.05); *A23K 20/137* (2016.05); *A23K 20/195* (2016.05); *A23K 50/75* (2016.05); *A61K 9/0056* (2013.01); *A61K 31/10* (2013.01); *A61K 31/166* (2013.01); *A61K 31/216* (2013.01); *A61K 31/325* (2013.01); *A61K 31/40* (2013.01); *A61K 31/4164* (2013.01); *A61K 31/4184* (2013.01); *A61K 31/427* (2013.01); *A61K 31/4525* (2013.01); *A61K 31/4545* (2013.01); *A61K 31/47* (2013.01); *A61K 31/495* (2013.01); *A61K 31/496* (2013.01); *A61K 31/551* (2013.01); *A61K 45/06* (2013.01); *A61P 31/04* (2018.01)

(58) Field of Classification Search
None
See application file for complete search history.

(56) References Cited

U.S. PATENT DOCUMENTS

| 7,495,027 B2 * | 2/2009 | Caufield ............... A61P 31/04 |
| | | 514/474 |
| 9,961,886 B2 * | 5/2018 | Ala'Aldeen ......... A61K 31/555 |

(Continued)

FOREIGN PATENT DOCUMENTS

WO  2018/035183 A1  2/2018

OTHER PUBLICATIONS

De Waelheyns et al., "Identification of small-molecule inhibitors against SecA by structure-based virtual ligand screening", 2015, The Journal of Antibiotics, 68(11), pp. 666-673. (doi:10.1038/ja.2015.53) (Year: 2015).*

(Continued)

*Primary Examiner* — My-Chau T. Tran
(74) *Attorney, Agent, or Firm* — Meunier Carlin & Curfman LLC

(57) ABSTRACT

Disclosed are anti-avian pathogenic *E. coli* (APEC) agents as well as methods of using thereof.

21 Claims, 31 Drawing Sheets
Specification includes a Sequence Listing.

(51) Int. Cl.

| | |
|---|---|
| A61K 31/4545 | (2006.01) |
| A61K 31/47 | (2006.01) |
| A61K 31/495 | (2006.01) |
| A61K 31/496 | (2006.01) |
| A61K 31/551 | (2006.01) |
| A61K 45/06 | (2006.01) |

(56) References Cited

U.S. PATENT DOCUMENTS

| | | | |
|---|---|---|---|
| 11,046,668 B2* | 6/2021 | Rajashekara | A01N 43/10 |
| 11,419,335 B2* | 8/2022 | Huigens, III | A01N 43/50 |
| 11,478,454 B2* | 10/2022 | Rajashekara | A01N 43/50 |

OTHER PUBLICATIONS

Kathayat et al., "Small Molecule Adjuvants Potentiate Colistin Activity and Attenuate Resistance Development in *Escherichia coli* by Affecting pmrAB System", 2020, Infection and Drug Resistance, vol. 13, pp. 2205-2222 (Year: 2020).*

Kathayat et al., "Novel Small Molecule Growth Inhibitor Affecting Bacterial Outer Membrane Reduces Extraintestinal Pathogenic *Escherichia coli* (ExPEC) Infection in Avian Model", 2021, Microbiol. Spectr., 9(2), pp. 1-23. (Year: 2021).*

International Search Report and Written Opinion issued by the International Searching Authority (ISA/US) in PCT Application No. PCT/US2019/041876 dated Nov. 21, 2019. 15 pages.

Dheilly, Alexandra, et al. "Antimicrobial resistance selection in avian pathogenic *E. coli* during treatment." Veterinary microbiology 166.3-4 (2013): 655-658. Abstract only.

Pubchem, Substance Record for 366767505. 2-(4-methoxyphenyl)-N-[(1-methyl-4-piperidinyl)methyl]-N-(4-pyridinylmethyl)ethanamine. Available May 25, 2018. https://pubchem.ncbi.nlm.nih.gov/substance/366767505#section=2D-Structure. 4 pages.

International Preliminary Report on Patentability issued for Application No. PCT/US2019/041876, dated Jan. 28, 2021.

Gyles, C. L. (2008). Antimicrobial resistance in selected bacteria from poultry. Animal Health Research Reviews, 9(02), 149-158. doi: 10.1017/s1466252308001552 10.1017/s1466252308001552.

Wilen, S. H., Collet, A., & Jacques, J. (1977). Strategies in optical resolutions. Tetrahedron, 33(21), 2725-2736. doi: 10.1016/0040-4020(77)80264-0 10.1016/0040-4020(77)80264-0.

Wallace, et al., Compound prioritization methods increase rates of chemical probe discovery in model organisms, 2011, 1273-83.

Kathayat, Dipak, et al. "Novel small molecules affecting cell membrane as potential therapeutics for avian pathogenic *Escherichia coli*." Scientific reports 8.1 (2018): 1-16.

Helmy, Yosra A., et al. Novel small molecule modulators of quorum sensing in avian pathogenic *Escherichia coli* (APEC). Virulence 9.1 (2018): 1640-1657.

Antao EM, Glodde S, Li G, Sharifi R, Homeier T, Laturnus C, Diehl I, Bethe A, Philipp HC, Preisinger R et al.: The chicken as a natural model for extraintestinal infections caused by avian pathogenic *Escherichia coli* (APEC). Microb Pathog 2008, 45(5-6):361-369.

Fantinatti F, Silveira WD, Castro AFP: Characteristics associated with pathogenicity of avian septicaemic *Escherichia coli* strains. Veterinary Microbiology 1994, 41(1-2):75-86.

Dziva F., Deciphering the infection biology of avian pathogenic *Escherichia coli*: role of experimental infection models. Current Research, Technology and Educational Topics in Applied Microbiology and Microbial Biotechnology, Series No. 2010, 2:746-753. Abstract.

Bumstead N, Huggins MB, Cook JKA: Genetic differences in susceptibility to a mixture of avian infectious bronchitis virus and *Escherichia coli*. British Poultry Science 1989, 30(1):39-48.

Vermeulen B, De Backer P, Remon JP: Drug administration to poultry. Advanced drug delivery reviews 2002, 54(6):795-803.

Wang S, Niu C, Shi Z, Xia Y, Yaqoob M, Dai J, et al. Effects of ibeA deletion on virulence and biofilm formation of avian pathogenic *Escherichia coli*. Infection and immunity 2011; 79:279-87.

Han X, Bai H, Liu L, Dong H, Liu R, Song J, et al. The luxS gene functions in the pathogenesis of avian pathogenic *Escherichia coli*. Microbial pathogenesis 2013; 55:21-7.

Barnes HJ, Nolan LK, Vaillancourt JF. Colibacillosis. In: Saif, Y.M., Fadly, A.M., Glisson, J.R., McDougald, L.R., Nolan, L.K., Swayne, D.E. (Eds.), Diseases of Poultry. 2008; 12th ed. Blackwell Publishing, Ames:691-732.

Zhao S, Maurer JJ, Hubert S, De Villena JF, McDermott PF, Meng J, et al. Antimicrobial susceptibility and molecular characterization of avian pathogenic *Escherichia coli* isolates. Veterinary Microbiology 2005; 107:215-24.

Guabiraba R, Schouler C. Avian colibacillosis: still many black holes. FEMS Microbiology Letters 2015; 362.

Ghunaim H, Abu-Madi MA, Kariyawasam S. Advances in vaccination against avian pathogenic *Escherichia coli* respiratory disease: potentials and limitations. Veterinary microbiology 2014; 172:13-22.

Hong-Geller E, Micheva-Viteva S. 2013. Small Molecule Screens to Identify Inhibitors of Infectious Disease doi:40447.

De La Fuente R, Sonawane ND, Arumainayagam D, Verkman AS. 2006. Small molecules with antimicrobial activity against *E. coli* and *P. aeruginosa* identified by high-throughput screening. British Journal of Pharmacology 149:551-559.

Selin C, Stietz MS, Blanchard JE, Gehrke SS, Bernard S, Hall DG, Brown ED, Cardona ST. 2015. A Pipeline for Screening Small Molecules with Growth Inhibitory Activity against Burkholderia cenocepacia. PLOS ONE 10:e0128587.

Olson PD, Kuechenmeister LJ, Anderson KL, Daily S, Beenken KE, Roux CM, Reniere ML, Lewis TL, Weiss WJ, Pulse M, Nguyen P, Simecka JW, Morrison JM, Sayood K, Asojo OA, Smeltzer MS, Skaar EP, Dunman PM. 2011. Small Molecule Inhibitors of *Staphylococcus aureus* RnpA Alter Cellular mRNA Turnover, Exhibit Antimicrobial Activity, and Attenuate Pathogenesis. PLOS Pathogens 7:e1001287.

Kumar A, Drozd M, Pina-Mimbela R, Xu X, Helmy YA, Antwi J, Fuchs JR, Nislow C, Templeton J, Blackall PJ, Rajashekara G. 2016. Novel Anti-Campylobacter Compounds Identified Using High Throughput Screening of a Pre-selected Enriched Small Molecules Library. Frontiers in Microbiology 7:405.

Johnson JG, Yuhas C, McQuade TJ, Larsen MJ, DiRita VJ. 2015. Narrow-Spectrum Inhibitors of Campylobacter jejuni Flagellar Expression and Growth. Antimicrobial Agents and Chemotherapy 59:3880-3886.

Godbole AA, Ahmed W, Bhat RS, Bradley EK, Ekins S, Nagaraja V. 2015. Targeting *Mycobacterium tuberculosis* Topoisomerase I by Small-Molecule Inhibitors. Antimicrobial Agents and Chemotherapy 59:1549-1557.

Sandhaus S, Annamalai T, Welmaker G, Houghten RA, Paz C, Garcia PK, Andres A, Narula G, Rodrigues Felix C, Geden S, Netherton M, Gupta R, Rohde KH, Giulianotti MA, Tse-Dinh Y-C. 2016. Small-Molecule Inhibitors Targeting Topoisomerase I as Novel Antituberculosis Agents. Antimicrobial Agents and Chemotherapy 60:4028-4036.

Nair DR, Monteiro JM, Memmi G, Thanassi J, Pucci M, Schwartzman J, Pinho MG, Cheung AL. 2015. Characterization of a novel small molecule that potentiates beta-lactam activity against gram-positive and gram-negative pathogens. Antimicrob Agents Chemother 59:1876-85.

Tsai CJ, Loh JM, Proft T. 2016. Galleria mellonella infection models for the study of bacterial diseases and for antimicrobial drug testing. Virulence 7:214-29.

Potera C. 2010. Antibiotic Resistance: Biofilm Dispersing Agent Rejuvenates Older Antibiotics. Environmental Health Perspectives 118:A288-A288.

Shane, S.M. 2009. Reducing pathogenic *E. coli* infection by vaccination, http://www.worldpoultry.net/Broilers/Health/2009/12/Reducing-pathogenic-E-coli-infection-by-vaccination-WP006966W/, ed.

Mellata, M., Maddux, J. T., Nam, T., Thomson, N., Hauser, H., Stevens, M. P., . . . Curtiss, R. (2012). New Insights into the

(56) References Cited

OTHER PUBLICATIONS

Bacterial Fitness-Associated Mechanisms Revealed by the Characterization of Large Plasmids of an Avian Pathogenic *E. coli*. PLoS ONE, 7(1), e29481. doi:10.1371/journal.pone.0029481.

Dil N, Qureshi MA. 2002. Differential expression of inducible nitric oxide synthase is associated with differential Toll-like receptor-4 expression in chicken macrophages from different genetic backgrounds. Vet Immunol Immunopathol 84:191-207.

* cited by examiner (C)

SM1          SM2          SM3

SM4          SM5

SM6          SM7          SM8

SM9          SM10          SM11

B) THP-1

COMPOUNDS, COMPOSITIONS, AND METHODS FOR THE TREATMENT AND PREVENTION OF AVIAN PATHOGENIC E. COLI (APEC)

CROSS-REFERENCE TO RELATED APPLICATIONS

This application is a national stage application filed under 35 U.S.C. § 371 of PCT/US2019/041876 filed Jul. 15, 2019, which claims benefit of U.S. Provisional Application No. 62/697,876, filed Jul. 13, 2018, which is hereby incorporated herein by reference in its entirety.

STATEMENT REGARDING FEDERALLY SPONSORED RESEARCH OR DEVELOPMENT

This invention was made with Government Support under Grant No. 2015-68004-23131 awarded by the United States Department of Agriculture—National Institute of Food and Agriculture. The Government has certain rights in the invention.

BACKGROUND

*E. coli* is a gram-negative, rod-shaped bacterium that is commonly found in the lower intestine of warm-blooded organisms. Most *E. coli* strains are harmless. However, some strains are pathogenic and can cause serious illness in humans and other animals. Illnesses caused by pathogenic *E. coli* include, for example, gastrointestinal infections, skin infections, respiratory infections, urinary tract infections, neonatal meningitis, inflammation, septicemia, mastitis, colibacillosis, perihepatitis, pericarditis, and peritonitis.

In particular, avian pathogenic *E. coli* (APEC) is a group of *E. coli* strains that cause a variety of respiratory and skin diseases in chickens, turkeys, and other avian species. APEC are the most common bacterial pathogen in chickens, costing the poultry industry hundreds of millions of dollars in economic losses worldwide. The economic losses from colibacillosis, caused by APEC, arise from the increased mortality and decreased growth rate of the affected birds. For example, in Brazil, which is the world's largest exporter of chicken meat, APEC are responsible for 45.2% of condemned poultry carcasses.

In addition to the economic losses, APEC isolates are suspected to be a major source for spreading antimicrobial resistance to other human and animal pathogens, mainly through their plasmids and the exchange of genetic material with other bacteria. Even in countries and regions with strict limits on antibiotic use in the poultry industry, such as the U.S., Australia, and Europe, up to 92% of avian *E. coli* isolates are resistant to three or more antimicrobial drugs. See Gyles et al., *Anim. Health Res. Rev.*, 2008, 9:149-158, incorporated by reference in its entirety.

APEC is abundant on chicken farms, where the inhalation of dust particles loaded with bacteria is the main route of infection. The disease develops quickly, within 24-48 hours, and can only be cured though the use of antimicrobial drugs. However, increased use of antibiotics, due to APEC, has contributed to the emergence of antibiotic-resistant strains of pathogenic *E. coli*.

Accordingly, improved methods of treating and preventing APEC are needed.

SUMMARY

APEC is responsible for severe economic losses to the poultry industry worldwide and is also regarded as the potential source of human ExPECs. Disclosed herein are anti-APEC agents that can be used as therapeutics to control APEC infections in poultry.

In some embodiments, the anti-APEC agents can be growth inhibitors that target the APEC cell membrane. Bacterial cell membranes are regarded as promising targets for discovery of new antimicrobial therapeutics and to combat antimicrobial resistance. These growth inhibitors can be effective against multiple APEC strains, including antimicrobial-resistant APEC strains. As such, the growth inhibitors can be used as antimicrobials in response to an APEC outbreak. In addition, because of their activity on the APEC cell membrane, the growth inhibitors described herein can enhance the uptake and/or penetration of antibiotics that have intracellular targets and can interact synergistically with other membrane affecting antibiotics. As a result, combination of the growth inhibitors described herein with other antibiotics can increase the activity of the other antibiotics and/or reduce the amount of the other antibiotics needed to combat APEC. The growth inhibitors can also exhibit activity against APEC biofilms. Accordingly, the growth inhibitors described herein can be used to eradicate APEC biofilms in poultry facilities (e.g., in water lines and drinker systems).

In some embodiments, the anti-APEC agents can be quorum sensing inhibitors (QSIs). QSIs can reduce the bacterial virulence of APEC. In some cases, the QSIs may not, per se, inhibit APEC growth, but instead may interfere with QS-regulated processes including virulence factor release, biofilm formation, motility, exopolysaccharide synthesis, stress survival, cell division, and pathogenesis in APEC. In some embodiments, the QSIs can possess anti-biofilm effect against APEC, for example, through the down-regulation of biofilm- and capsular polysaccharides-associated genes which are important for bacterial adherence, interactions with host cells, and resistance to host immunity. The QSIs can be administered to treat or prevent an APEC infection. If desired, QSIs can be administered with out an additional antimicrobial agent to treat or prevent an APEC infection. In these cases, the QSI can reduce the virulence of the APEC, allowing an avian subject's immune system to ward off the APEC infection. In other cases, QSIs can be co-administered with an additional antimicrobial agent (e.g., an additional antibiotic agent, such as one or more of the growth inhibitors described herein). In these cases, the QSI can reduce the virulence of the APEC and/or sensitize the APEC to the additional antimicrobial agent.

The anti-APEC agents described herein can be administered alone or in combination to control APEC infections in poultry. For example, the anti-APEC agents can be administered to an avian subject infected with APEC to treat the APEC infection. Anti-APEC agents can also be used to destroy resident APEC biofilms in poultry facilities (e.g., in water lines and drinker systems). Anti-APEC agents can also be used prophylactically as part of a flock management protocol. For example, a flock can be monitored for APEC infection. In the event that an APEC infection is detected in one or more members of the flock, one or more anti-APEC agents can be administered to all members of the flock (e.g., in their water and/or feed supply) to treat any avian subjects in the flock infected with APEC and/or prevent APEC infection from spreading to other flock members.

In certain embodiments, these methods can involve the administration of a combination of a growth inhibitor described herein and a QSI described herein. In certain embodiments, these methods can involve the administration of a combination of a growth inhibitor described herein and a conventional antibiotic (e.g., a tetracycline, a sulfonamide, an aminoglycoside, a β-lactam antimicrobial, and/or a quinolone). In certain embodiments, these methods can involve the administration of a combination of a QSI described herein and a conventional antibiotic (e.g., a tetracycline, a sulfonamide, an aminoglycoside, a β-lactam antimicrobial, and/or a quinolone).

DESCRIPTION OF DRAWINGS

FIG. 13A shows the survival rate of the treated larvae. FIG. 13B shows the bacterial load in dead larvae at different time points (24, 48, 72 h) and in live larvae at 72 h. FIG. 13C shows the toxic effect of each compound on *G. mellonella* larvae. The larvae were treated with the AI-2 inhibitors (12.5 µg/larva) and inoculated with APEC O78 (8.5 µL of $8.5×10^3$ CFU) survival monitored for 72 hrs. The results of two independent experiments were averaged. Significant difference between AI-2 inhibitors treated compared to DMSO treated control at 48 $h^a$ and 72 $h^b$ ($P<0.05$).

FIG. 14A shows a heat map showing the impact of the selected AI-2 inhibitors on gene expression of QS and virulence associated genes. Effect on gene expression was assessed using 100 µM of AI-2 inhibitors. Three independent experiments were conducted and the average fold change was calculated using ΔΔct at map showing the impact of the selected ≥ or ≤1.5) were considered differentially expressed. FIG. 14B shows a principal component analysis (PCA) of the qRT-PCR data. Numbers above the arrows indicate the correlation (r) between the AI-2 inhibitors based on the gene expression data. The PCA analysis is based on the fold change of gene expression data.

FIG. 20A is a plot of the reduction in mortality in QS-treated groups compared to the DMSO control group. FIGS. 20B-20E are plots showing the APEC load (log CFU/g of tissues) in the internal organs (liver (FIG. 20B), heart (FIG. 20C), kidney (FIG. 20D), lung (FIG. 20E)) of compounds treated groups compared to DMSO control group.

DETAILED DESCRIPTION

Definitions

Figure 1A:
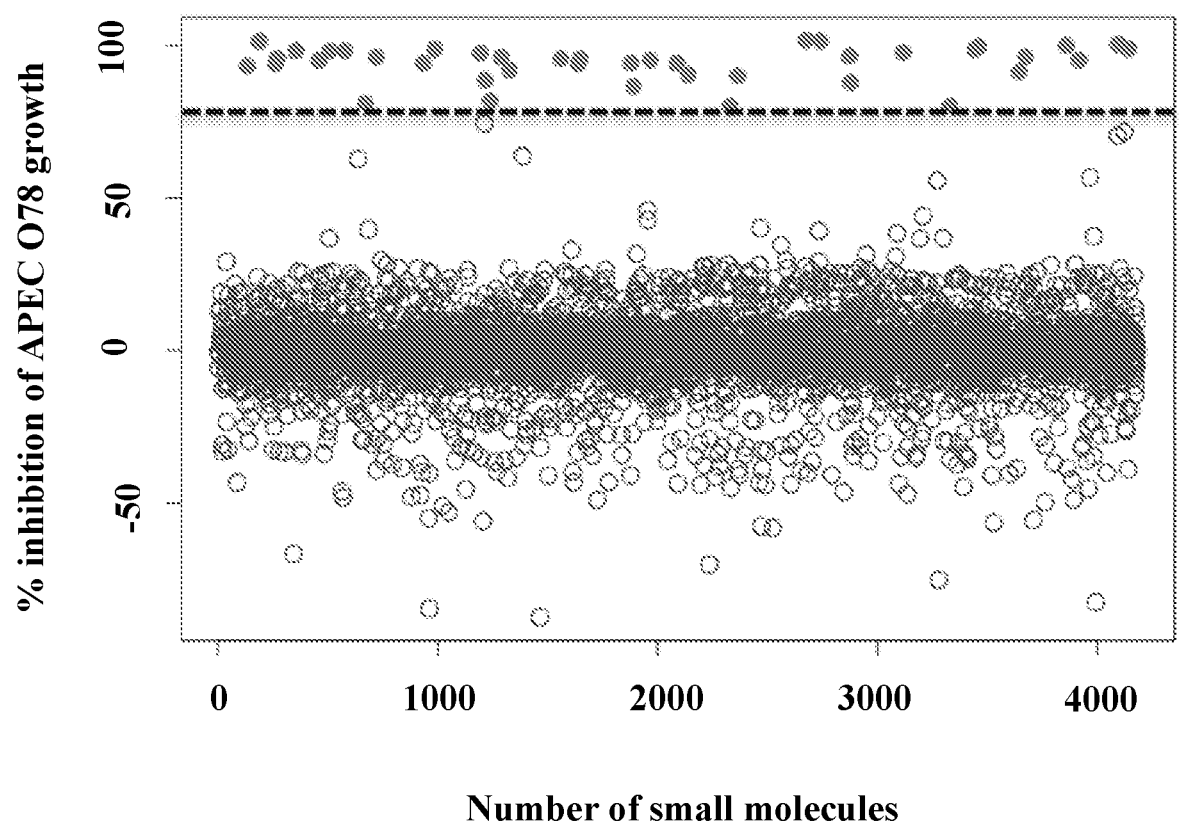
FIG. 1A HTS of 4,182 SMs to identify novel anti-APEC SMs. The growth inhibitory activity was assessed by incubating APEC O78 in the presence of SMs (100 μM) followed by kinetic $OD_{600}$ measurement for 12 h using Sunrise—Absorbance microplate reader. A total of 40 SMs (~1%) inhibited more than 80% growth of APEC O78 (indicated by dashed black line) and were considered as primary hits (red filled circles). Only 11 SMs (0.25% of total SMs) displayed bactericidal activity and were selected for further studies.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

At various places in the present specification, divalent linking substituents are described. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O—alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, the term "carbamyl" to a group of formula —C(O)NH$_2$.

As used herein, the term "carbonyl", employed alone or in combination with other terms, refers to a —C(=O)— group, which may also be written as C(O). As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "halo" refers to F, Cl, Br, or I. In some embodiments, a halo is F, Cl, or Br. In some embodiments, a halo is F or Cl.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 6-10 ring-forming carbon atoms. In some embodiments, cycloalkyl is adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

In some embodiments, the compounds described herein can contain one or more asymmetric centers and thus occur as racemates and racemic mixtures, enantiomerically enriched mixtures, single enantiomers, individual diastereomers and diastereomeric mixtures (e.g., including (R)- and (S)-enantiomers, diastereomers, (D)-isomers, (L)-isomers, (+) (dextrorotatory) forms, (-) (levoratatory) forms, the racemic mixtures thereof, and other mixtures thereof). Additional asymmetric carbon atoms can be present in a substituent, such as an alkyl group. All such isomeric forms, as well as mixtures thereof, of these compounds are expressly included in the present description. The compounds described herein can also or further contain linkages wherein bond rotation is restricted about that particular linkage, e.g. restriction resulting from the presence of a ring or double bond (e.g., carbon-carbon bonds, carbon-nitrogen bonds such as amide bonds). Accordingly, all cis trans and E/Z isomers and rotational isomers are expressly included in the present description. Unless otherwise mentioned or indicated, the chemical designation of a compound encompasses the mixture of all possible stereochemically isomeric forms of that compound.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that the compounds described herein include all possible regioisomers, and mixtures thereof, which can be obtained in pure form by standard separation procedures known to those skilled in the art, and include, but are not limited to, column chromatography, thin-layer chromatography, and high-performance liquid chromatography.

Unless specifically defined, compounds provided herein can also include all isotopes of atoms occurring in the intermediates or final compounds. Isotopes include those atoms having the same atomic number but different mass numbers. Unless otherwise stated, when an atom is designated as an isotope or radioisotope (e.g., deuterium, [$^{11}$C], [$^{18}$F]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977). Conventional methods for preparing salt forms are described, for example, in *Handbook of Pharmaceutical Salts: Properties, Selection, and Use*, Wiley-VCH, 2002.

Anti-APEC Agents

APEC is responsible for severe economic losses to the poultry industry worldwide and is also regarded as the potential source of human ExPECs. Disclosed herein are anti-APEC agents that can be used as therapeutics to control APEC infections in poultry.

In some embodiments, the anti-APEC agents can be growth inhibitors that target the APEC cell membrane. Bacterial cell membranes are regarded as promising targets for discovery of new antimicrobial therapeutics and to combat antimicrobial resistance. These growth inhibitors can be effective against multiple APEC strains, including antimicrobial-resistant APEC strains. As such, the growth inhibitors can be used as antimicrobials in response to an APEC outbreak. In addition, because of their activity on the APEC cell membrane, the growth inhibitors described herein can enhance the uptake and/or penetration of antibiotics that have intracellular targets and can interact synergistically with other membrane affecting antibiotics. As a result, combination of the growth inhibitors described herein with other antibiotics can increase the activity of the other antibiotics and/or reduce the amount of the other antibiotics needed to combat APEC. The growth inhibitors can also exhibit activity against APEC biofilms. Accordingly, the growth inhibitors described herein can be used to eradicate APEC biofilms in poultry facilities (e.g., in water lines and drinker systems).

In some embodiments, the growth inhibitor can be a compound defined by Formula I below

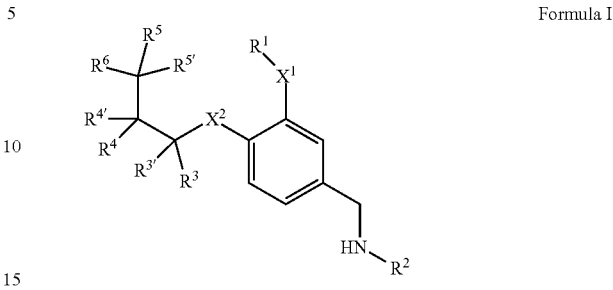

Formula I or a pharmaceutically acceptable salt, ester, or prodrug thereof, wherein $X^1$ and $X^2$ are independent selected from —O— and —S—;

$R^1$ is selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^X$ groups;

$R^2$ is —$(CR^7R^{7'})_nR^8$;

$R^3$, $R^{3'}$, $R^4$, $R^{4'}$, $R^5$, and $R^{5'}$ are each selected from H, OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^6$ is selected from a $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^X$ groups;

each $R^7$ and $R^{7'}$, when present, are each independently selected from H, OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^8$ is selected from $C_{3-10}$ cycloalkyl, $C_{6-10}$ aryl, 4-10 membered heterocycloalkyl, and 5-10 membered heteroaryl, wherein the $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^X$ groups;

each $R^X$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5.

In some embodiments of Formula I, $X^1$ and $X^2$ are both O.

In some embodiments of Formula I, $R^1$ is $C_{1-6}$ alkyl. In some embodiments of Formula I, $R^1$ is $CH_3$.

In some embodiments, $R^3$ and $R^{3'}$ are both H.

In some embodiments, $R^5$ and $R^{5'}$ are both H.

In some embodiments, $R^4$ is selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and $R^{4'}$ is H. In some embodiments, $R^4$ is OH and $R^{4'}$ is H.

In some embodiments, $R^6$ comprises a 5-membered ring (e.g., a $C_5$ cycloalkyl group, a 5 membered heterocycloalkyl group, or a 5-membered heteroaryl group). In some embodiments, $R^6$ comprises a pyrrolidine ring.

In some embodiments, $R^7$ and $R^{7'}$, when present, are both H.

In some embodiments, n is 1 or 2. In some embodiments, n is 1. In other embodiments, n is 2.

In some embodiments, $R^8$ is $C_{6-10}$ aryl optionally substituted by 1, 2, 3, or 4 independently selected $R^X$ groups. In certain embodiments, $R^8$ can comprise phenyl optionally substituted by 1, 2, 3, or 4 independently selected $R^X$ groups. In certain embodiments, $R^8$ can comprise naphthalenyl optionally substituted by 1, 2, 3, or 4 independently selected $R^X$ groups.

In some embodiments, $R^X$, when present, can be selected from halo, $C_{1-6}$ alkyl, and $C_{1-4}$ haloalkyl.

In some embodiments, the growth inhibitor can be a compound defined by Formula II below

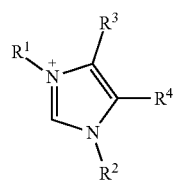

Formula II or a pharmaceutically acceptable salt, ester, or prodrug thereof, wherein $R^1$ and $R^2$ are individually selected from a $C_{1-22}$ alkyl, $C_{1-22}$ alkenyl, or $C_{1-22}$ alkynyl group optionally substituted by 1, 2, 3, 4, 5, or 6 independently selected $R^X$ groups;

$R^3$ and $R^4$ are individually selected from H, OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; or $R^3$ and $R^4$, together with the atoms to which they are attached, form a $C_6$ cycloalkyl, $C_6$ aryl, 6 membered heterocycloalkyl, or 6 membered heteroaryl ring, each of which is optionally substituted by 1, 2, 3, or 4 independently selected $R^X$ groups; and each $R^X$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the compound of Formula II can be defined by the formula below

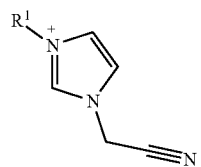

or a pharmaceutically acceptable salt, ester, or prodrug thereof, wherein $R^1$ is selected from a $C_{5-22}$ alkyl, $C_{5-22}$ alkenyl, or $C_{5-22}$ alkynyl group optionally substituted by 1, 2, 3, 4, 5, or 6 independently selected $R^X$ groups.

In some embodiments, the compound of Formula II can be defined by the formula below

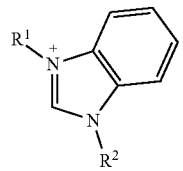

or a pharmaceutically acceptable salt, ester, or prodrug thereof, wherein $R^1$ and $R^2$ are individually selected from a $C_{1-22}$ alkyl, $C_{1-22}$ alkenyl, or $C_{1-22}$ alkynyl group optionally substituted by 1, 2, 3, 4, 5, or 6 independently selected $R^X$ groups. In some of these embodiments, at least one of $R^1$ and $R^2$ is selected from a $C_{5-22}$ alkyl, $C_{5-22}$ alkenyl, or $C_{5-22}$ alkynyl group optionally substituted by 1, 2, 3, 4, 5, or 6 independently selected $R^X$ groups.

In some embodiments, the growth inhibitor can be a compound defined by Formula III below

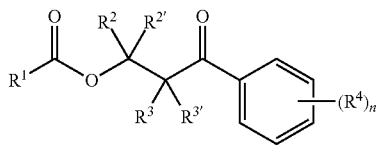

Formula III or a pharmaceutically acceptable salt, ester, or prodrug thereof, wherein $R^1$ is selected from $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^X$ groups;

$R^2$, $R^{2'}$, $R^3$, and $R^{3'}$ are each selected from H, OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^X$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^4$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5.

In some embodiments, $R^1$ is $C_{1-6}$ alkyl.

In some embodiments, $R^2$ is selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and $R^{2'}$ is H. In some embodiments, $R^2$ is $C_{1-4}$ haloalkyl and $R^{2'}$ is H.

In some embodiments, $R^3$ is selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and $R^{3'}$ is H. In some embodiments, $R^3$ halo and $R^{3'}$ is H.

In some embodiments, n is 1 or 2. In some embodiments, n is 1.

In some embodiments, $R^4$, when present, can be selected from OH, $NO_2$, CN, and halo. In some embodiments, an $R^4$ group can be present at the para position of the phenyl ring to which it is attached.

In some embodiments, the growth inhibitor can be a compound defined by Formula IV below

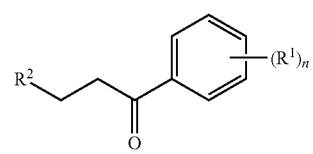

Formula IV or a pharmaceutically acceptable salt, ester, or prodrug thereof, wherein each $R^1$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

R² is selected from a C$_{3-10}$ cycloalkyl, C$_{6-10}$ aryl, 4-10 membered heterocycloalkyl, and 5-10 membered heteroaryl are each optionally substituted by 1, 2, 3, or 4 independently selected R$^X$ groups;

each R$^X$, when present, is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino; and n is 0, 1, 2, 3, 4, or 5.

In some embodiments, the growth inhibitor can be a compound defined by Formula V below

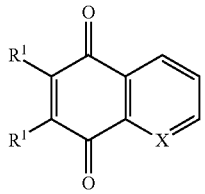

Formula V or a pharmaceutically acceptable salt, ester, or prodrug thereof, wherein X is N or CH; and each R¹ is independently selected from H, OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In some embodiments, the growth inhibitor can be a compound defined by Formula VI below

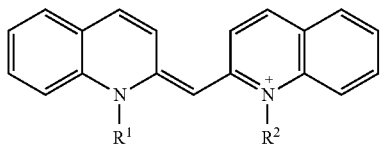

Formula VI or a pharmaceutically acceptable salt, ester, or prodrug thereof, wherein R¹ and R² are each selected from C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, 4-10 membered heterocycloalkyl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, 5-10 membered heteroaryl-C$_{1-4}$ alkylene; wherein the C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, 4-10 membered heterocycloalkyl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, and 5-10 membered heteroaryl-C$_{1-4}$ alkylene are each optionally substituted with 1, 2, 3, or 4 independently selected R$^X$ groups; and each R$^X$, when present, are each independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In some embodiments, the growth inhibitor can be a compound defined by Formula VII below

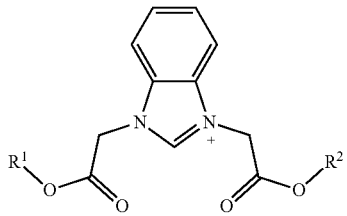

Formula VII or a pharmaceutically acceptable salt, ester, or prodrug thereof, wherein R¹ and R² are each selected from C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, 4-10 membered heterocycloalkyl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, 5-10 membered heteroaryl-C$_{1-4}$ alkylene; wherein the C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, 4-10 membered heterocycloalkyl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, and 5-10 membered heteroaryl-C$_{1-4}$ alkylene are each optionally substituted with 1, 2, 3, or 4 independently selected R$^X$ groups; and each R$^X$, when present, are each independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In some embodiments, the growth inhibitor can be a compound defined by Formula VIII below

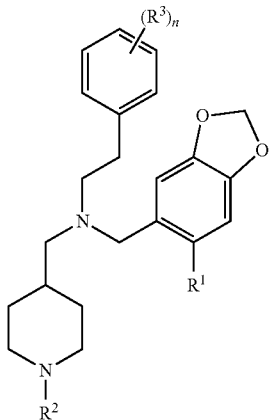

Formula VIII or a pharmaceutically acceptable salt, ester, or prodrug thereof, wherein $R^1$ is selected from H, OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^2$ is selected from $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^X$ groups; and each $R^3$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^X$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5.

In some embodiments, the anti-APEC agents can be a quorum sensing inhibitor (QSI) (also referred to as AI-2 inhibitors) that target decreases the virulence of APEC. QSIs can reduce the bacterial virulence of APEC. In some cases, the QSIs may not, per se, inhibit APEC growth, but instead may interfere with QS-regulated processes including virulence factor release, biofilm formation, motility, exopolysaccharide synthesis, stress survival, cell division, and pathogenesis in APEC. In some embodiments, the QSIs can possess anti-biofilm effect against APEC, for example, through the down-regulation of biofilm- and capsular polysaccharides-associated genes which are important for bacterial adherence, interactions with host cells, and resistance to host immunity. The QSIs can be administered to treat or prevent an APEC infection. If desired, QSIs can be administered with out an additional antimicrobial agent to treat or prevent an APEC infection. In these cases, the QSI can reduce the virulence of the APEC, allowing an avian subject's immune system to ward off the APEC infection. In other cases, QSIs can be co-administered with an additional antimicrobial agent (e.g., an additional antibiotic agent, such as one or more of the growth inhibitors described herein). In these cases, the QSI can reduce the virulence of the APEC and/or sensitize the APEC to the additional antimicrobial agent.

In some embodiments, the QSI can be a compound defined by Formula IX below

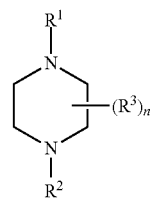

Formula IX or a pharmaceutically acceptable salt, ester, or prodrug thereof, wherein $R^1$ is selected from —$(CR^4R^{4'})_m R^5$, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^X$ groups;

$R^2$ is selected from —$(CR^4R^{4'})_m R^5$, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^X$ groups;

each $R^3$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^4$ and $R^{4'}$, when present, is independently selected from H, OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^5$ is independently selected from $OR^A$, $NR^AR^B$, $C(O)NR^AR^B$, $C(O)OR^A$, $C_{3-10}$ cycloalkyl, $C_{6-10}$ aryl, 4-10 membered heterocycloalkyl, and 5-10 membered heteroaryl, wherein the $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^X$ groups $R^A$ and $R^B$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^X$ groups; or alternatively, any $R^A$ and $R^B$ attached to the same N atom, together with the N atom to which they are attached, form a 4-6 membered heterocycloalkyl group or a 5-6 membered heteroaryl group, each optionally substituted with 1, 2, or 3 independently selected $R^X$ groups;

each $R^X$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

m is 0, 1, 2, 3, 4, or 5; and n is 0, 1, 2, 3, or 4.

In some of these embodiments, the QSI can be defined by the formula below

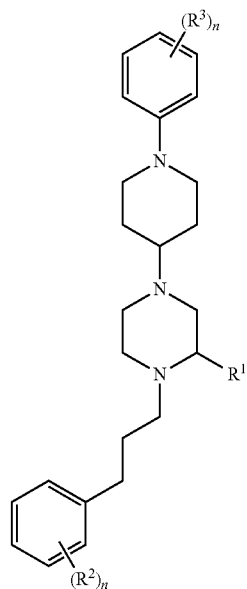

or a pharmaceutically acceptable salt, ester, or prodrug thereof, wherein $R^1$ is selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^2$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^3$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino; and each n is independently 0, 1, 2, 3, 4, or 5.

In some of these embodiments, the QSI can be defined by the formula below

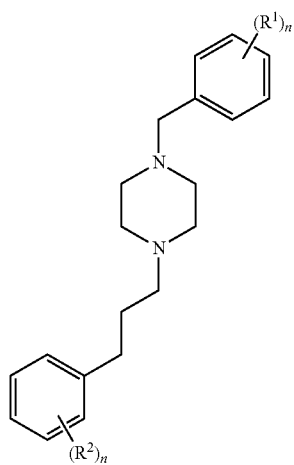

or a pharmaceutically acceptable salt, ester, or prodrug thereof, wherein each R$^1$, when present, is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^2$, when present, is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino; and each n is independently 0, 1, 2, 3, 4, or 5.

In some of these embodiments, the QSI can be defined by the formula below

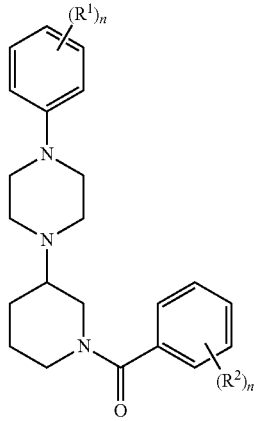

or a pharmaceutically acceptable salt, ester, or prodrug thereof, wherein each R$^1$, when present, is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^2$, when present, is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino; and each n is independently 0, 1, 2, 3, 4, or 5.

In some of these embodiments, the QSI can be defined by the formula below

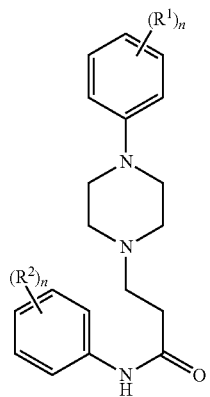

or a pharmaceutically acceptable salt, ester, or prodrug thereof, wherein each $R^1$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^2$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each n is independently 0, 1, 2, 3, 4, or 5.

In some embodiments, the QSI can be a compound defined by Formula X below

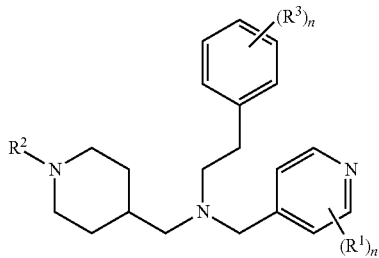

Formula X or a pharmaceutically acceptable salt, ester, or prodrug thereof, wherein each $R^1$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^2$ is selected from $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^X$ groups;

each $R^3$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^X$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is independently 0, 1, 2, 3, or 4.

In some embodiments, the QSI can be a compound defined by Formula XI below

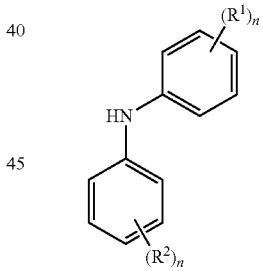

Formula XI or a pharmaceutically acceptable salt, ester, or prodrug thereof, wherein each $R^1$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^2$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each n is independently 0, 1, 2, 3, 4, or 5.

In some embodiments, the QSI can be a compound defined by Formula XII below

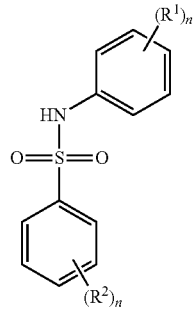

Formula XII or a pharmaceutically acceptable salt, ester, or prodrug thereof, wherein each $R^1$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^2$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each n is independently 0, 1, 2, 3, 4, or 5.

In some embodiments, the QSI can be a compound defined by Formula XIII below

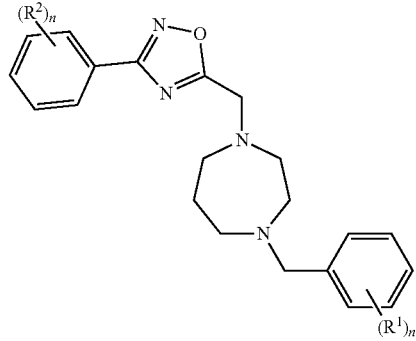

Formula XIII or a pharmaceutically acceptable salt, ester, or prodrug thereof, wherein each $R^1$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^2$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each n is independently 0, 1, 2, 3, 4, or 5.

In some embodiments, the QSI can be a compound defined by Formula XIV below

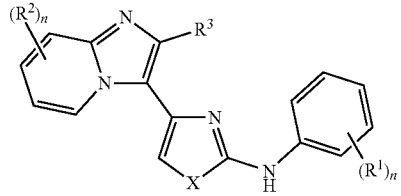

Formula XIV or a pharmaceutically acceptable salt, ester, or prodrug thereof, wherein X is O or S;

each $R^1$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^2$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^3$ is selected from H, OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each n is independently 0, 1, 2, 3, 4, or 5.

In some embodiments, the QSI can be a compound defined by Formula XV below

Formula XV or a pharmaceutically acceptable salt, ester, or prodrug thereof, wherein $R^1$ is selected from $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^X$ groups;

each $R^2$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^X$, when present, is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5.

The anti-APEC agents described herein can be administered alone or in combination to control APEC infections in poultry. In one embodiment, an avian subject is administered a therapeutically-effective amount of a compound of Formulas I through XV or any combination thereof. A "therapeutically-effective" amount as used herein is an amount of a compound of Formulas I through XV that is sufficient to alleviate (e.g., mitigate, decrease, reduce) at least one of the symptoms associated with APEC. It is not necessary that the administration of the compound eliminate the symptoms of APEC, as long as the benefits of administration of compound outweigh the detriments. Likewise, the terms "treat" and "treating" in reference to APEC, as used herein, are not intended to mean that the avian subject is necessarily cured of APEC or that all clinical signs thereof are eliminated, only that some alleviation or improvement in the condition of the avian subject is affected by administration of the compound of Formulas I through XV.

The term "avian" and "avian subjects," as used herein, is intended to include males and females of any avian species, but is primarily intended to encompass poultry which are commercially raised for eggs, meat or as pets. Accordingly, the terms "avian" and "avian subject" are particularly intended to encompass chickens, turkeys, ducks, geese, quail, pheasant, parakeets, parrots, and the like. In certain embodiments, the avian subject can be a chicken (e.g., a broiler or a layer). The avian subject may be a hatched bird, which term encompasses newly-hatched (i.e., about the first three days after hatch) as well as post-hatched birds such as, for example, adolescent, and adult birds.

Avian subjects may be administered the compounds described herein by any suitable means. Exemplary means are oral administration (e.g., in the feed or drinking water), intramuscular injection, subcutaneous injection, intravenous injection, intra-abdominal injection, eye drop, or nasal spray. Avian subjects may also be administered the compounds in a spray cabinet, i.e., a cabinet in which the birds are placed and exposed to a vapor containing vaccine, or by coarse spray. When administering the compounds described herein to birds post-hatch, administration by subcutaneous injection or spray cabinet are commonly used techniques.

In some embodiments, the anti-APEC agents can be administered to an avian subject infected with APEC to treat the APEC infection. Anti-APEC agents can also be used to destroy resident APEC biofilms in poultry facilities (e.g., in water lines and drinker systems). Anti-APEC agents can also be used prophylactically as part of a flock management protocol. For example, a flock can be monitored for APEC infection. In the event that an APEC infection is detected in one or more members of the flock, one or more anti-APEC agents can be administered to all members of the flock (e.g., in their water and/or feed supply) to treat any avian subjects in the flock infected with APEC and/or prevent APEC infection from spreading to other flock members.

In certain embodiments, these methods can involve the administration of a combination of a growth inhibitor described herein and a QSI described herein. In certain embodiments, these methods can involve the administration of a combination of a growth inhibitor described herein and a conventional antibiotic (e.g., a tetracycline, a sulfonamide, an aminoglycoside, a β-lactam antimicrobial, and/or a quinolone). In certain embodiments, these methods can involve the administration of a combination of a QSI described herein and a conventional antibiotic (e.g., a tetracycline, a sulfonamide, an aminoglycoside, a β-lactam antimicrobial, and/or a quinolone).

By way of non-limiting illustration, examples of certain embodiments of the present disclosure are given below.

EXAMPLES

Example 1: Small Molecules Affecting Cell Membrane as Potential Therapeutics for Avian Pathogenic *Escherichia coli* (APEC)

Avian pathogenic *Escherichia coli* (APEC), a common bacterial pathogen of poultry, causes multiple extra-intestinal diseases in poultry which results in significant economic losses to the poultry industry worldwide. In addition, APEC are a subgroup of extra-intestinal pathogenic *E. coli* (ExPEC), and APEC contaminated poultry products are a potential source of foodborne ExPEC infections to humans and transfer of antimicrobial resistant genes. The emergence of multi-drug resistant APEC strains and the limited efficacy of vaccines necessitate novel APEC control approaches. In this example, a small molecule (SM) library was screened and 11 SMs bactericidal to APEC were identified. The identified SMs were effective against multiple APEC serotypes, biofilm embedded APEC, antimicrobials resistant APECs, and other pathogenic *E. coli* strains. Microscopy revealed that these SMs affect the APEC cell membrane. Exposure of SMs to APEC revealed no resistance. Most SMs were least toxic to chicken and human cells and reduced the intracellular APEC load. Treatment with most SMs extended the wax moth larval survival and reduced the intra-larval APEC load. This example facilitates the future development of antimicrobial therapeutics for the effective management of APEC infections in poultry as well as other *E. coli* related foodborne zoonosis including APEC related ExPEC infections in humans.

Introduction

APEC, an extra-intestinal pathogenic *E. coli* (ExPEC), is one of the most common bacterial pathogens affecting chickens, turkeys, and other avian species. APEC can affect birds of all ages and in all types of production systems either as primary or secondary pathogen. Serotypes O1, O2, O8, O18, O35, O78, O109, O115 are commonly associated with infections and among them O1, O2, and O78 constitute more than 80% of the cases. APEC causes multiple extra-intestinal infections in poultry such as airsacculitis, perihepatitis, pericarditis, peritonitis, omphalitis, salphingitis, and cellulitis which subsequently leads to high morbidity and mortality (up to 20%), reduced body weight gain and egg production, and increased carcasses condemnation at slaughter (up to 45%), thus resulting in severe economic losses to the poultry industry worldwide.

Several studies have also reported similarities of APEC with human ExPECs such as uropathogenic *E. coli* (UPEC) and neonatal meningitis *E. coli* (NMEC) in their phylogenetic background, genome content, and virulence factors. Thus, poultry products are considered as major reservoirs for ExPECs and the consumption of APEC contaminated poultry products are a potential source of foodborne ExPEC infection to humans. Further, APEC are also a source for transmission of antimicrobials resistant genes to humans which makes treatment of human ExPECs associated infections difficult. Therefore, in addition to its impact on poultry health and productivity, the foodborne transmission of APEC to humans necessitates effective control of APEC infections in poultry.

Antimicrobial medication using tetracyclines, cephalosporins, sulfonamides, or quinolones is the major approach currently employed to reduce the incidence and mortality associated with APEC infections in poultry worldwide. However, multi-drug resistant (MDR) APEC strains resistant to tetracyclines, sulfonamides, aminoglycosides, β-lactam antimicrobials, quinolones, and colistin are reported worldwide including major poultry producing countries; United States, China, Brazil, and European Union. In addition, currently available vaccines do not provide cross protection against multiple APEC serotypes due to heterogeneity (variability in genome content) among serotypes.

Small molecule (SM) libraries containing diverse SMs can provide the platform for novel antimicrobials discovery. SM libraries generally include low molecular weight (~200-500 Da), non-peptide, organic, synthetic or natural compounds with drug-like properties that can interact with biological molecules such as protein and nucleic acids and can alter their normal functions. The high-throughput screening (HTS) of SM libraries can identify the SMs that can either inhibit the bacterial growth or function of key bacterial enzymes. Previous studies have identified SMs having antimicrobial activity against several human and animal pathogens.

In this example, a SM library containing 4,182 SMs was screened to identify and characterize the novel antimicrobial therapeutics against APEC. The primary screening followed by secondary assays identified seven potent SMs affecting APEC cell membrane. These SMs were effective against multiple APEC serotypes, biofilm embedded APEC, antimicrobial resistant APECs, and other pathogenic *E. coli* strains. These SMs were least toxic to eukaryotic cells and were effective against intracellular and intra-larval APEC. These studies can facilitate the development of antimicrobial therapeutics for the effective management of APEC infections in poultry and thereby also reduce human ExPEC infections and transfer of antimicrobial resistant genes.

Materials and Methods

Small molecules library. A pre-selected enriched SM library containing a total of 4,182 'yactives' selected through pre-screening of 81,320 compounds was obtained from ChemBridge at 10 mM concentration dissolved in 100% dimethyl sulfoxide (DMSO) in 96 well plates and plates were stored at −80° C. until further use.

Bacterial strains, culture conditions, and media. APEC serotypes stored in 25% glycerol at −80° C. were inoculated into LB broth and grown overnight at 37° C. with shaking at 200 rpm. For screening purpose, M63 minimal media was used to grow APEC serotypes. The use of minimal media allows the slow APEC growth, mimics the nutrient deficient host condition, and has been shown to increase the hits rate.

Primary Screening. To identify the APEC growth inhibitors, SM library was screened against APEC O78 which is one of the most frequently isolated APEC serotypes from avian colibacillosis cases. One μL SMs (final concentration of 100 μM) were added using a slotted pin tool (V and P Scientific, San Diego, Calif., USA) to the wells of the 96-well plate containing 100 μL of overnight grown 0.05 $OD_{600}$ ($7\times10^7$ CFU/mL) adjusted APEC culture. Controls (four replicates/plate) containing one μL of 100% DMSO (final concentration of 1%), one μL CHL (20 μg/mL), one μL KAN (50 μg/mL), and 100 μL of M63 media were included. Plate was then incubated at 37° C. for 12 h in Sunrise—Absorbance microplate reader (Tecan Group Ltd. San Jose, Calif.) with kinetic $OD_{600}$ measurement every 30 mins. The quality of screening was assessed by calculating the Z'-score as described previously. The growth inhibition of APEC was calculated by using the formula as previously described. The SMs inhibiting at least 80% of the APEC growth were selected as primary hits. Culture from wells considered as hits were subsequently subcultured on LB agar plate to determine the bactericidal effect (no APEC recovered on plating following exposure to SM); these cidal SMs were selected for further studies.

MIC and MBC determination. SMs were two-fold serially diluted from 200 μM to 6.25 μM to determine their MIC and MBC. One μL SM of each concentration was transferred to each well of a 96-well plate containing 100 μL of the 0.05 $OD_{600}$ adjusted APEC O78 culture in M63 media. Growth was monitored in Sunrise—Absorbance microplate reader as described above. MIC was indicated by lowest concentration of SM with non-elevated $OD_{600}$ measurement. MBC was determined by absence of APEC growth on LB agar plate following subculture. In addition, MIC and MBC of cidal SMs were also determined against multiple APEC serotypes (O1, O2, O8, O15, O18, O35, O109, and O115) that are commonly associated with colibacillosis cases to determine their spectrum of activity. Two independent experiments were conducted. The activity of cidal SMs were also tested at 100 μM in M63 media against Shiga toxin-producing (STEC) O157 and O26 strains.

Effect against antimicrobials resistant APECs. Initially, antimicrobial susceptibility profile was established for all the tested APEC serotypes using cation-adjusted Muller-Hinton broth (CAVHB) micro-dilution method according to clinical and laboratory standards institute (CLSI) guidelines. Four antimicrobials; AMP, CIP, CST, and TET that are currently used in poultry industry and belonging to different classes of antimicrobials; penicillins, quinolones, polymixins, and tetracyclines, respectively were evaluated for susceptibility according to their MIC breakpoints for resistance (AMP≥16 μg/mL, CIP≥4 μg/mL, CST≥4 μg/mL, and TET≥16 μg/mL). To determine the effect against antimicrobial resistant APECs, the MIC and MBC of cidal SMs were compared between the antimicrobial susceptible and resistant APEC serotypes.

Effect against beneficial microbes. SMs were screened against different beneficial microbes to determine their specificity. SMs were added at 100 μM to 100 μL of 0.05 $OD_{600}$ adjusted bacterial cultures in specific growth media in 96-well plate, and plate was incubated under indicated conditions. The specific growth media and conditions required for beneficial microbes limits the use of minimal media. Following incubation, endpoint $OD_{600}$ was measured and cultures from the wells with non-elevated $OD_{600}$ were plated on selective agar plates to determine the bactericidal effect.

Effect against biofilm embedded APEC. The effect of cidal SMs against biofilm embedded APEC was determined using MBEC High-throughput (HTP) assay (Innovotech Inc., AB, Canada). Briefly, 150 μL of 0.05 $OD_{600}$ adjusted APEC O78 culture was aliquoted into each well of the MBEC device containing polystyrene pegs and incubated at 37° C. for 36 h in LB media under stationary condition. After biofilm formation, the pegs were washed to remove loosely adherent planktonic bacteria, transferred to new 96-well plate, and challenged with different concentrations of SMs (0.5×, 1×, 2×, 4×, and 8×MIC) in 200 μL M63 media. The plate was incubated in the dark for 18 h at 37° C. with rotation at 110 rpm. The DMSO (1%) and M63 media were used as positive and negative controls, respectively. Following incubation, MIC of SMs in challenged plate was recorded. The SMs exposed pegs were then transferred to a new 96-well plate containing PBS and sonicated for 30 mins (Aquasonic ultrasonic cleaner, VWR) to disrupt the biofilm. The sonicated suspensions were ten-fold serially diluted and plated on LB agar plate. Biofilm embedded APEC bacteria were enumerated and minimum biofilm eradication concentration (MBEC) of k; j SMs were determined. Two independent experiments were conducted.

Antimicrobial resistance studies. To evaluate APEC O78 potential to acquire resistance against cidal SMs, single step and sequential passage resistance assays were performed in M63 media. Briefly, for single step resistance assay, SMs were mixed with 1.5 mL of molten M63 agar at a final concentration of 2×MBC and transferred to wells of a sterile 24-well plate. Fifty μL of overnight grown APEC O78 (~$10^9$ CFU) culture was plated over the solidified SM amended M63 agar. The plate was incubated for 15 days in the dark at 37° C. After 15 days, any colonies that grew on the agar were assessed for resistance by determining the MIC and MBC as described above.

For sequential passage resistance assay, SMs were added at a final concentration of 0.75×MIC (concentration that allows at least 70% growth inhibition) to the 100 μL of the 0.05 $OD_{600}$ adjusted APEC O78 culture in M63 media in a 96-well plate. The plate was then incubated in the dark at 37° C. with shaking at 150 rpm for 18 h. After the first incubation, bacterial pellet was resuspended in a fresh M63 media amended with 0.75×MIC of each SM and grown as above. This procedure was repeated 14 times. Following 15 passages, susceptibility (MIC and MBC) of APEC to SMs was determined. DMSO (1%), 20 μg/mL chloramphenicol, 50 μg/mL kanamycin, and M63 media were included as controls in both the assays. Experiments were conducted in duplicate wells.

Confocal and scanning electron microscopy. Confocal microscopy was used for bacterial cytological profiling (BCP) to identify the cellular pathways targeted by SMs as described previously. Briefly, 100 μL of logarithmic-phase APEC O78 culture grown in M63 media was treated with 2×MBC of SMs and incubated at 37° C. for 2 h with shaking at 200 rpm. After incubation, treated cultures were centrifuged, washed, and resuspended in 100 µL PBS. FM4-64 (1 µg/mL) and SYTO-9 (5 µM) (Molecular Probes/Invitrogen) were added to the bacterial cultures and incubated for 45 mins at room temperature with shaking at 150 rpm. Cultures were then centrifuged, washed, and resuspended in PBS to $1/10^{th}$ volume of the original cultures. Three µL of concentrated bacterial cultures was transferred onto an agarose pad containing 1.2% agarose and 20% LB medium. Microscopy was performed using Leica TCS SP6 confocal scanning microscope (Excitation/emission (nm); FM4-64 (515/640), SYTO-9 (485/498) and images were analyzed using ImageJV1.50.

The SMs treated APEC O78 cultures prepared above were also processed for scanning electron microscopy (SEM). SEM was performed for representative SMs (possessing similar structure and BCP). Briefly, one volume of bacterial culture was mixed with one volume of fixative (3% glutaraldehyde, 1% paraformaldehyde in 0.1 M potassium phosphate buffer, pH 7.2), and incubated at 4° C. overnight. The fixed bacterial cells were then centrifuged for 5 mins at 1,200×g, washed twice with PBS, and resuspended in 1% osmium tetroxide for 1 h at room temperature in the dark, followed by serial dehydration of the sample in ethanol and platinum splatter-coating. Visualization and imaging of the sample was performed using a Hitachi S-4700 scanning electron microscope.

Membrane permeability assays. Membrane permeability assays (crystal violet (CV) uptake and loss of 260/280 nm absorbing materials) were conducted. For CV uptake assay, APEC O78 culture grown in M63 media was adjusted to 0.2 $OD_{600}$ (~108 CFU/mL) were treated with 2×MBC of SMs for 30 mins followed by the incubation for 10 mins with 10 µg/mL CV. For the loss of 260/280 nm absorbing materials assay, APEC O78 cultures adjusted to 1.0 $OD_{600}$ (~$10^9$ CFU/mL) in M63 media were treated with 2×MBC of SMs for 1 h. DMSO (1%) and 0.25 M EDTA were used as negative and positive controls, respectively in both the assays. CV uptake was measured using the formula: (OD DMSO-OD SM/OD DMSO×100). Two independent experiments in duplicates were conducted.

Cytotoxicity of SMs to chicken and human cells. The cytotoxicity of cidal SMs to human Caco-2 and chicken HD11 cells were evaluated using Pierce Lactate Dehydrogenase (LDH) Cytotoxicity Assay Kit (Pierce, Thermo Scientific, Rockford, Ill., USA). Cytotoxicity was measured at OD 680 nm and 490 nm after exposing cultured epithelial and macrophage cells to 200 µM of SMs for 24 h. Two independent experiments with triplicate wells in each experiment were conducted.

Hemolytic activity of SMs to chicken RBCs. The hemolytic activity of cidal SMs to chicken RBCs was evaluated. Hemolysis was determined at OD 540 nm after exposing 10% RBCs suspension to 200 µM of SMs for 1 h. Two independent experiments with triplicate wells in each experiment were performed.

Effect of the SMs on intracellular survival of APEC in phagocytic and non-phagocytic cells. Intracellular survival assay was conducted to determine the effect of cidal SMs on APEC survival in phagocytic (HD11, THP-1) and non-phagocytic (Caco-2) cells. Briefly, mid-logarithmic phase grown APEC O78, O1, and O2 were washed and adjusted to $1 \times 10^7$ CFU/mL in cell culture incomplete media (no FBS and antibiotics). One-hundred µL adjusted APEC suspension was added at multiplicity of infection (MOI) 10 to wells of 96-well cell culture plate containing cultured macrophage (HD11, THP-1) and epithelial cells (Caco-2) and incubated for 1 h and 3 h, respectively. For APEC O1, invasion time was reduced by 3 times in all cell types as APEC O1 was found with significantly (P<0.01) higher invasiveness compared to O78 and O2. After incubation, cells were washed and treated with 150 µg/mL gentamicin for 1 h to kill extracellular APEC. The cells were then washed, replenished with incomplete media containing different concentrations (0.5×, 1×, 2×, and 4×MIC) of SMs, and incubated for 6 h. The cells were then lysed with 100 µL of 0.1% Triton X-100 for 5 mins, serially diluted, and plated on LB agar plate to enumerate viable bacteria. The intracellular bacteria in SMs treated wells were compared with DMSO (1%) treated wells. Two independent experiments in duplicate wells for each concentration of SMs were conducted.

Toxicity and efficacy of SMs in wax moth (*Galleria mellonella*) larvae. For toxicity evaluation, *G. mellonella* larvae (fifth instar) were inoculated with 12.5 µg of SMs (50 mg/kg body wt.) through last pro-leg using PB600-1 repeating dispenser (Hamilton, Reno, Nev.) attached to insulin syringe (31 gauge, 8 mm needle length) (ReliOn©, Bentonville, Ark.). For the inoculation, SMs were diluted in buffer mix (DMSO-30% plus 10 mM $MgSO_4$). Post-inoculation, larvae were placed inside sterile petri dishes and incubated up to 72 h in the dark at 37° C. and larval survival was monitored every 12 h. Non-treated larvae, larvae treated with the buffer mix, and larvae treated with CHL (75 mg/kg body wt.; dose sufficient to clear APEC infection in larvae) were used as controls.

For SMs efficacy testing, larvae were first injected with SMs mixed in buffer through the left hind pro-leg at dose rate as described above and incubated for 2 h at 37° C. Then, larvae were infected with $6 \times 10^4$ CFU of $Rif^r$ APEC O78 in 10 mM $MgSO_4$ on the right hind pro-leg. $Rif_r$ APEC O78 was generated by plating APEC on LB agar plate containing 50 µg/mL rifampicin for specific monitoring of APEC population inside the larvae. SMs displayed identical MIC and MBC to $Rif^r$ APEC O78 as the wild-type. Infection dose of $Rif^r$ APEC O78 to larvae was identified.

Infected larvae inoculated with buffer mix were used as positive control whereas larvae inoculated with CHL (75 mg/kg body wt.) were used as negative control. Post-inoculation, larval survival was monitored as above. For the quantification of APEC load inside the dead and live larvae, larvae from SMs treated and control groups were surface sterilized with 70% ethanol and homogenized in PBS. The suspension was tenfold serially diluted and plated on MacConkey agar plates supplemented with 50 µg/mL of rifampicin. The plates were then incubated overnight at 37° C. and APEC load was enumerated. Each experiment was repeated twice using larvae (n=20) obtained in different batches.

Statistical Analysis. The statistical significance of the effect of SMs in reducing biofilm embedded and intracellular APEC was determined by one-tailed student's t-test (P<0.01). The significance of CV uptake and increase of OD 260 and 280 nm absorbing bacterial supernatants in SMs treated samples was statistically analyzed by one-tailed student's t-test (P<0.05). Kaplan-Meir survival curves were generated using GraphPad Prism V.5 and were statistically analyzed (P<0.05) by log-rank test. APEC load inside the SMs treated and control larvae were analyzed by one-way ANOVA tukey's test using GraphPad Prism V.5 (P<0.05). APEC load inside the live and dead larvae were statistically compared (P<0.05) using one-tailed student's t-test. Correlation (r) between the larval survivability and APEC load was calculated using Microsoft Excel 2010.

Results

Figure 1B:
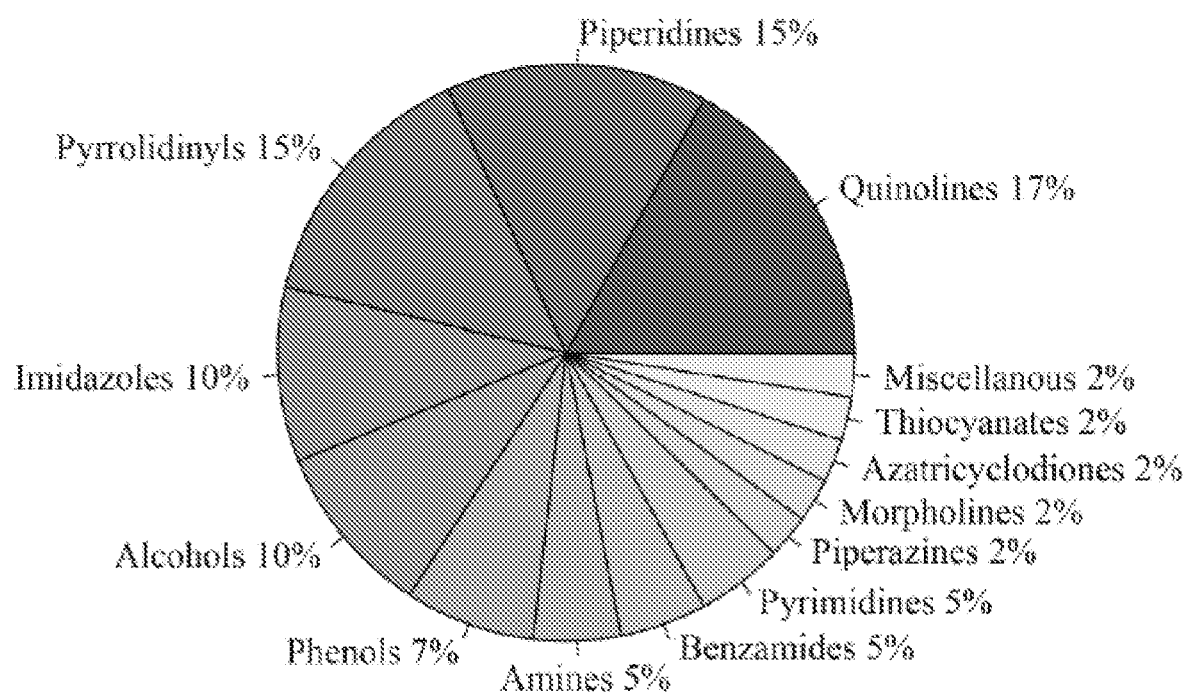
FIG. 1B shows the chemical groups of 40 primary hits. Chemical groups are shown as percentage of total hits.
Figure 1C:
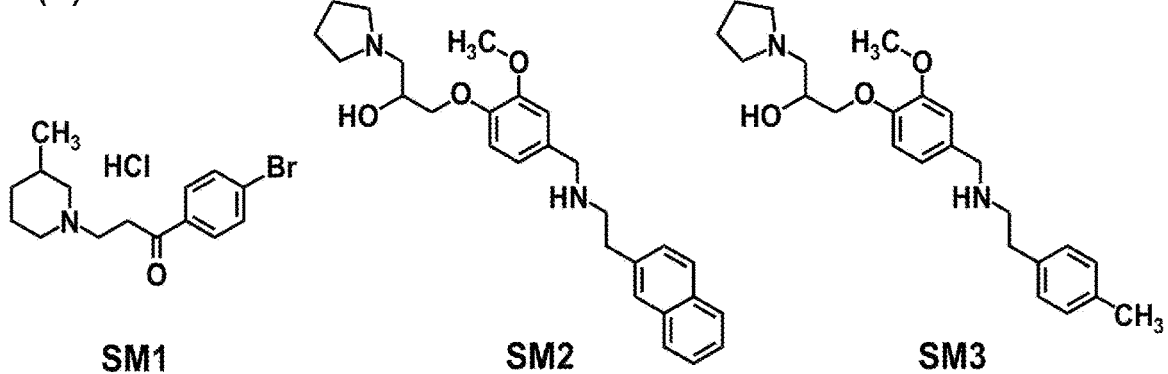
FIG. 1C shows the chemical structures of 11 selected anti-APEC bactericidal SMs identified in this study; Piperidines (SM1, SM11), Pyrrolidinyls (SM2, SM3, SM7), Imidazoles (SM4, SM5, SM6), Quinolines (SM8, SM9), Miscellaneous (SM10).
Figure 1C:
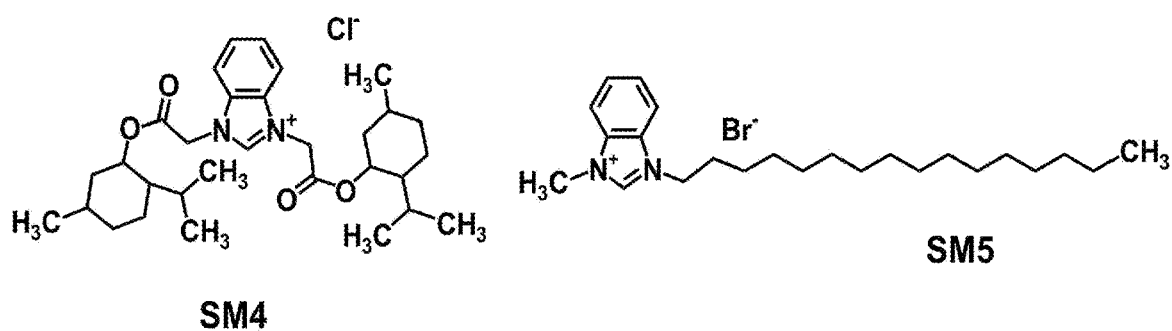
Figure 1C:
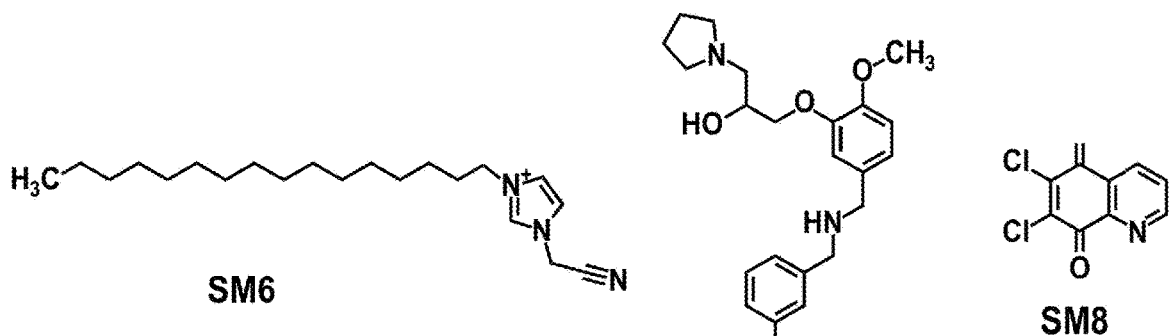
Figure 1C:
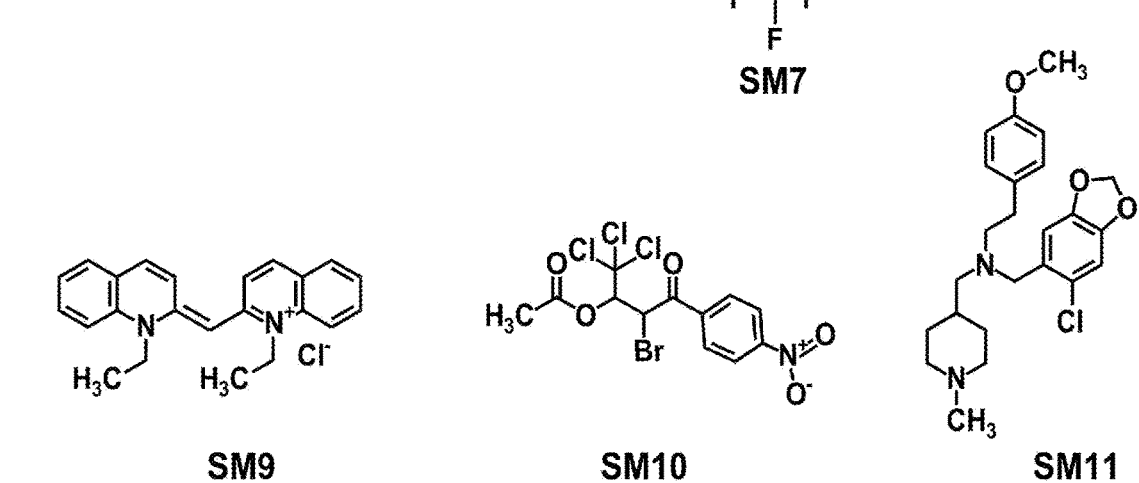

Primary screening identified 40 SMs inhibitory to APEC O78 growth. In the primary screening, 4,182 SMs were assessed for the growth inhibition of APEC O78 using 100 µM of SMs. A total of 40 SMs (hits) inhibited the APEC growth more than 80% (FIG. 1A). DMSO (1%; solvent for the SMs) did not affect the APEC growth. The average Z'-score for the HTS assay was 0.85 which is more than the Z'-score (>0.5) for a successful HTS assay. The majority of hits belonged to quinolines (~17%) followed by piperidines (~15%), pyrrolidinyls (~15%), and imidazoles (~10%) (FIG. 1B). Among these hits, 11 SMs (SM1-SM11) (FIG. 1C) exhibited bactericidal effect. These 11 SMs belonged to pyrrolidinyls (SM2, SM3, and SM7), imidazoles (SM4-SM6), quinolines (SM8 and SM9), piperidines (SM1 and SM11), and miscellaneous (SM10) group of chemical compounds (FIG. 1C).

Figure 2A:
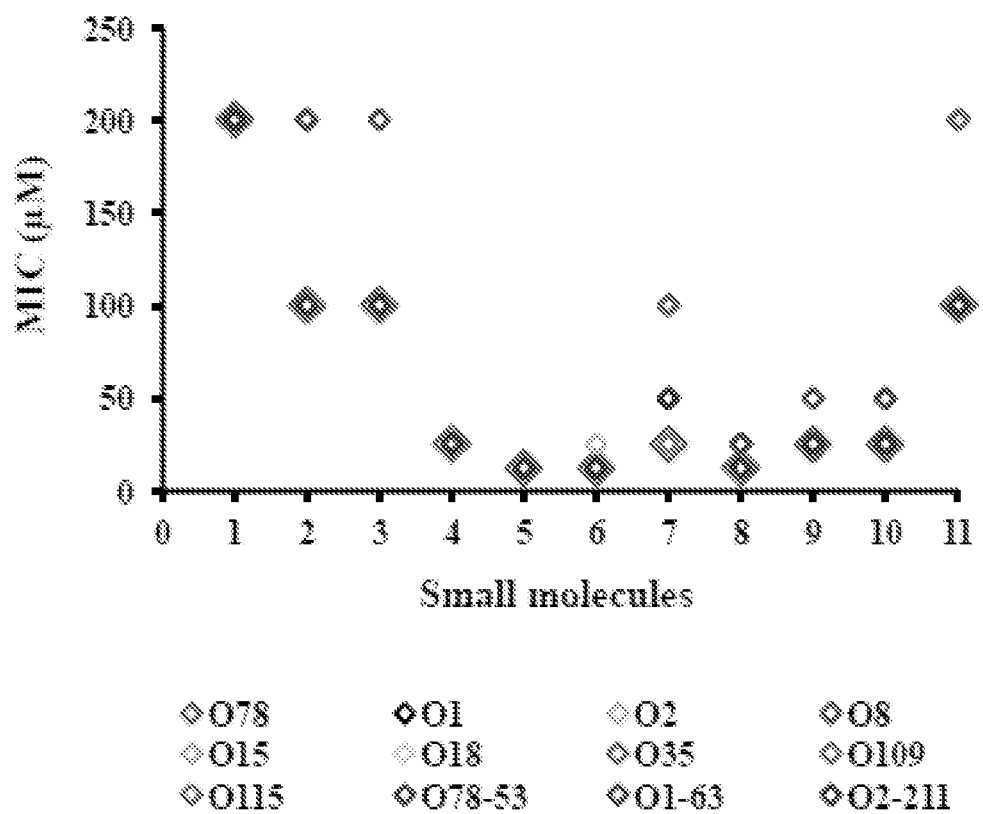
FIG. 2A is a plot of the MIC values of 11 cidal SMs against different APEC serotypes. The MIC of SMs against APEC O78 are shown with large open quadrangles to compare the MIC of SMs against other APEC serotypes.
Figure 2B:
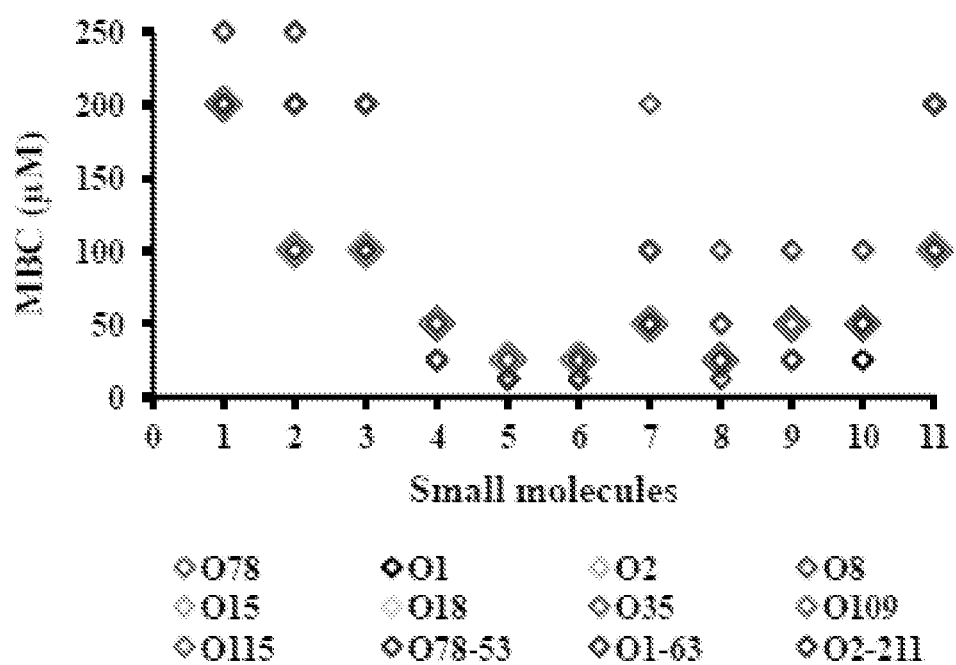
FIG. 2B is a plot of the MBC values of 11 cidal SMs against different APEC serotypes. The MBC of SMs against APEC O78 are shown with large open quadrangles to compare the MBC of SMs against other APEC serotypes.

Seven SMs possessed MIC as low as 25 µM. Of the 11 SMs, seven SMs (SM4-SM10) possessed MIC ranging from 12.5 to 25 µM (FIG. 2A, Table 1). The other three SMs (SM2, SM3, and SM11) possessed MIC of 100 µM. SM1 though was bactericidal to APEC at 100 µM in the primary screening, upon re-synthesis and subsequent testing it showed cidal activity only at 200 µM. Piperidines (SM1 and SM11) and pyrrolidinyls (SM2, SM3, and SM7) group of SMs were effective only at high MIC (25 µM-200 µM), whereas quinolines (SM8 and SM9) and imidazoles (SM4-SM6) groups of SMs were effective at low concentration (12.5 µM-25 µM). Most of the SMs had MBC twice the MIC except, SM1, SM2, SM3 and SM11; these SMs had MBC identical to MIC (FIG. 2B, Table 1).

TABLE 1

Minimum inhibitory concentration (MIC) and minimum bactericidal concentration (MBC) of 11 selected SMs against 41 different APEC serotypes.

|  | 1 | 2 | 3 | 4 | 5 | 6 |
|---|---|---|---|---|---|---|
| O78 | 200/200 | 100/100 | 100/100 | 25/50 | 12.5/25 | 12.5/25 |
| O1 | 200/250 | 200/250 | 100/200 | 25/50 | 12.5/12.5 | 12.5/25 |
| O2 | 200/200 | 200/250 | 100/200 | 25/50 | 12.5/25 | 25/25 |
| O8 | 200/200 | 100/200 | 100/100 | 25/25 | 12.5/12.5 | 12.5/12.5 |
| O15 | 200/250 | 100/100 | 100/100 | 25/25 | 12.5/12.5 | 12.5/25 |
| O18 | 200/200 | 100/200 | 100/100 | 25/50 | 12.5/12.5 | 12.5/25 |
| O35 | 200/200 | 100/200 | 100/200 | 25/25 | 12.5/12.5 | 12.5/25 |
| O115 | 200/200 | 200/200 | 100/100 | 25/25 | 12.5/12.5 | 12.5/25 |
| O109 | 200/200 | 100/200 | 100/200 | 25/25 | 12.5/12.5 | 12.5/12.5 |
| O78-53 | 200/200 | 100/200 | 100/100 | 25/50 | 12.5/12.5 | 12.5/25 |
| O1-63 | 200/250 | 200/250 | 200/200 | 25/50 | 12.5/25 | 12.5/25 |
| O2-211 | 200/200 | 100/100 | 100/100 | 25/25 | 12.5/12.5 | 12.5/12.5 |

|  | 7 | 8 | 9 | 10 | 11 |
|---|---|---|---|---|---|
| O78 | 25/50 | 12.5/25 | 25/50 | 25/50 | 100/100 |
| O1 | 50/100 | 12.5/25 | 25/50 | 25/25 | 100/100 |
| O2 | 25/50 | 25/50 | 25/50 | 25/50 | 100/200 |
| O8 | 100/200 | 25/100 | 25/50 | 50/50 | 200/200 |
| O15 | 50/50 | 12.5/50 | 25/100 | 50/100 | 100/100 |
| O18 | 50/100 | 12.5/50 | 25/100 | 25/100 | 200/200 |
| O35 | 25/50 | 12.5/50 | 25/50 | 25/50 | 100/200 |
| O115 | 100/100 | 12.5/50 | 25/50 | 25/50 | 200/200 |
| O109 | 100/100 | 12.5/25 | 25/50 | 25/50 | 200/200 |
| O78-53 | 50/50 | 12.5/25 | 25/25 | 25/50 | 100/200 |
| O1-63 | 50/100 | 25/50 | 50/100 | 50/100 | 100/200 |
| O2-211 | 50/50 | 12.5/12.5 | 25/25 | 25/50 | 100/200 |

Figure 2C:
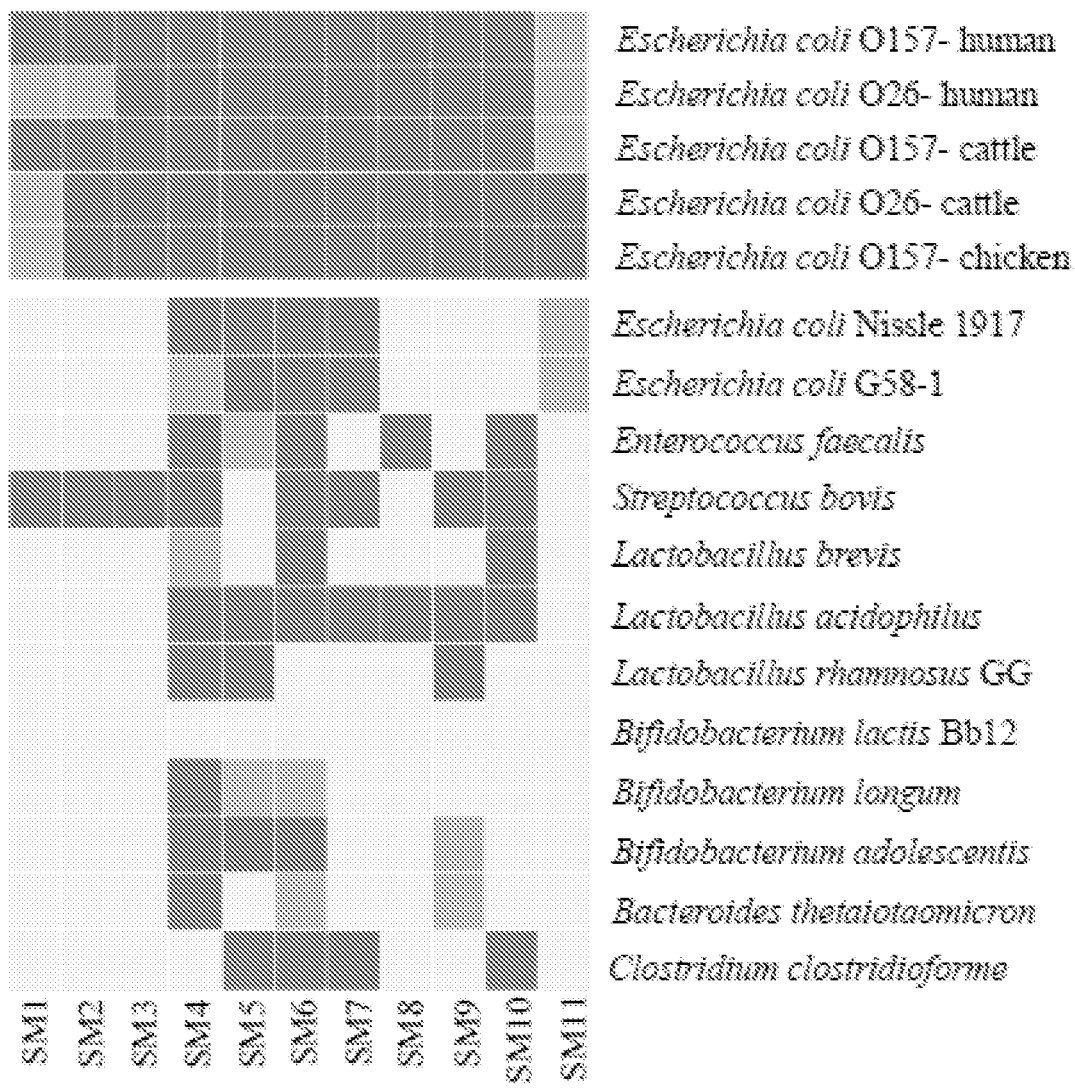
FIG. 2C is a heat map displaying the effect of 11 cidal SMs to STEC strains and commensal/beneficial microbes. SMs were tested at 100 μM. Red box indicates the cidal activity; orange box indicates the static activity, and yellow box indicates no effect of SMs against tested bacteria.

SMs are effective against multiple APEC serotypes, antimicrobial resistant APECs, and STEC strains. Anti-APEC therapeutics with broad APEC activity is desirable due to multiple and genetically heterogeneous APEC serotypes implicated in field infections. All 11 SMs inhibited the growth of all tested APEC serotypes, with MIC & MBC mostly equivalent to those of APEC O78 (FIG. 2A, 2B, Table 1). The APEC serotypes tested were resistant to TET (O1, O1-63, O2, O2-211, O8, O15, O78, O78-53), AMP (O78, O1, O2, O109, O115), CST (O1-63, O2-211), and CIP (O18) (Table 2). Antimicrobial therapeutics with efficacy against multi-antibiotic resistant pathogens is crucial to combat antimicrobial resistance. The antimicrobial efficacies of 11 SMs are equivalent between the susceptible and resistant APEC serotypes (FIG. 2A, 2B, Table 1). This indicated that these SMs could be applicable to control APEC serotypes that are resistant to antimicrobials that are currently used to treat APEC infections in poultry. All 11 SMs were inhibitory at 100 µM against STEC O157 and O26 strains isolated from different sources (FIG. 2C). Most of the SMs (SM3-SM10) were bactericidal at 100 µM for these STEC strains; however, SM1, SM2, and SM11 were not cidal at 100 µM (FIG. 2C). STEC strains are associated with human illnesses and are a public health concern. These results suggest potential applicability of these SMs to manage the *E. coli* related foodborne zoonosis.

TABLE 2A

Antimicrobial susceptibility profiles of APEC serotypes.

| | MIC (µg/mL) | | | |
|---|---|---|---|---|
| | Ampicillin | Ciprofloxacin | Colistin | Tetracycline |
| O78 | >64 (R) | 0.125 | 0.25 | 32 (R) |
| O1 | >64 (R) | <0.03125 | 0.5 | >64 (R) |
| O2 | >64 (R) | <0.03125 | 0.5 | >64 (R) |
| O8 | 4 | <0.03125 | 1 | >64 (R) |
| O15 | 2 | <0.03125 | 1 | >64 (R) |
| O18 | 4 | 4 (R) | 1 | 2 |
| O35 | 2 | <0.03125 | 1 | 1 |
| O109 | >64 (R) | <0.03125 | 0.5 | 1 |
| O115 | >64 (R) | <0.03125 | 1 | >64 (R) |
| O78-53 | 4 | <0.03125 | 0.5 | >64 (R) |
| O1-63 | 4 | <0.03125 | 4 (R) | 16 (R) |
| O2-211 | 4 | <0.03125 | 4 (R) | >64 (R) |

Six SMs affected limited number of commensals/probiotics bacteria. The use of non-specific and broad spectrum antimicrobials have effect on beneficial microbes leading to the disturbance of microbiota which renders host susceptible to infections by pathogens. Six of these SMs (SM1-SM3, SM8, SM9, and SM11) exerted least effect on beneficial microbes; having cidal activity against one to three of the 12 commensals/probiotics bacteria tested at 100 µM (FIG. 2C). Whereas, three SMs (SM4-SM6) belonging to imidazoles group were bactericidal to most of the tested probiotics/commensals. Even though piperidines (SM1, SM11) and pyrrolidinyls (SM2, SM3) group of SMs possessed higher MICs than other SMs, they displayed more specific activity against APEC. Interestingly, most of the SMs (SM1-SM3, SM8, SM9, and SM10) did not have effect on *E. coli* Nissle 1917 and *E. coli* G58-1 and none of the SMs exerted effect on *Bifidobacterium lactis* Bb12 (FIG. 2C). Overall, *Lactobacillus brevis*, *Lactobacillus rhamnosus* GG, *Bifidobacterium lactis* Bb12, and *Bacteroides thetaiotaomicron* are the microbes least affected by these SMs.

Nine SMs eradicated biofilm embedded APEC. Bacterial biofilms confers increased resistance to antimicrobials thus it is difficult to treat biofilms protected bacteria. Of 11 selected SMs, nine (SM1-SM7, SM9, and SM11) SMs possessed MBEC ranging 0.5× to 4×MIC in MBEC HTP assay (Table 2). Imidazoles (SM4-SM6) and pyrrolidinyls (SM2, SM3, and SM7) SMs were effective in eradicating biofilm embedded APEC bacteria at 0.5×MIC to 2×MIC. SM1 and SM11 possessed MBEC of 4×MIC. SM8 and SM10 significantly (P<0.05) reduced the biofilms embedded APEC at 1×MIC (data not shown); however, they were not able to eradicate biofilm embedded APEC even at 8×MIC.

significantly (P<0.05) increased the uptake of crystal violet (CV) ranging 3%-62% (FIG. 3D) except, SM4 (P=0.07). CV

TABLE 2B

Effect of 11 cidal SMs against biofilm embedded and intracellular APEC bacteria.

| | MBEC† | SMs intracellular APEC clearance concentration‡ (μM) | | | | | | | | |
|---|---|---|---|---|---|---|---|---|---|---|
| | | O78 | | | O2 | | | O1 | | |
| | (μM) | Caco-2 | HD11 | THP-1 | Caco-2 | HD11 | THP-1 | Caco-2 | HD11 | THP-1 |
| SM1 | 400$^d$ | 200$^a$ | 200$^a$ | 200$^a$ | >400 | 200$^a$ | 200$^a$ | >400 | 400$^b$ | 400$^b$ |
| SM2 | 50$^b$ | 100$^a$ | 100$^a$ | 100$^a$ | >200 | 200$^b$ | 100$^a$ | >200 | 200$^b$ | 200$^b$ |
| SM3 | 50$^b$ | 100$^a$ | 100$^a$ | 100$^a$ | >200 | 200$^b$ | 100$^a$ | >200 | 200$^b$ | 200$^b$ |
| SM4 | 25$^a$ | 50$^b$ | 50$^b$ | 50$^b$ | 100$^c$ | 50$^b$ | 100$^c$ | 100$^c$ | 50$^b$ | >100 |
| SM5 | 25$^c$ | 50$^c$ | 50$^c$ | 50$^c$ | 100$^d$ | 50$^c$ | 50$^c$ | 100$^d$ | 100$^d$ | 100$^d$ |
| SM6 | 12.5$^a$ | 50$^c$ | 50$^c$ | 50$^c$ | 100$^d$ | 50$^c$ | 50$^c$ | 100$^d$ | 100$^d$ | 100$^d$ |
| SM7 | 50$^b$ | 100$^c$ | 50$^b$ | 50$^b$ | 100$^c$ | 100$^c$ | 25$^c$ | 100$^c$ | 100$^c$ | >100 |
| SM8 | >100 | 50$^c$ | 50$^c$ | 50$^c$ | 50$^c$ | 50$^c$ | 50$^c$ | 50$^c$ | 50$^c$ | 50$^c$ |
| SM9 | 50$^b$ | 50$^b$ | 100$^c$ | 50$^b$ | 100$^c$ | 100$^c$ | 50$^b$ | 100$^c$ | 100$^c$ | 50$^b$ |
| SM10 | >200 | 100$^c$ | 50$^b$ | 100$^c$ | 100$^c$ | 100$^c$ | 50$^b$ | 100$^c$ | >100 | >100 |
| SM11 | 400$^d$ | 100$^a$ | 100$^a$ | 100$^a$ | 200$^b$ | 200$^b$ | 100$^a$ | >200 | 200$^b$ | >200 |

†SMs MBEC;
$^a$0.5X MIC,
$^b$1X MIC,
$^c$2X MIC,
$^d$4X MIC.
‡SMs intracellular APEC clearance concentration;
$^a$1X MIC,
$^b$2X MIC,
$^c$4X MIC,
$^d$>4XMIC.
SMs MBEC and intracellular APEC clearance concentration with ">" arrow indicates SMs not able to eradicate completely the biofilm embedded APEC bacteria or SMs not able to completely clear intracellular APEC up to the concentrations tested.

No resistance was detected in APEC O78 to SMs. Identical MBCs were observed when APEC O78 was grown in sub-lethal (0.75×MIC) doses of SMs in liquid media for 15 overnight passages (90 generations). After 15 days of incubation of APEC O78 on solid media amended with a 2×MBC of SMs, no resistant colonies were observed. These results suggest that the 11 SMs were less likely to induce resistance in APEC O78; however, more in-depth characterization of resistance is needed for future development and application of these SMs in the field.

Figure 3A:
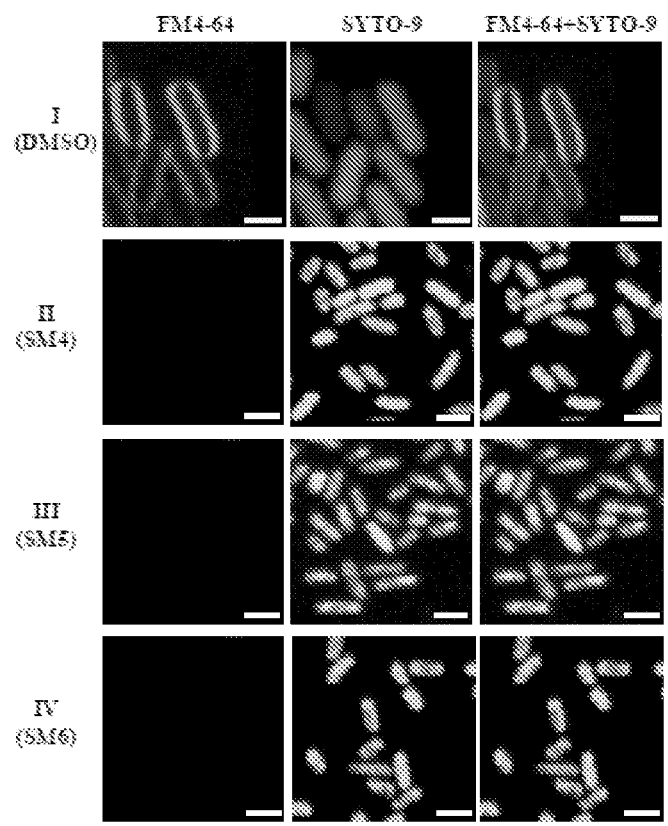
FIG. 3A shows confocal microscopy images of SMs treated APEC bacteria. Logarithmic phase grown APEC O78 cultures were treated with 2×MBC of SMs followed by the staining with FM4-64 (membrane stain; red colored) and SYTO-9 (nucleic acid stain; green colored). (Panel I) DMSO treated APEC bacteria showing stained membrane and nucleic acid, (Panels II-IV) SM4, SM5, and SM6 showing absence of FM4-64 stained membrane (membrane disruptors)
Figure 3B:
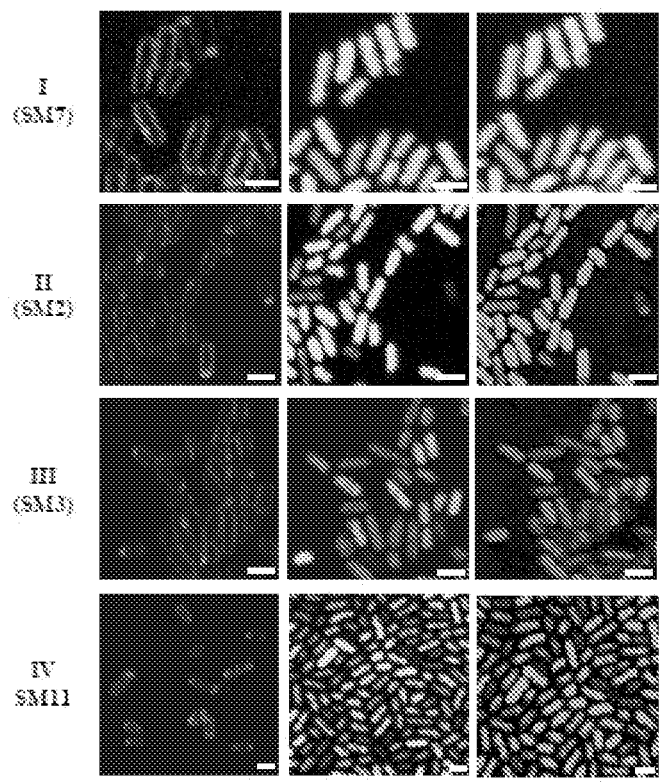
FIG. 3B shows confocal microscopy images of SMs treated APEC bacteria. Logarithmic phase grown APEC O78 cultures were treated with 2×MBC of SMs followed by the staining with FM4-64 (membrane stain; red colored) and SYTO-9 (nucleic acid stain; green colored). (Panels I-IV) SM7, SM2, SM3, and SM11 showing bright red foci at random positions throughout the cell indicating membrane defects (membrane pore formers)
Figure 3C:
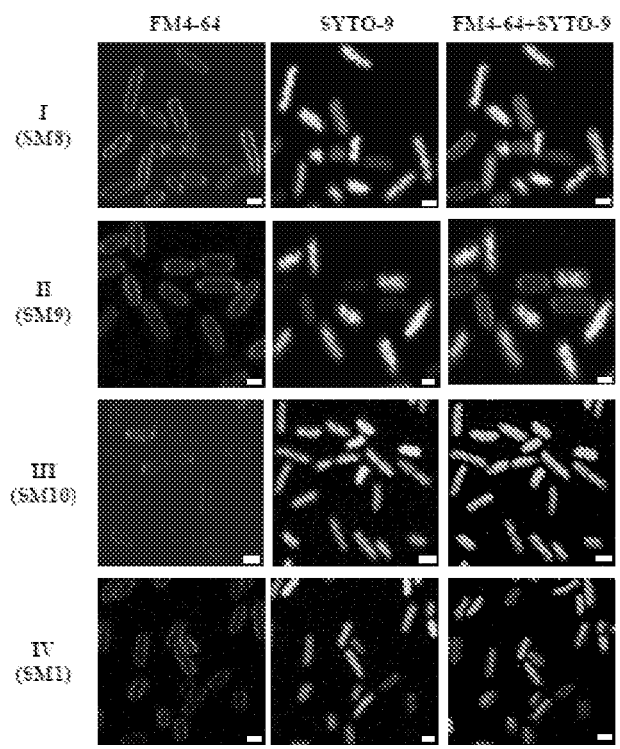
FIG. 3C shows confocal microscopy images of SMs treated APEC bacteria. Logarithmic phase grown APEC O78 cultures were treated with 2×MBC of SMs followed by the staining with FM4-64 (membrane stain; red colored) and SYTO-9 (nucleic acid stain; green colored). (Panels I-IV) SM8, SM9, SM10, and SM1 showing filamentous or short rods (spheroplasts) morphology (PG synthesis inhibitors). Bars: 1 μM.

SMs exhibited antimicrobial activity by affecting APEC cell membrane. BCP is regarded as a rapid and powerful approach to identify the cellular pathways affected by different antibacterials based on the cytological changes induced by SMs. This study suggests that the 11 cidal SMs are likely to functions by either disrupting cell membranes or producing membrane defects or inhibiting cell wall peptidoglycan (PG) synthesis (FIGS. 3A-3C). DMSO treated APEC bacteria showed stained membrane and nucleic acid (FIG. 3A, Panel I). Imidazoles SMs (SM4-SM6) are likely to disrupt the cell membrane which is similar to polymixins mechanism of action (MOA) and is evident by the absence of FM4-64 stained bacterial cell membrane (FIG. 3A, Panels II-IV). Pyrrolidinyls SMs (SM2, SM3, and SM7) and SM11 are likely to produce membrane defects by forming pores as similar to those induced by daptomycin and macrocyclic peptide JB-95 MOA which is evident by the presence of FM4-64 stained bright foci or protrusions at random positions on the cell (FIG. 3B, Panels I-IV). Quinolines SMs (SM8 and SM9) along with SM1 and SM10 produced either filamentous or short rods (spheroplasts) morphology (FIG. 3C, Panels I-IV) of APEC which is similar to ampicillin and cephalexin antibiotics, these antibiotics inhibit the synthesis of cell wall PG.

Membrane permeability assays revealed SMs affecting the cell membrane integrity. SMs as well as EDTA treatment can penetrate the cells with altered membrane permeability. SMs and EDTA treatment also significantly (P<0.05) increased the 260 or 280 nm absorbing materials in the treated supernatants in comparison to DMSO treatment (Table 3). Intracellular constituents such as DNA, RNA, proteins can be leaked through permeable membrane.

Figure 4:
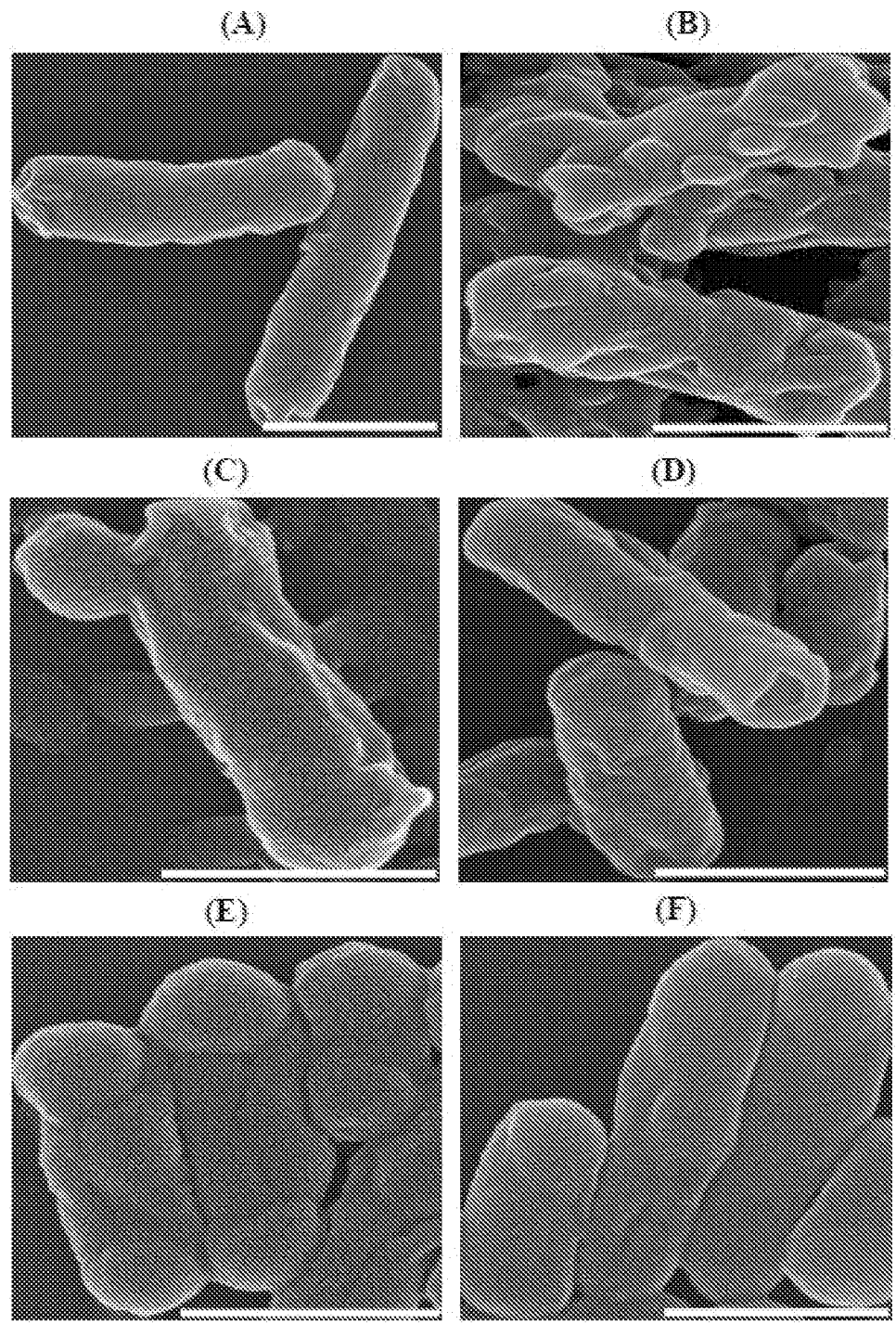
FIG. 4 shows representative SEM images of SMs treated APEC bacteria. (Panel A) DMSO treated bacteria showing less wrinkled smooth surface cell measuring 1-2 μM, (Panel B) SM4—showing severe wrinkling and multiple blebbing throughout the cell (membrane disruptors), (Panels C & D) SM3 and SM7—showing blebbing or pore at single cell pole, respectively (membrane pore formers), (Panels E & F) SM8 and SM10—showing shortened cells (~0.5 μM) and blebbing at cell poles (PG synthesis inhibitors). Bars: 1 μM.

SEM results further supported the cell membrane affecting mode of action of SMs. SEM images suggest that SMs treatment produced membrane wrinkling, blebbing/vesicle-like structures, and pores (FIG. 4) which are the characteristics morphology induced by membranes acting antibiotics and several other antimicrobial agents. DMSO treated APEC bacteria showed very few wrinkled smooth surfaced cells measuring 1-2 μM (FIG. 4, Panel A). The frequency and sites of blebbing and severity of wrinkling differed between the SM treatments. SM6 (FIG. 4, Panel B) produced more severe wrinkling and multiple blebbing throughout the cells. SM3 and SM7 formed blebbing and pore at single cell pole, respectively (FIG. 4, Panels C and D). SM8 and SM10 produced distinct morphology than other SMs with shortened cells (~0.5 μM) and blebbing at both cell poles (FIG. 4, Panels E and F) which is similar to ampicillin induced cells morphology.

TABLE 3

SMs treatment induced leakage of 260 and 280 nm absorbing material.

| | Absorbance (nm) | |
|---|---|---|
| | 260 | 280 |
| SM1 | 4.00* | 3.08* |
| SM2 | 3.71 | 2.86* |
| SM3 | 3.77 | 2.84* |
| SM4 | 3.91* | 2.69* |
| SM5 | 4.00* | 2.67* |

TABLE 3-continued

SMs treatment induced leakage of 260
and 280 nm absorbing material.

| | Absorbance (nm) | |
|---|---|---|
| | 260 | 280 |
| SM6 | 3.99* | 2.69* |
| SM7 | 3.91* | 2.70* |
| SM8 | 4.00* | 2.82* |
| SM9 | 3.99* | 2.78* |
| SM10 | 3.98* | 2.73* |
| SM11 | 4.00* | 2.89* |
| EDTA | 4.00* | 2.60 |
| DMSO | 3.77 | 2.58 |

SMs treatment induced OD increment was compared with DMSO treatment.
*P < 0.05.

SMs exhibited minimal toxicity to chicken and human cells. Based on LDH assay, most of the SMs possessed least cytotoxicity (<10%) on Caco-2 (FIG. 5A) and HD11 cells (FIG. 5B) except SM11. Among 11 cidal SMs, four SMs (SM4-SM6, and SM11) caused hemolysis (20%-60%) to RBCs (FIG. 5C) while the rest of the SMs displayed <10% of hemolysis.

SMs reduced intracellular APEC in phagocytic and non-phagocytic cells. The fimbria mediated initial APEC adhesion and OmpA, IbeA mediated invasion into the cells facilitate APEC to survive intracellularly in phagocytic and non-phagocytic cells of the host and is an important aspect of APEC pathogenesis. Therefore, the administered antimicrobial therapeutics must be able to permeate and act inside the APEC infected cells. After 6 h of treatment, SMs significantly (P<0.01) reduced intracellular APEC O78, O2, and O1 in infected Caco-2, HD11, and THP1 cells at varying concentrations (0.5×-2×MIC) with maximal reduction (3-5 log; 100% clearance) of intracellular APEC O78, O2 and O1 at concentration less than or equal to 4×MIC (Table 2) except, SM5 and SM6. SM5 and SM6 possess very high Log P (SM5: 8.75, SM6: 10.19) compared to other SMs; high Log P values cause poor permeation and absorption of drugs through the membranes. Among 11 SMs, SM4-SM10 were effective in clearing intracellular APEC O78, O2, and O1 at concentration less than or equal to 100 µM for most of the cases; whereas, SM1-SM3 and SM11 were effective only at concentration equal or above 100 µM (Table 2). Interestingly, higher concentrations of SMs were needed to clear intracellular APEC O1 followed by O2 and O78 (Table 2) which may be due to greater invasion and survival of O1 serotype inside the cells. The serotype O1 is reported to carry IbeA (invasin) and Iss (increased serum survival) gene more frequently compared to O78 and O2 which might contribute for better invasion and survival. SM8 was the most effective SM in clearing intracellular APEC with complete clearance at concentration less than or equal to 50 µM (Table 2). Overall, SM4, SM7, SM8, SM9, and SM10 were the most effective SMs in clearing intracellular APEC serotypes in all tested cells.

Figure 6A:
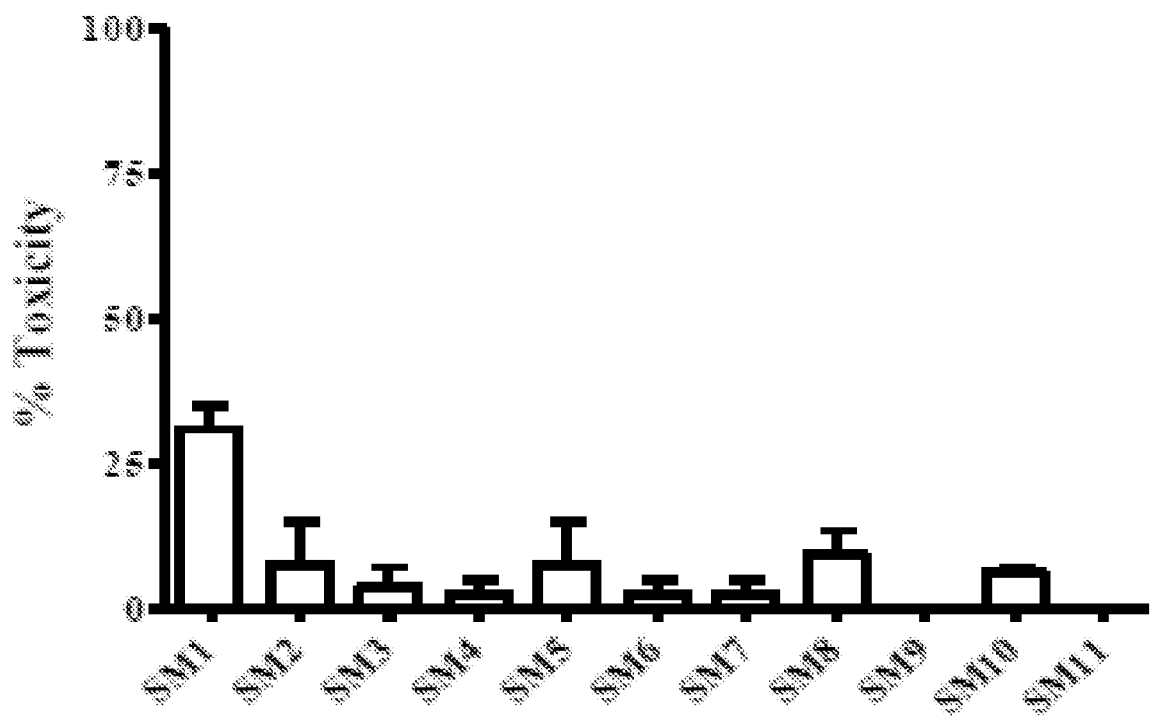
FIG. 6A is a plot showing the toxicity of SMs to wax moth (G. mellonella) larvae (n=20). SMs were injected to larvae (12.5 μg/larva) and larval survival was monitored for 72 h.

SMs were least toxic to wax moth larvae, extended the larval survival, and reduced the APEC load inside the larvae. The wax moth larval model can be as an alternative to mammalian model to study bacterial pathogenesis and antimicrobial drug testing. Except SM1, rest of the SMs were least toxic (<10%) to larvae (FIG. 6A).

Figure 6B:
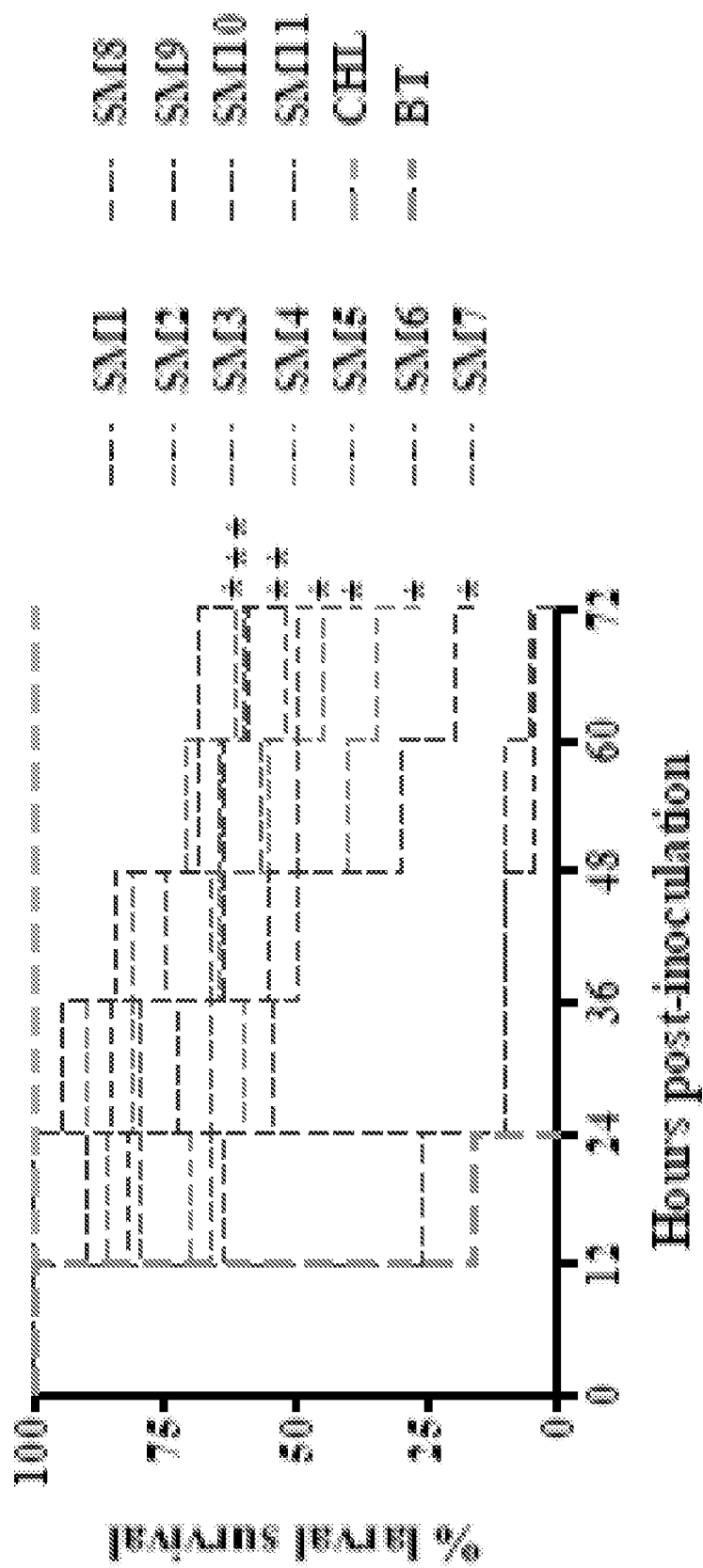
FIG. 6B is a plot showing the Kaplan-Meir survival curves of APEC infected larvae treated with SMs (12.5 μg/larva). Larvae (n=20) were injected with SMs 2 h before infection with the Rif' APEC O78 and larval survival was monitored for 72 h. Survival curves of SMs treated larvae were compared with buffer mix treated larvae. *P<0.05.
Figure 6C:
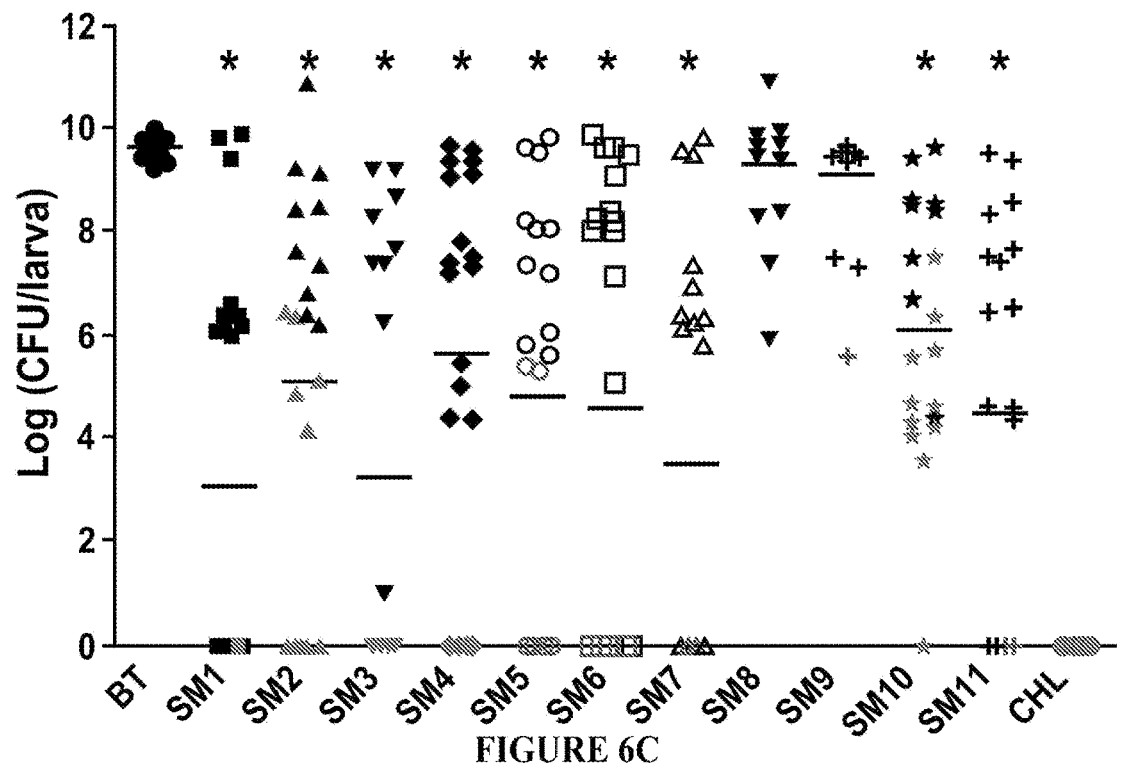
FIG. 6C is a scatter plot displaying APEC load in SMs treated larvae. APEC load was quantified from dead larvae (blue symbols) collected every 12 h and live larvae (red symbols) collected at 72 h post-infection. APEC load of SMs treated larvae were compared with buffer mix treated larvae. *P<0.05. BT—buffer mix treated; CHL—chloramphenicol treated.

Most of the SMs (SM1-SM7, and SM10-SM11) significantly extended the survival of infected larvae (FIG. 6B). The larva survival rate was significantly increased in the SM treated groups compared to the DMSO treated group. In the treated groups, 15-55% of infected larvae survived even at 72 h post-infection, while all larvae injected with DMSO (control) died by 24 h. All of the SMs which extend the survival of infected larvae also significantly (P<0.05) reduced the APEC load (3-6 log) inside the larvae (FIG. 6C). Live larvae had significantly low (P<0.01) APEC load (1 log on an average) in comparison to dead larvae (7 log on an average) which also correlated with the survival of the larvae (r=0.7).

Figure 7A:
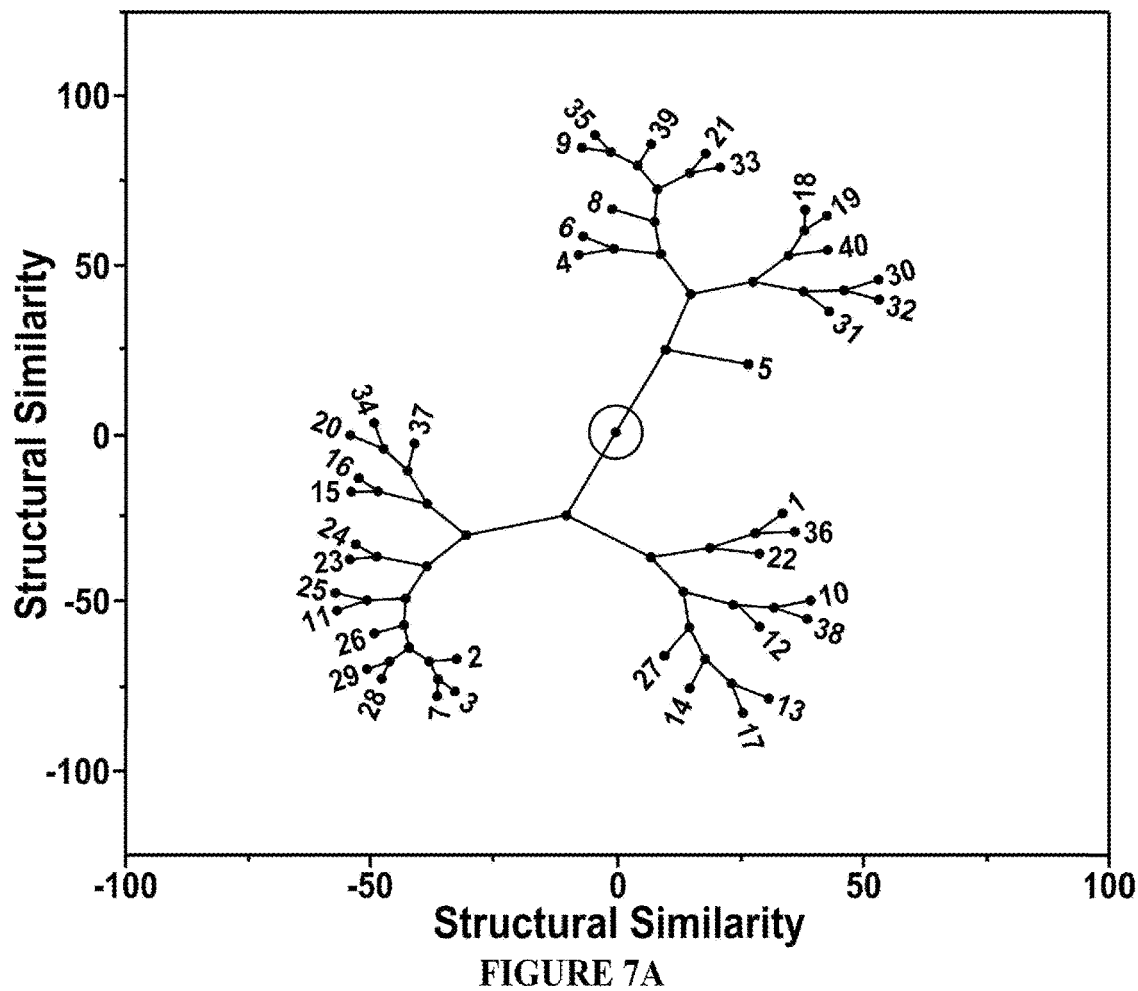
FIG. 7A shows a constellation plot depicting structural clustering (2D) of 40 primary hits. Hits were clustered into three major clusters. The 11 selected bactericidal SMs are labelled 1-11. Structural similarity scores were retrieved from PubChem database and plot was generated using JMP software. SMs belonging to same chemical groups were mostly clustered together.
Figure 7B:
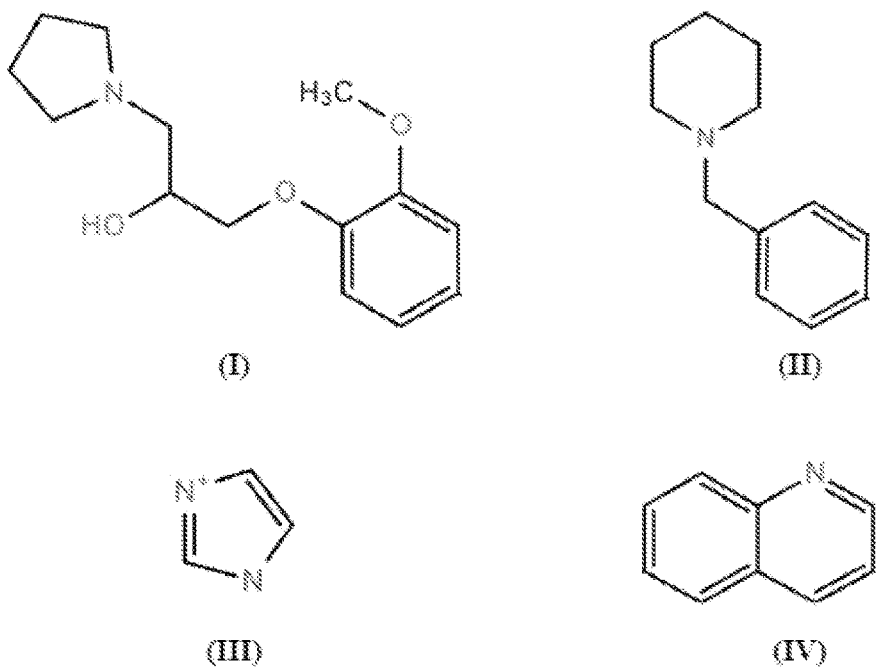
FIG. 7B shows some common scaffolds identified in anti-APEC SMs in this study. (I) pyrrolidinyl, (II) piperidine, (III) imidazole, and (IV) quinoline.

Structure-activity relationship analysis. Structural clustering showed imidazole (SM4-SM6) and quinoline (SM8, SM9) SMs structurally more closer and also possesses nitrogen-containing aromatic ring in common which could contribute for their lower MIC and MBC in comparison to piperidine and pyrrolidinyl SMs (FIG. 7A, FIG. 1C, FIG. 2A). The SMs with additional benzene ring in the pyrrolidine scaffold showed bactericidal activity (FIG. 1C) whereas SMs without benzene ring showed only inhibitory activity. Among the bactericidal pyrrolidinyl SMs (SM2, SM3, SM7), SM7 possesses trifluoro group which could contribute its bactericidal activity at lower concentration in comparison to SM2 and SM3 (FIG. 1C). The non-bactericidal piperidine SMs (SM1, SM11) contain hydroxy-methoxy-benzyl group in their structures (not shown) in comparison to bactericidal piperidine hits (FIG. 1C). SM10 belonging to miscellaneous group contains additional trichloro group (FIG. 1C) in comparison to closest hit (FIG. 7A) which could contribute to its bactericidal activity Discussion APEC is responsible for severe economic losses to the poultry industry worldwide and is also regarded as the potential source of human ExPECs. Effective novel control methods are needed because of the limitations associated with current control methods. Anti-APEC SMs identified in this example are diverse in their structures with three major clusters based on structural similarity (FIG. 7A) and contained pyrrolidinyl, piperidine, imidazole, and quinoline scaffolds (FIG. 7B). These identified anti-APEC scaffolds could facilitate the development of antimicrobial therapeutics to control APEC infections in poultry.

The anti-APEC SMs identified in this example affect the APEC cell membrane. Bacterial cell membranes are regarded as promising targets for discovery of new antimicrobial therapeutics and to combat antimicrobial resistance. Membrane affecting antimicrobials are most likely to act by disrupting membrane architecture and functional integrity which is supported by confocal and SEM images and membrane permeability assays (FIGS. 3A-3C and FIG. 4). Under confocal microscopy, SMs treated APEC bacteria showed membrane disrupted morphology along with formation of membrane defects throughout the cell (FIG. 3A, 3B, 3C). The disruption of the cell membrane and formation of membrane defects could subsequently leads to leakage of cell contents, loss of membrane potential, and eventual cell death. Further, SEM analysis revealed that SMs treatment induced membrane wrinkling, blebbing/vesicle-like structures, and pores (FIG. 4) which consequently could impair the cell membrane integrity leading to cell death. The membrane defects caused by SMs resembles to those caused by already known membrane acting antibiotics such as polymixins (SM4-SM6), daptomycin (SM2, SM3, SM7, and SM11), ampicillin/cephalexin (SM1, SM8-SM10), and several other antimicrobial peptides. Polymixins disrupt the outer membrane integrity of Gram negative bacteria by forming the blebs on the surface of the bacterium. Daptomycin induces holes in the membrane leading to a breach in the cell membrane and subsequent cell death by forming membrane blebs. Multiple antimicrobial peptides such as Human α-defensin 5 (HD5), gramicidin S, peptidyl-glycyl-leucine-carboxyamide (PGLa), cathelicidins, lactoferricin, and human epididymis 2 (HE2) protein isoforms damage the bacterial cell membrane by forming the blebs. Peptoids, an alternative to antimicrobial peptides damage the membrane of *E. coli* by forming membrane blebs. Sericin, a soluble silk glue protein exhibits antibacterial activity against *E. coli* by inducing blebbing of the membrane.

Figure 3D:
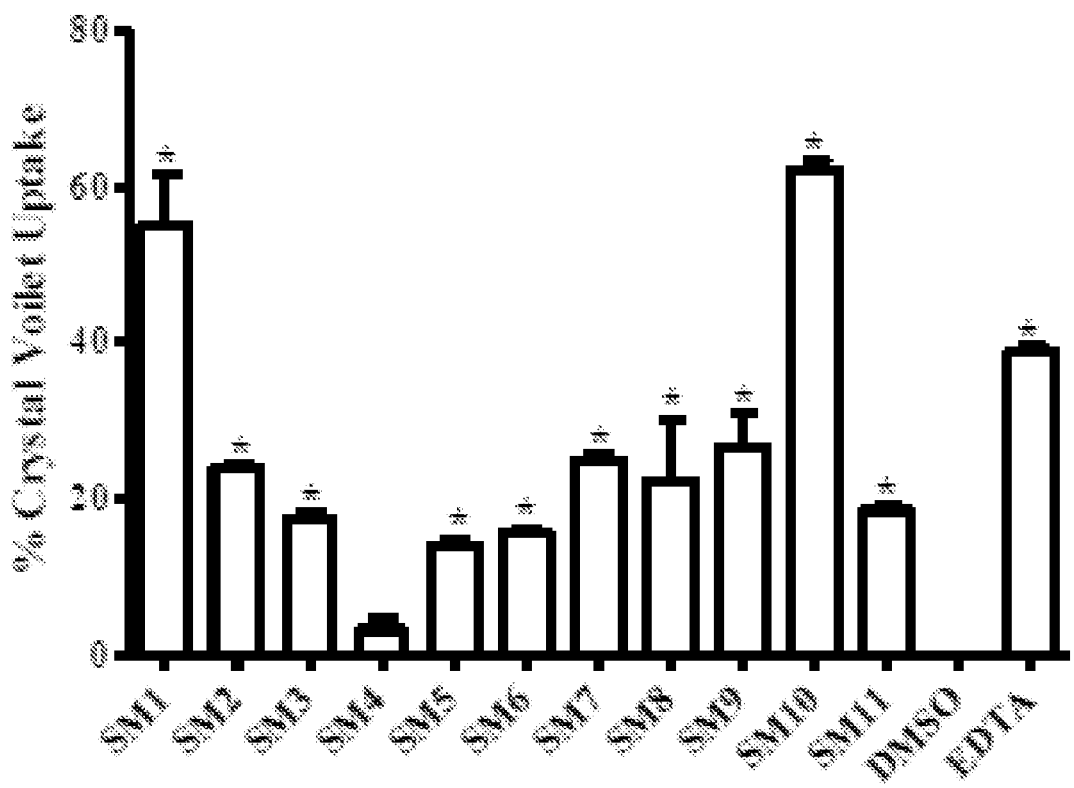
FIG. 3D show the results of a CV uptake assay. APEC O78 was treated with 2×MBC of SMs, incubated with crystal violet, and absorbance of the supernatants was measured at OD 590 nm. Uptake of CV was significantly higher in SMs treated samples compared with DMSO treated sample and was similar to EDTA treated sample.*P<0.05.

The SMs identified in this example are effective against multiple APEC strains, STEC strains as well as antimicrobials resistant strains (FIGS. 2A-2C) which might be explained by their membrane affecting mode of action. Antimicrobials that target the cell membranes exhibit broad spectrum of activity and are being used to control MDR bacteria such as ESKAPE pathogens, methicillin resistant *Staphylococcus aureus* (MRSA), thereby SMs identified in this example could be used to treat APEC infections caused by antimicrobial resistant strains. Membrane affecting antimicrobials also have a low potential for development of resistance mostly due to their effect on multiple targets. Consistent with low resistance acquisition of membrane affecting antimicrobials, no resistant APECs were isolated in vitro in our study which could makes these SMs as emergency antimicrobials in APEC outbreaks situation. Permeability of APEC cell membrane is also impaired following SMs treatment (FIG. 3D). Thus, the incorporation of these SMs in therapy could enhance the uptake or penetration of antibiotics that have intracellular targets or could interact synergistically with other membrane affecting antibiotics. In fact, several SMs significantly decreased the MBC of TET, CST, and CIP that are commonly used to treated APEC infection in poultry. As a result, combining these SMs could increase the activity of antibiotics or reduce the amount of antibiotics needed, and by consequence, could attenuate the development of antimicrobial resistance associated with APEC in poultry.

Most of the identified SMs, especially imidazoles (SM4-SM6) and pyrrolidinyls (SM2, SM3, SM7), eradicated biofilm embedded APEC even at 0.5× to 2×MIC (Table 2) which could be due to low molecular wt. of SMs which allows better penetration inside the biofilms or could be due to inherent biofilm dispersal/disruptor activity of imidazoles or anti-biofilm activity of pyrrolidinyls. Membrane affecting antimicrobials have capacity to act against slow-growing or dormant bacteria as well as on biofilms. APEC can form biofilms in poultry facilities such as in water lines and drinker systems and are difficult to eradicate by common disinfectants and antimicrobials. Therefore, the SMs identified in this example could be used to eradicate biofilm embedded APEC in poultry facilities; thereby reducing the incidence and occurrence of APEC infections in poultry farms. SM8 and SM10, which are effective against planktonic and intracellular bacteria even at low concentration (FIGS. 2A-2C, Table 2) showed decreased effectivity towards biofilm embedded APEC which could be due to restricted penetration of SMs inside the biofilm or could be due to binding with biofilm matrix. Additionally, these SMs contain chlorine atoms in common; bacterial biofilms are increasingly resistant to chlorine treatment.

Figure 5A:
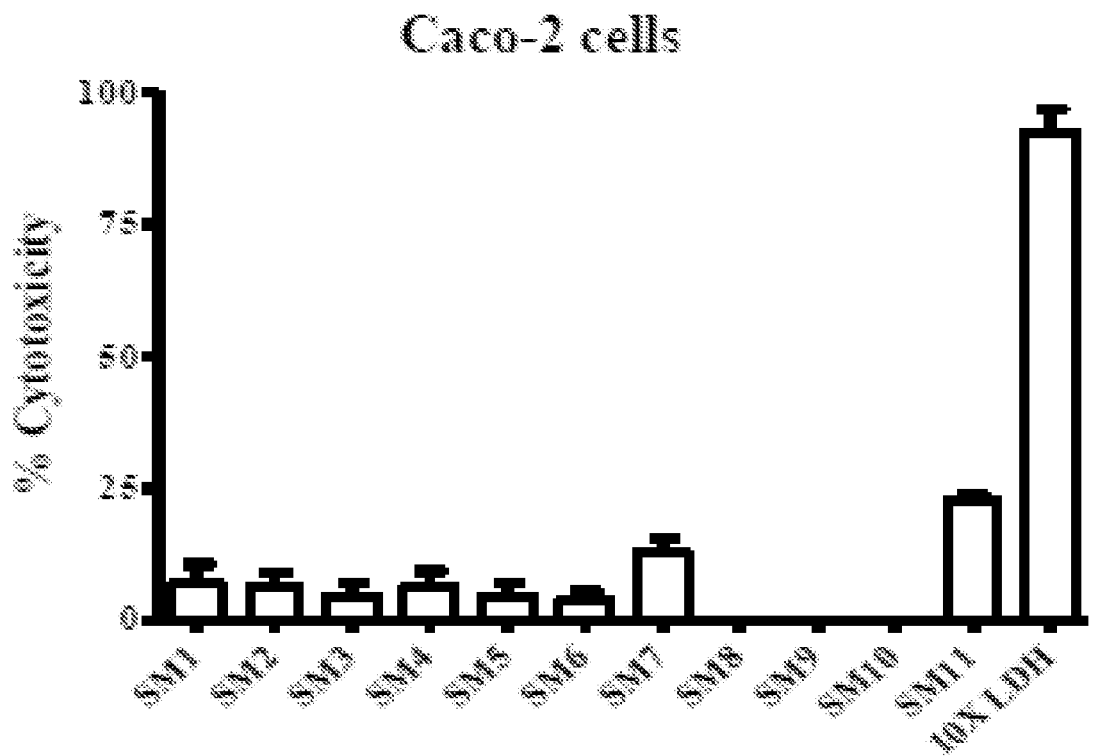
FIG. 5A is a plot showing the cytotoxicity of 11 cidal SMs to Caco-2. Toxicity was assessed by measuring the LDH released from lysed cells after incubation with 200 μM concentration of SMs for 24 h. 10×LDH was used as positive control.
Figure 5B:
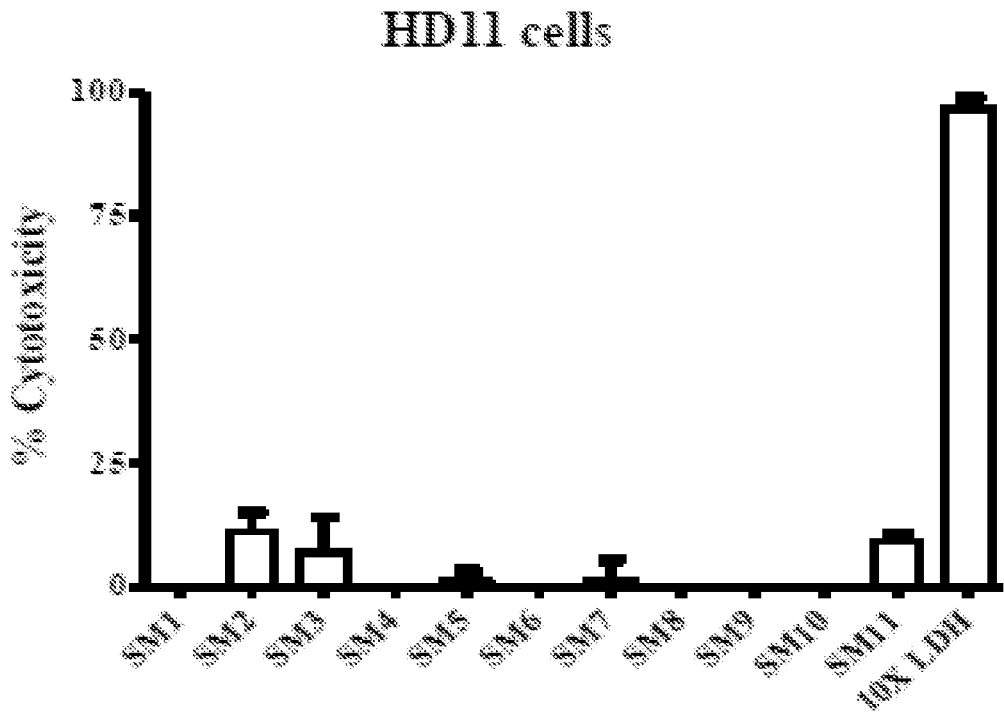
FIG. 5B is a plot showing the cytotoxicity of 11 cidal SMs to HD11 cells. Toxicity was assessed by measuring the LDH released from lysed cells after incubation with 200 μM concentration of SMs for 24 h. 10×LDH was used as positive control.
Figure 5C:
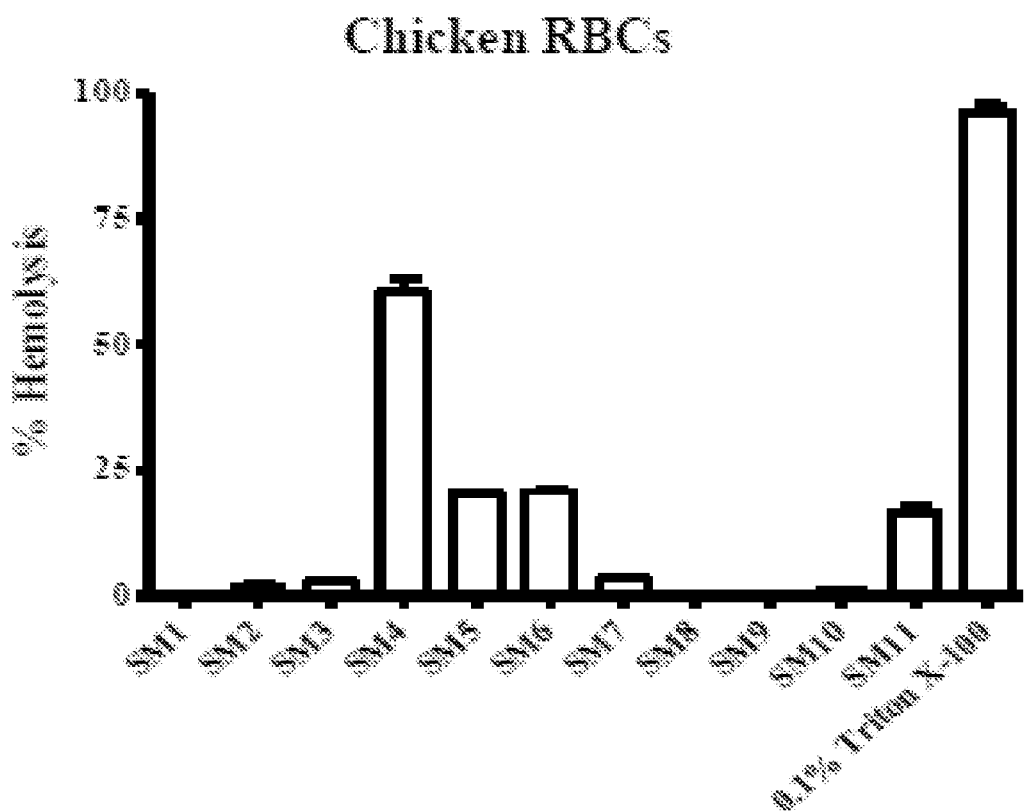
FIG. 5C shows the hemolytic activity of SMs to chicken RBCs. 10% washed RBCs were incubated with 200 μM of SMs for 1 h and the hemoglobin released from lysed RBCs was measured. 0.1% Triton X-100 was used as positive control.

Most of the identified SMs (SM1-SM3, SM7-SM10) identified were least or non-toxic to chicken and human cells (FIGS. 5A-5C). The toxicity of the membrane affecting antimicrobials depends upon the membrane organization and its lipids composition and proportion. Both epithelial and macrophage cells membrane contain phosphatidylcholine (PC) as major phospholipids; however, bacterial cell membrane is rich in phospholipids such as phosphatidylglycerol (PG), phosphatidylethanolamine (PE) and cardiolipin (CL) which makes membrane affecting antimicrobials selectively toxic to bacterial cells. RBCs also contain phosphatidylethanolamine (PE) phospholipid in their membrane similar to bacterial cell membrane; this similarity could attribute toxicity of some of the SMs (SM4-SM6, and SM11) to RBCs. The presence of cyclohexyl and/or benzodioxol groups in SM4 and SM11 could contribute for their relatively high toxicity (FIG. 1C). These SMs were however not toxic to wax moth larvae which could be due to cellular analogy of wax moth larva to mammals (epithelial cells of larva gut similar to intestinal cells of mammals). Consistent with wax moth studies, no negative impact of SM5 and SM6 on chicken health and performance was observed in our pilot experiment. Further, most of the SMs identified exerted no effect on tested Gram positive bacteria such as *Lactobacillus* and *Bifidobacterium* (FIG. 2C). The use of rich media however could attribute to lesser effect of SMs to beneficial microbes. The Gram positive and Gram negative bacteria also have different composition and relative amounts of lipids in their membranes. Gram positive bacterial genera such as *Clostridium*, *Lactobacillus*, and *Bifidobacterium* are the predominant commensals of the poultry gut microbiota. Thus, one might expect lesser impact on the microbiota of the chickens treated with these SMs. Further, LGG and Bb12, widely used probiotics are unaffected by these SMs, they could be combined with these SMs to enhance the probiotics control of APEC infections in poultry.

The treatment with most of the identified SMs cleared the intracellular APEC in the infected phagocytic and non-phagocytic cells (Table 2); similar effect to the host cells could help to ameliorate APEC pathogenicity. Consistent with the SMs intracellular clearance of APEC, SM1-SM3, SM4-SM6, SM7, SM10, and SM11 treatment significantly reduced the APEC load inside the wax moth larvae. The lesser efficacies of SM8 and SM9 in wax moth larvae in comparison to cultured epithelial and macrophage cells could be due to interaction with host immune components of wax moth larvae such as antimicrobial peptides or due to production of drug degradative enzymes. Wax moth larvae possess complex innate immune system similar to mammals and several studies including studies in ExPEC, have reported the similar results between wax moth and mammalian models. Besides, wax moth larval model has been frequently used to evaluate the efficacy and toxicity of antimicrobial agents. Therefore, the efficacy of these SMs in cultured infected cells and wax moth larvae may suggest their therapeutic efficacy in chickens.

In conclusion, this example identified seven novel effective and safe (two foremost parameters of any therapeutic drug) SMs (SM3, SM5-SM10) as potential anti-APEC therapeutics. These SMs function through affecting APEC cell membrane and can also be combined with other anti-APEC strategies such as antibiotics and probiotics. Our future studies will focus on testing SMs efficacy in chickens, identifying SMs molecular targets to define their modes of action, and also to develop these SMs to control *E. coli* related foodborne zoonosis including APEC related ExPEC infections in humans.

Example 2. Novel Small Molecule Modulators of Avian Pathogenic *Escherichia coli* Quorum Sensing Colibacillosis caused by avian pathogenic *E. coli* (APEC), a subgroup of extra intestinal *E. coli* (ExPEC), is an economically important bacterial disease of poultry. Poultry products contaminated with APEC are also considered potential sources of foodborne ExPEC to humans. Currently, APEC infections in poultry are controlled by antibiotics or vaccination; however, their effect is limited due to the infection with antibiotic resistant strains and heterologous serotypes. Therefore, there is a critical need for identifying novel approaches to effectively control APEC infections in chickens. In this example, using the bioluminescent autoinducer 2 (AI-2) indicator *Vibrio harveyi* BB170, the cell free culture supernatant of APEC O78, prepared from cultures grown in the presence of 4,182 small molecules (SMs: 100 M), was screened. A total of 69 SMs inhibited more than 75% of APEC O78 AI-2 activity in the indicator bacteria. Ten that showed highest AI-2 inhibition were selected for further studies. Most of these SMs inhibited the AI-2 activity of other APEC serotypes and significantly reduced APEC O78 biofilm formation and motility. Most compounds showed minimal toxicity on human intestinal cells (Caco-2), chicken macrophage (HD-11), and chicken and sheep red blood cells, and reduced APEC survival in HD-11 and THP-1 human macrophages. In vivo wax moth larval model also revealed no or minimal toxicity and protection against APEC challenge. These SMs affected the expression of APEC O78 QS, virulence, biofilm and motility associated genes providing insight on their potential mode of action. Further testing in chickens will facilitate development of these SMs as novel therapeutics to augment APEC control in poultry and thus also reduce human ExPEC infections.

Introduction

Colibacillosis caused by avian pathogenic *E. coli* (APEC) is a significant bacterial disease of poultry worldwide. Avian pathogenic *E. coli* belongs to a subgroup of extra-intestinal Pathogenic *Escherichia coli* (ExPEC). APEC can be transmitted to humans through consumption of contaminated poultry and fresh produce fertilized with contaminated poultry litter. Additionally, poultry ExPEC share many important traits with human ExPEC including antimicrobial resistance patterns, resistance genes, and virulence factors, thus APEC pose a potential zoonotic risk for humans. Even though there are several APEC serotypes implicated in avian collibacillosis, the most predominant serotypes associated with avian colibacillosis are O1: K1, O2: K1, and O78: K80.

Because poultry serve as the main host for APEC, there is potential for zoonotic transmission where humans may become infected with APEC through consumption of undercooked poultry. Raw produce that was fertilized with poultry litter. Because poultry serve as the main host for APEC, there is potential for zoonotic transmission where humans may become infected with APEC through consumption of undercooked poultry. Raw produce that was fertilized with poultry litter.

Avian colibacillosis is characterized by yolk sac infection, swollen-head syndrome, septicemia, and inflammation of different organs such as pericarditis, perihepatitis, airsacculitis, salpingitis, artheritis, and peritonitis. APEC infects all ages of commercial poultry and can also negatively affect weight gain and feed conversion. Additionally, APEC infection is associated with high morbidity and mortality and carcass condemnation, leading to significant economic losses to the poultry industry.

Currently, APEC infections in poultry are controlled by a commercially available modified-live vaccine (Poulvac *E. coli*). However, the vaccination does not provide complete protection against all APEC serotypes and high mortality in vaccinated broilers due to virulent APEC infections has been reported. In addition, antimicrobials such as cephalosporins, tetracyclines, and quinolones are used to treat APEC infections and they also have limited effect due to the emergence of antimicrobial resistance strains. Thus, there is a need for identifying novel approaches to enhance the control of APEC infections in poultry.

APEC possess several virulence factors that have been determined to be involved in different stages of infection process and pathogenesis such as type 1, AC/1, and Stg fimbriae, type IV pili, and curli associated with colonization, IbeA, Tia associated with invasion, multiple iron acquisition system (aerobactin, salmochelin, SitABCD, heme utilization/transport protein ChuA), serum resistance traits (TraT, Iss, LPS, K1 capsule), antiphagocytic activity (O and K antigens, SitABCD), temperature-sensitive hemagglutinin gene (tsh), hemolysin E (hlyE), outer membrane proteins A (ompA), and vacuolating autotransporter toxin gene (vat). Pathogenicity of APEC is also regulated by quorum sensing (QS) systems. The QS is a mechanism of bacterial cell-to-cell communication that involves the production, release and detection of extracellular signaling molecules called autoinducers (AIs). The QS Autoinducer-2 signal molecule (AI-2) allows interspecies communication and regulates expression of genes that are involved in various processes including virulence factors secretion, biofilm formation, motility, genetic competence, sporulation, and antibiotic production. Furthermore, the luxS gene, which mediates the synthesis of AI-2 has also been shown to regulate motility, biofilm formation, virulence and pathogenesis of many bacterial pathogens including APEC. Therefore, inhibition of luxS and/or AI-2 activity using QS small molecule inhibitors (QSI) can be a potential strategy for novel antibacterial development. As the QSI do not interfere with the metabolic processes of a bacterial cell such as protein synthesis, DNA metabolism, cell wall formation which are the targets for the development of drug resistance, they do not exert selection pressure on the bacteria during treatment, thus bacteria are less likely to develop resistance.

*Vibrio harveyi*, a marine Gram-negative bioluminescent bacterium, regulates luminescence through QS and exists in high population densities in association with other bacterial species. *V. harveyi* regulates bioluminescence via two-component signaling systems, AI-1 and AI-2, each is composed of a sensor-autoinducer pair. *V. harveyi* indicator strains are capable of detecting AI-2 of many bacteria that produce similar AI-2 molecules and stimulate light production following the addition of cell-free culture supernatant from these nonluminous bacteria. For example, *E. coli, Salmonella typhimurium, Pseudomonas aeruginosa*, and *Vibrio cholera*, AI-2 producing bacteria, have been reported to produce signaling substance that stimulates bioluminescence production in *V. harveyi*.

In this example, *V. harveyi* BB170 AI-2 was used as an indicator bacteria (AI-1V and AI-2-) to identify small molecule AI-2 inhibitors of APEC. The selected AI-2 inhibitors were tested in vitro for their; toxicity on human intestinal cells, chicken macrophage cells, chicken and sheep red blood cells (RBCs) and efficacy against APEC in chicken and human macrophages and in wax moth larval model. Further, the expression of several QS, virulence, biofilm and motility associated genes of APEC O78 were assessed to provide insight on their potential mode of action. Our results showed 10 SMs that modulated the APEC infection both in vitro and in vivo and identified potential leads for future application in poultry for APEC control and thereby also reduce human ExPEC infections.

Material and Methods

Small molecules library. A library of 4,182 compounds 'yactives' selected through pre-screening of 81,320 compounds was obtained from Chembridge, Inc. (San Diego, Calif., USA). These compounds were dissolved in 100% dimethyl sulfoxide (DMSO) to a concentration of 10 mM in a 96-well plate and stored in −80 C for further use.

Bacterial strains and culture conditions. Luria-Bertani broth (LB; BD Difco) was used for routine propagation of APEC serotypes. APEC serotypes stored in 25% glycerol at −80° C. were inoculated into LB broth and grown overnight at 37° C. with shaking at 200 rpm. Rifampicin resistant APEC O78 (Rif$^R$) was isolated by plating the APEC O78 on LB agar containing 50 µg/ml of rifampcin, and one spontaneous resistant mutant was used for the wax moth studies. *E. coli* DH5a was purchased from Invitrogen (Carlsbad, Calif.) and was grown overnight in LB broth at 37° C. with shaking at 200 rpm. *V. harveyi* BB170 (AI-1V; AI-2-) and *V. harveyi* BB120 (AI-1$^+$; AI-2$^-$) were grown in AB medium at 30° C. aerobically with shaking.

Primary screening for non-growth inhibitors. Overnight culture of APEC O78 prepared in LB broth was adjusted to an optical density (OD$_{600}$) of 0.05 (7×10$^7$ CFU/mL) in fresh LB broth. One hundred micro-liters of the culture was transferred to a 96-well plate and 1 µL (100 µM final concentration) of the compound was added to each well using a pin tool. Chloramphenicol (40 µg/mL) or kanamycin (30 µg/mL), and 1 µL of 100% DMSO, were included as controls in each plate. Plates were incubated at 37° C. for 10 h with shaking in a Sunrisem™ Tecan plate reader (Tecan Group Ltd. San Jose, Calif., USA) and the growth was kinetically monitored every 30 min by measuring the OD at 600 nm. Compounds that resulted in no growth inhibition (no elevated OD) were chosen for AI-2 bioluminescence inhibition screening.

AI-2 bioluminescence indicator assay. The AI-2 bioluminescence assay was performed as described previously. Briefly, APEC O78 culture grown in the presence of SMs from above was centrifuged at 5000×g for 10 min, and cell-free culture supernatants were prepared by using a 0.22 µm filter 96 well plate (Millipore). The bioluminescence reporter *V. harveyi* BB170 (AI-1$^+$ and AI-2$^-$) was grown overnight in AB medium at 30° C. aerobically with shaking. The overnight culture was diluted to 1:5000 in fresh AB medium and incubated at 30° C. for 3 h. Following incubation, 180 µL of the *V. harveyi* BB170 culture was distributed into each well of a 96-well plate and mixed with 20 µL of the cell free culture supernatant, the plate was then incubated at 30° C. for 2.5 h in the dark and the bioluminescence was measured using in vivo imaging system (IVIS Lumina Series III, PerkinElmer, USA). The incubation time was determined based on the preliminary studies which showed the optimal induction of bioluminescence at 2.5 h. Cell-free culture supernatant collected from overnight cultures of *V. harveyi* BB120 (AI-1$^+$ and AI-2$^+$) and *E. coli* DH5α were used as controls. Bioluminescence of SMs treated culture supernatant was compared to DMSO treated control. The Z-score was calculated to evaluate the quality of the bioluminescence screening. Four independent experiments were conducted for the 69 compounds that inhibited ≥75% of the AI-2 mediated bioluminescence and the average inhibition percentage was calculated. Ten compounds that showed highest AI-2 inhibition were selected for further studies. The details of the selected SMs are listed in Table 4.

TABLE 4

Chemical information about the selected AI-2 inhibitors

| SM | Chemical name | Molecular weight |
|---|---|---|
| C1 | {2-chlorobenzyl}{[1-(2-methoxyethyl)-4-piperidinyl]methyl}(4-pyridinylmethyl)amine | 387.9 |
| C2 | 1-[1-(3-chloro-4-fluorobenzoyl)-3-piperidinyl]-4-(2-methylphenyl)piperazine | 415.9 |
| C3 | 2-{[3-(trifluoromethyl)phenyl]amino}benzamide | 280.2 |
| C4 | methyl N'-(2-hydroxy-S-methylbenzylidene)hydrazonothiocarbamate | 223.3 |
| C5 | 1-(4-methylbenzyl)-4-(3-phenylpropyl)piperazine | 308.5 |
| C6 | N-(4-bromophenyl)-3-nitrobenzenesulfonamide | 357.2 |
| C7 | N-(4-bromophenyl)-3-[4-(2-fluorophenyl)-1-piperazinyl]propanamide | 406.3 |
| C8 | N-(2-ethylphenyl)-4-(2-methylimidazo[1,2-a]pyridin-3-yl)-1,3-thiazol-2-amine | 334.4 |
| C9 | 1-(4-fluorobenzyl)-4-({3-[4-(trifluoromethyl)phenyl]-1,2,4-oxadiazol-5-yl}methyl)-1,4-diazepane | 434.4 |
| C10 | 2-[4-(1-phenyl-4-piperidinyl)-1-(3-phenylpropyl)-2-piperazinyl]ethanol | 407.6 |

The selected compounds were also tested for inhibition of AI-2 production in other APEC serotypes such as O1, O2, O8, O15, O18, O35, O109, and O115 that are commonly implicated in colibacillosis using the procedure described above.

Biofilm assay. Effect of the selected AI-2 inhibitors on biofilm formation was assessed using crystal violet (CV) assay. Briefly, APEC O78 was grown in LB broth in the presence of 100 µM of each compound in a 96-well plate at 37° C. for 10 h. The culture was then diluted 1:100 in fresh LB broth. The biofilm assay was performed in 96-well plate contain 150 µL of the diluted culture and 100 µM of each compound. The plate was then incubated aerobically without shaking at 37° C. for 48 h, washed twice with PBS to remove the non-adherent cells and stained with 200 µL of 0.1% CV in water at room temperature for 10 min. The plate was washed with PBS and biofilm was quantified by measuring the absorbance at 550 nm after solubilizing the CV in 200 µL of 30% acetic acid in water for 15 min. Two independent experiments were conducted in triplicate wells in each experiment.

Motility assay. The effect of selected AI-2 inhibitors on APEC motility was performed as described previously. Briefly, overnight culture of APEC O78 was adjusted to an OD$_{600}$ of 0.05 and 100 µL was transferred to each well of a 96 well plate and grown in the presence of 100 µM of each compound at 37° C. for 10 h. The culture was then adjusted to an $OD_{600}$ of 0.05 and used for the motility assay. The motility assay was performed in a 48-well plate using semisolid agar media (0.4% LB agar) containing 0.01% tetrazolium chloride and 100 µM of each compound. One microliter of the OD adjusted culture was stabbed onto the middle of the agar and the plate was incubated at 37° C. for 6 h. The motility was assessed by measuring the diameter of the halo zone in comparison to DMSO treated control. Two independent experiments were conducted with duplicate wells in each experiment.

Lactate dehydrogenase (LDH) assay. The selected 10 AI-2 inhibitors were evaluated for their toxicity to Caco-2 (ATCC® HTB-37™) using LDH assay. Briefly, Caco-2 cells ($1.4 \times 10^5$ cells/well) were grown in a 96-well plate in minimal essential medium (MEM) supplemented with 20% fetal bovine serum (FBS; Gibco), 1% non-essential amino acid (NEAA, Invitrogen Life Technologies) and 1 mM sodium pyruvate, at 37° C. in a humidified 5% $CO_2$ incubator for 48 h until a complete monolayer was formed. For LDH assay, cells were washed twice with media containing no FBS/no antibiotics and incubated with 150 µL of fresh media containing 100 µM of each compound at 37° C. for 24 h with 5% $CO_2$. Fifty microliters of supernatant was analyzed using LDH Cytotoxicity Assay Kit (Thermo Scientific). Two independent experiments were conducted in triplicate wells in each experiment.

Toxicity was also determined on HD-11 cells (CVCL-4685). The HD-11 cells ($1.4 \times 10^5$ cells/well) were grown in Iscove's modified Dulbecco's medium (IMEM; Gibco) supplemented with 2 mM glutamine and 10% FBS at 37° C. in a humidified 5% $CO_2$ for 48 h until a monolayer was completely formed. LDH assay was conducted as described above. Two independent experiments were conducted in triplicate wells in each experiment.

Hemolysis assay. The hemolytic activity of the selected AI-2 inhibitors was determined as described before. Briefly, 200 µL of the 10% RBCs (LAMPIRE Biological Laboratories) suspension in PBS was incubated with 100 µM of each compound for 1 h in a 96-well plate. The plate was then centrifuged at 5000×g for 5 min, placed on ice for 5 min and the absorbance of the supernatant was measured at 540 nm. PBS, 1% DMSO, and 0.1% Triton X-100 were used as controls. Two independent experiments were conducted in triplicate wells in each experiment.

Intracellular survival assay. The effect of the selected AI-2 inhibitors on the survival of APEC in macrophage cells was tested as described before. Briefly, HD-11 cells was grown as described above and infected with $1 \times 10^7$ CFU (MOI=100) of mid-log phase APEC strains (O78, O1 and O2) at 37° C. for 1 h. Cells were washed with PBS and treated with gentamicin (150 µg/mL) for 1 h to kill the extracellular bacteria. The cells were then washed and incubated with 100 µM of each compound in media containing 10 µg/mL of gentamicin at 37° C. for 6 h. Following treatment, cells were washed, lysed with 0.1% Triton X-100 for 5 min, ten-fold serially diluted in PBS and plated on LB agar plates to determine CFUs. Cells treated with chloramphenicol (40 µg/mL) and 1 µL of 100% DMSO were used as controls. The experiment was conducted two times in four wells in each experiment. Intracellular survival was expressed as the log change of APEC CFUs in the AI-2 inhibitors treated cells.

Similarly, the intracellular survival assay was also performed in THP-1 cells (ATCC® TIB-202™) as described above. The THP-1 cells were grown in RPMI 1640 medium (Gibco) supplemented with 10% FBS and 2 mM glutamine. In order to differentiate the THP-1 monocyte to macrophage, 100 nM phorbol myristate acetate (PMA; Sigma-Aldrich) was added to the media. The cells ($1.4 \times 10^5$ cells/well) were grown in a 96-well plate in a 5% $CO_2$ incubator at 37° C. for 48 h, infected with APEC (MOI=100), treated with each compound and the intracellular bacteria was determined as above.

Figure 8:
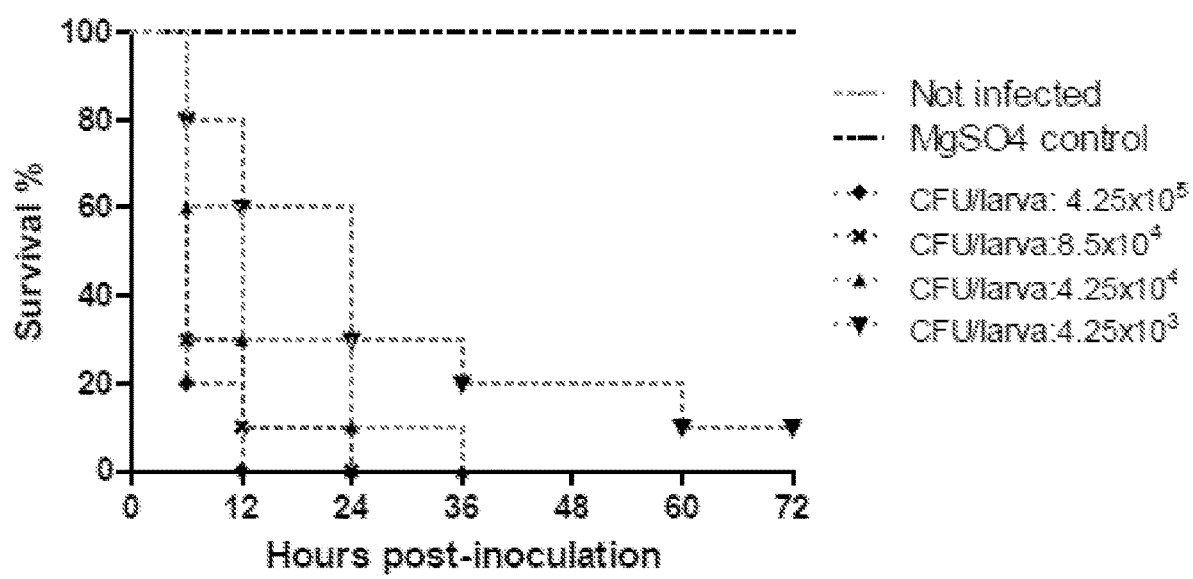
FIG. 8 shows the determination of the Rif' APEC O78 infection dose to the wax moth larvae. Each larva (n=10) was inoculated with 8.5 μL of different concentration of Rif' APEC O78 grown to the mid exponential phase via the last right proleg. Larvae were incubated at 37° C. in the dark and the survival was monitored for 72 h. For the quantification of APEC inside the larvae, dead and live larvae were surface sterilized with 70% ethanol, homogenized in PBS and tenfold serial dilutions of the suspension was plated on MacConkey agar plates supplemented with 50 μg/mL of rifampicin. The plates were then incubated overnight at 37° C. and CFUs determined.

Wax Moth (*Galleria mellonella*) larva infection model. *G. mellonella* caterpillars (larvae) in the final instar stage (fifth instar) were obtained from Vanderhorst, Inc. (St. Mary's, Ohio, USA), stored in wood shavings in a petri dish in the dark and used within 7 days of receiving. Larvae with 15-25 mm length, 250-350 mg weight, having a creamy color with minimal speckling and no grey markings were used in this study. The infection was performed as described previously. For the inoculation, AI-2 inhibitors were diluted in a buffer mix (30% DMSO plus 10 mM $MgSO_4$) as described previously and each larva (n=10) was inoculated with 8.5 µL (50 mg/kg; 12.5 µg/larva) of the AI-2 inhibitors into the hemocoel via the last left proleg using PB600-1 repeating dispenser (Hamilton) attached to insulin syringe (31 gauge, 8 mm needle length; ReliOn). Larvae were placed inside sterile petri dishes and incubated for 2 h in the dark at 37° C. Then, larvae were infected with 8.5 µL of ($4.25 \times 10^4$ CFU) of $Rif^r$ APEC O78 in 10 mM $MgSO_4$ on the right hind proleg. $Rif^r$ APEC O78 was generated by plating APEC on LB agar plate containing 50 µg/mL rifampicin for specific monitoring of APEC population inside the larvae. AI-2 inhibitors possessed similar AI-2 inhibition against Rif APEC O78 as that of parent wild-type APEC O78. Infection dose of $Rif^r$ APEC O78 to larvae was identified based on preliminary study (FIG. 8). Larvae were incubated at 37° C. in the dark and the survival was monitored daily for 72 h. Infected larvae treated with 1% DMSO, 10 mM $MgSO_4$ and 75 mg/kg of chloramphenicol were used as controls.

For the quantification of APEC inside the larvae, dead and live larvae were surface sterilized with 70% ethanol, homogenized in PBS. The suspension was tenfold serially diluted and plated on MacConkey agar plates supplemented with 50 µg/mL of rifampicin. The plates were then incubated overnight at 37° C. and APEC load was enumerated. Two independent experiments were conducted using larvae (n=10) obtained in different batches.

Toxicity of SMs in wax moth larvae. To confirm that the death of the larvae was not due to the compounds toxicity, toxicity of AI-2 inhibitors was assessed in a separate experiment. *G. mellonella* larvae (fifth instar; n=10) were inoculated with 8.5 µL of SMs (50 mg/kg body weight; 12.5 µg/larva) into the hemocoel via the last left proleg. Post inoculation, larvae were placed inside sterile petri dishes and incubated in the dark at 37° C. for 72 h and larval survival was monitored every 24 h. Two independent experiments were conducted Quantitative real-time reverse transcription PCR (qRT-PCR). The effect of the selected AI-2 inhibitors on the expression of QS-regulated and virulence factors genes of APEC was determined using qRT-PCR. APEC O78 was grown in the presence of 100 µM of each compound in a 96-well plate at 37° C. for 10 h. APEC O78 culture treated with 1 µL of 100% DMSO was used as positive control. Total RNA was extracted from duplicate wells for each compound (200 µL) using a miRNeasy Mini Kit (Qiagen). RNA quality and quantity was determined by nanodrop 2000 C spectrophotometer (Thermo scientific). Traces of DNA was removed using Genomic DNA removal mix (Qiagen). Approximately, 5 µg of purified RNA was used to synthesize cDNA using the Qiagen $RT^2$ First Strand Kit (Qiagen). The qRT-PCR was performed using SensiMix™ SYBER® Hi- Rox qPCR Master Mix (Bioline) according to manufacturer instructions in a realplex² mastercycler (Eppendorf) with 55° C. annealing temperature. Gene-specific primers were designed using PrimerQuest Tool and obtained from integrated DNA technologies (IDT). The primers used with target genes' description are listed in Table 5. The data were normalized to the house-keeping gene, glyceraldehyde-3-phosphate dehydrogenase (GAPDH). The relative fold change was calculated using the ΔΔCt method. Three independent experiments were conducted.

TABLE 5

Real Time PCR Primers used in this study.

| Function | Genes | Gene product | Oligonucleotide sequence (5' to 3') | product size (bp) |
|---|---|---|---|---|
| AI-2 synthesis, biofilm formation, cell motility and exopoly-saccharide formation | LuxS | S-ribosylhomo-cysteinase | F: ACGAGTGCATCTGGTAAGTG (SEQ ID NO: 1) R: CAATGGAAGACGTGCTGAAAG (SEQ ID NO: 2) | 87 |
| | Pfs | 5'-methylthio-adenosine/S-adenosyl-homocysteine nucleosidase | F: CGGCAGAACCGGTGTTAATAAT (SEQ ID NO: 3) R: TGAAATCGGGCATCGGTAAAG (SEQ ID NO: 4) | 96 |
| | hha | Hemolysin expression-modulating protein | F: GTGATCTGCGGCTGAGTAAA (SEQ ID NO: 5) R: ACGTCGTTGCCAGACAAT (SEQ ID NO: 6) | 103 |
| | wzb | protein-tyrosine-phosphatase | F: TCGTTATCCCAGTGACCAAAC (SEQ ID NO: 7) R: GTGTCGCAACTATGACCTGAT (SEQ ID NO: 8) | 114 |
| | ompG | outer membrane protein G precursor | F: CGGTTGGCTGTCGATGTATAA (SEQ ID NO: 9) R: AGGTATATTGCAGACCCGTTTC (SEQ ID NO: 10) | 95 |
| | rcsB | transcriptional regulator RcsB | F: CAAGTACATCAAGCGCCATTTC (SEQ ID NO: 11) R: CCCTTCGATATCCAGATCCAATAC (SEQ ID NO: 12) | 103 |
| | motB | Flagellar motor protein B | F: AGGCTAATACGGTTGGGAATAC (SEQ ID NO: 13) R: AGAATCGCCCGATGTTTAGAA (SEQ ID NO: 14) | 109 |
| | FlgN | flagella synthesis chaperone protein FlgN | F: CCAGTAACCAGCCGTTATGTT (SEQ ID NO: 15) R: TACGCAGGAAAGAACCCAATAC (SEQ ID NO: 16) | 117 |
| | fliP | flagellar biosynthetic protein FliP | F: AGCCATTCAGCGAAGAGAAA (SEQ ID NO: 17) R: GTCTGGCAAACAACCCTAAATC (SEQ ID NO: 18) | 117 |
| | CheW | Purine-binding chemotaxis protein CheW | F: CATCCACCTGGCTGAACTTA (SEQ ID NO: 19) R: GTAACACGGATTGCGAACAC (SEQ ID NO: 20) | 106 |
| | nlpC | probable lipoprotein nlpC precursor | F: GCATCGTCACAACCACAAATC (SEQ ID NO: 21) R: GGTTTGAACGACCAGCTACA (SEQ ID NO: 22) | 103 |
| Virulence-associated genes | ompA | membrane protein | F: TGACCGAAACGGTAGGAAAC (SEQ ID NO: 23) R: GGAATACCAGTGGACCAACAA (SEQ ID NO: 24) | 99 |
| | FimC | fimbrial chaperone protein | F: GCTGGCAGGTATCCTGATATTC (SEQ ID NO: 25) R: TGCCCTGCCGGATAAATTAC (SEQ ID NO: 26) | 99 |
| | IucD | IucD protein | F: GTCCGGAGAAGCCTGAAATA (SEQ ID NO: 27) R: GAGAAGCGGCGGAAATAAAC (SEQ ID NO: 28) | 114 |
| | FyuA | ferric Yersinia-bactin uptake A | F: CTTCCCTTCCGGTTCGTTAATC (SEQ ID NO: 29) R: GGTACAGCCCAAACACCATATC (SEQ ID NO: 30) | 119 |

TABLE 5-continued

Real Time PCR Primers used in this study.

| Function | Genes | Gene product | Oligonucleotide sequence (5' to 3') | product size (bp) |
|---|---|---|---|---|
| | iss | serum survival protein | F: CGCTCTGGCAATGCTTATTAC (SEQ ID NO: 31) <br> R: GAAATGATGGGTGATGGTTTCC (SEQ ID NO: 32) | 100 |
| | vat | vacuolating autotransporter toxin | F: CTGAACCGCGTCCAGATTAT (SEQ ID NO: 33) <br> R: ACTCCACGGCAGGAAATATG (SEQ ID NO: 34) | 104 |
| Cell division, DNA processing and morphology | bolA | BolA protein | F: CAGTACTTTAGCGGAGGAACTC (SEQ ID NO: 35) <br> R: CAACCCTTCCCACTCCTTAAT (SEQ ID NO: 36) | 82 |
| | MreD | rod shape-determining protein MreD | F: CCGGTCTGAAAGAGACGTTAAT (SEQ ID NO: 37) <br> R: TTCCGCAACCTCGCATTAT (SEQ ID NO: 38) | 115 |
| | csrA | carbon storage regulator A | F: GTAACTGGACTGCTGGGATTT (SEQ ID NO: 39) <br> R: CCAGGTACGTATTGGCGTAAA (SEQ ID NO: 40) | 100 |
| | murD | UDP-N-acetylmuramoyl-alanine-D-glutamate ligase | F: GCGTGGTTAATGCTGATGATG (SEQ ID NO: 41) <br> R: CCTGCTGATGATTCAGGTGATA (SEQ ID NO: 42) | 108 |
| | lpp | major outer membrane lipoprotein precursor | F: CGGTAATCCTGGGTTCTACTCT (SEQ ID NO: 43) <br> R: TGCTCAGCTGGTCAACTTTAG (SEQ ID NO: 44) | 108 |
| Small molecules metabolism | frwC | fructose-like-2 IIC component | F: AGCAGGGCAGCATTGTTAT (SEQ ID NO: 45) <br> R: GCAAATCAGCATGAAGGCATAG (SEQ ID NO: 46) | 104 |
| | Fpr | ferredoxin-NADP reductase | F: GTTCCTGCATCAGAGGTAGATAG (SEQ ID NO: 47) <br> R: TACAGCGATTGGCCCTTATT (SEQ ID NO: 48) | 128 |
| | Mt1R | mannitol operon repressor | F: CGTCATTAACCGCCAGGAATA (SEQ ID NO: 49) <br> R: GTTCACCAAAGGGTCCAAGTA (SEQ ID NO: 50) | 122 |
| | UgpC | SN-glycerol-3-phosphate transport ATP-binding protein ugpC | F: CTGATCGTGGGTAACGTAGAG (SEQ ID NO: 51) <br> R: GCAGTGTTCCTGTTTGATGAG (SEQ ID NO: 52) | 126 |
| | ThiH | thiazole biosynthesis protein thiH | F: GCATAAGTCGCCTCGTGATATG (SEQ ID NO: 53) <br> R: GACGGAATACGCCGAGTTAAAG (SEQ ID NO: 54) | 81 |
| Housekeeping gene | GAPDH | glyceraldehyde-3-phosphate dehydrogenase | F: CGGTACCGTTGAAGTGAAAGA (SEQ ID NO: 55) <br> R: ACTTCGTCCCATTTCAGGTTAG (SEQ ID NO: 56) | 99 |

Statistical analysis. Data from biofilm formation, motility, qRT-PCR, toxicity, hemolytic 46 activity, intracellular survival, and wax moth infection assays were expressed as the mean±standard deviation. ANOVA followed by Tukey test was used to analyze these data and a P-value <0.05 was used to determine statistically significant differences between means. A fold change of ±1.5≥ or ≤1.5 and a P-value ≤0.05 were used to determine statistically significant differences in gene expression. The differences between the gene expression profiles were analyzed using a principal component analysis (PCA) on IMP PRO 13 software (SAS Institute). Statistical analyses for the wax moth infection studies were performed using GraphPad Prism 5 software (GraphPad, Inc.) and plotted using the Kaplan-Meier graph.

Results

Figure 9A:
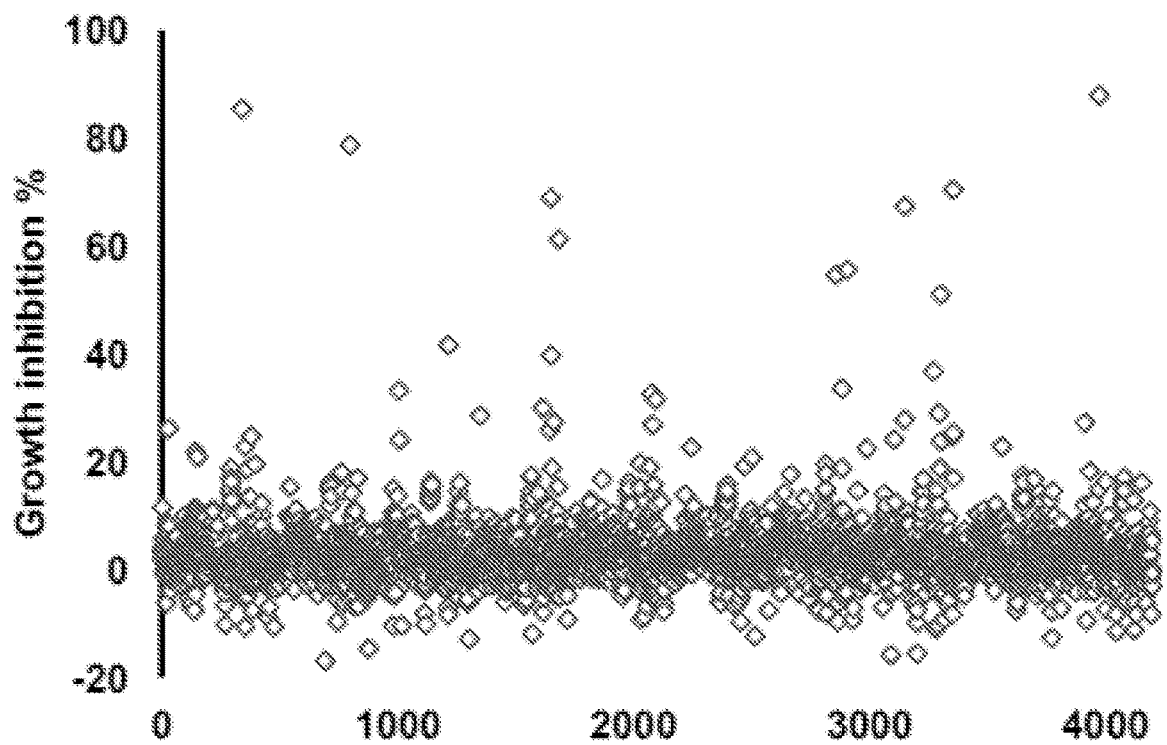
FIG. 9A shows the high-throughput screening for growth inhibition against APEC O78. 4,122 compounds did not impact the growth of APEC O78 (less than 20%).
Figure 9B:
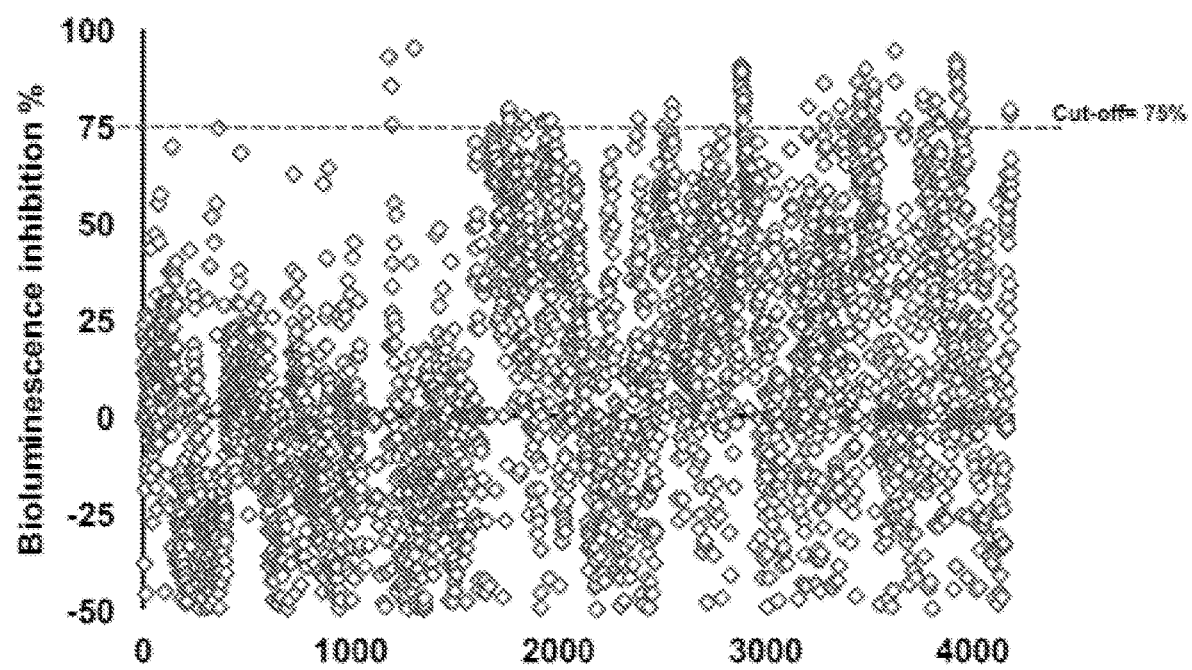
FIG. 9B shows the screening of the SMs for their effect on the AI-2 activity of APEC O78. The *Vibrio harveyi* BB170 AI-2 bioluminescent indicator bacteria was used to screen the cell-free culture supernatant of APEC O78. APEC cell-free culture supernatant was prepared from cultures grown in the presence of 100 µM of small molecules. Sixty-nine compounds inhibited ≥75% of the AI-2 activity of APEC O78. AI-2 bioluminescence indicator assay was repeated four times for these 69 compounds and 10 compounds that showed highest AI-2 inhibition were selected for further studies.

Primary screening identified 69 compounds that significantly inhibited the AI-2 activity of APEC. A total of 4,182 small molecules (SMs) were screened for APEC O78 growth inhibition. The results showed that 4,122 compounds did not impact the growth of APEC O78 (no elevated OD) (FIG. 9A). Supernatants from cultures grown in the presence of 4,122 compounds were screened for their ability to inhibit bioluminescence using *V. harveyi* AI-2 indicator. Inhibition of AI-2 activity was calculated by comparing bioluminescence inhibition from SM treated APEC O78 culture with that of the DMSO treated control. A total of 69 compounds inhibited ≥75% of the AI-2 activity and these 69 compounds were further screened in four independent experiments and 10 compounds that showed highest AI-2 inhibition (75-98%) were selected for further studies (FIG. 9B). However, dose response studies revealed only 25 inhibition of AI-2 activity of APEC O78 with some SMs at 50 uM and no inhibition was observed at lower concentrations.

Further, the selected AI-2 inhibitors displayed differential effect on multiple APEC serotypes. Most compounds resulted in ≥75% inhibition of AI-2 activity of O2 except C3 and C9; while, only C1 and C6 resulted in ≥75% inhibition for AI-2 activity of O1. Only C6 exhibited ≥75% inhibition for AI-2 activity of O8, O15, O18 and O35. Whereas C8 exhibited ≥75% inhibition for AI-2 activity of O109 while C6 and C10 exhibited ≥75% inhibition for AI-2 activity of O115 (Table 6).

TABLE 6

Effect of the selected SMs on the AI-2 activity of different APEC serotypes

| | Inhibition % | | | | | | | | | |
|---|---|---|---|---|---|---|---|---|---|---|
| | C1 | C2 | C3 | C4 | C5 | C6 | C7 | C8 | C9 | C10 |
| O78 | 84 | 92 | 78 | 75 | 83 | 92 | 94 | 98 | 79 | 84 |
| O2 | 94 | 96 | 54 | 76 | 89 | 93 | 83 | 94 | 51 | 89 |
| O1 | 76 | 64 | 65 | 63 | 46 | 93 | 47 | 41 | 19 | 64 |
| O8 | 20 | 20 | 39 | 0 | 18 | 79 | 2 | 18 | 20 | 0 |
| O15 | 13 | 27 | 0 | 46 | 45 | 97 | 36 | 25 | 0 | 22 |
| O18 | 37 | 43 | 8 | 54 | 61 | 95 | 48 | 54 | 14 | 35 |
| O35 | 48 | 55 | 37 | 60 | 68 | 96 | 62 | 57 | 36 | 47 |
| O109 | 65 | 57 | 0 | 67 | 69 | 60 | 67 | 75 | 66 | 57 |
| O115 | 64 | 52 | 35 | 58 | 63 | 99 | 45 | 44 | 44 | 78 |

Figure 10A:
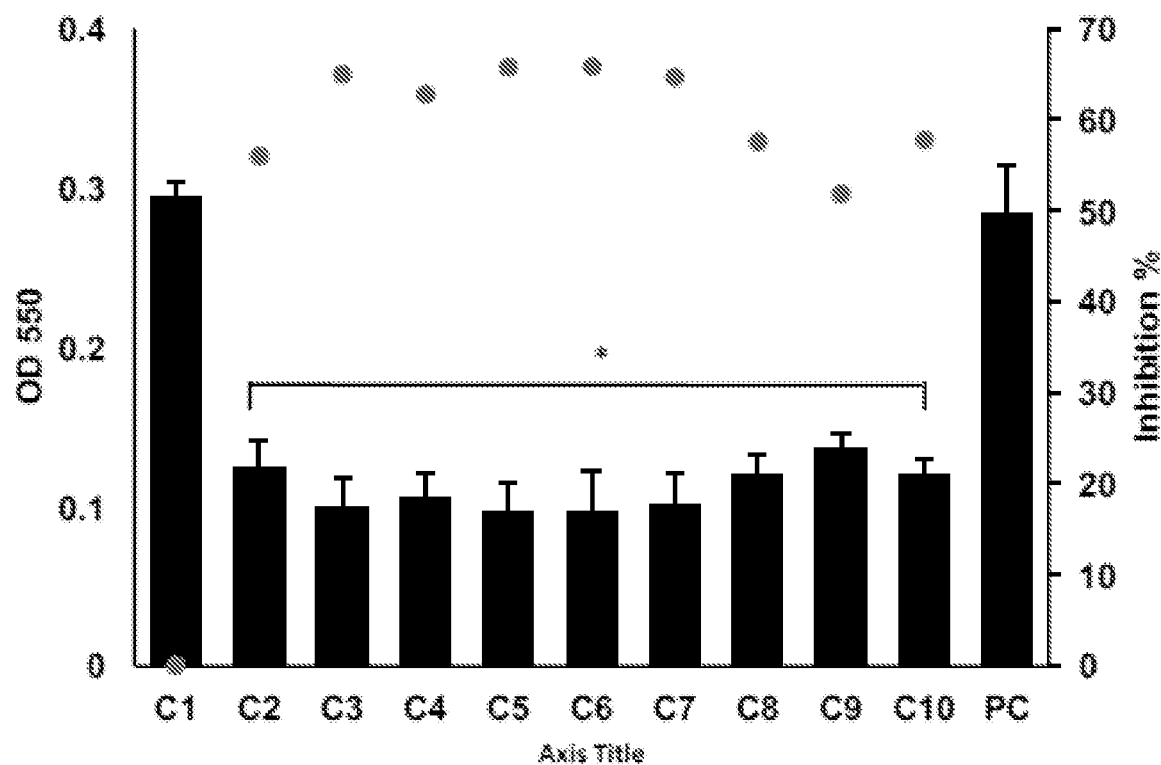
FIG. 10A shows the effect of the selected AI-2 inhibitors on biofilm formation of APEC O78. Biofilm formation was assessed using crystal violet assay by measuring the $OD_{550}$. All of the compounds significantly inhibited the biofilm formation except C1 in comparison to the DMSO treated control (PC). Two independent experiments were conducted with triplicate wells in each experiment and the average $OD_{550}$ (bars) and inhibition % (dots) are shown.

Inhibition of AI-2 activity was calculated by comparing bioluminescence inhibition from SM treated APEC O78 culture with that of the DMSO treated control The selected AI-2 inhibitors affected biofilm formation and motility of APEC O78. Quorum sensing has been shown to regulate motility and biofilm formation in many bacteria. Biofilm plays a crucial role in APEC virulence and enhances the bacterial resistance to antimicrobials and immune clearance, leading to failure of antimicrobial therapy; therefore, QSI have been proposed as promising anti-biofilm agents. The effect of AI-2 inhibitors on APEC O78 biofilm formation was determined using CV assay. Biofilm formation was assessed after 48 h of incubation in the presence of 100 μM of each compound. It was noted that C3-C7 resulted in 63-66% reduction of APEC O78 biofilm formation while C2, and C8-C10 resulted in 52-58% reduction of APEC O78 biofilm formation, with an average $OD_{550}$ reduction up to 0.2 ($P<0.05$) while C1 induced the biofilm formation of APEC O78 up to 100% (FIG. 10A).

Figure 10B:
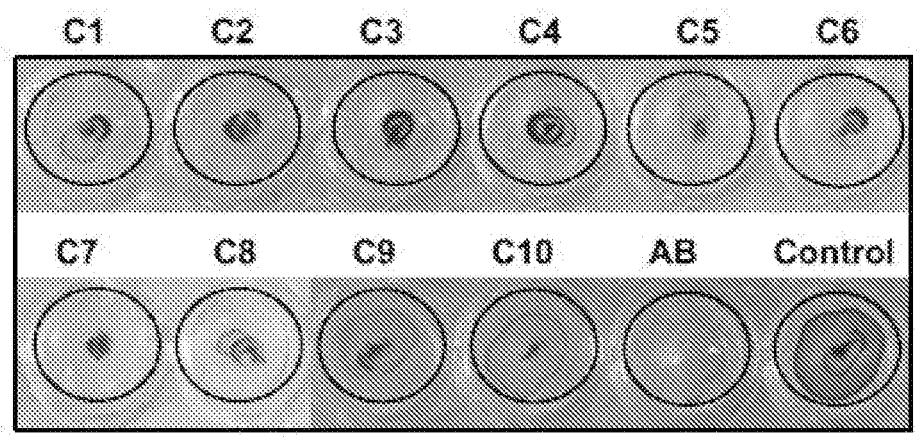
FIG. 10B shows the effect of the selected AI-2 inhibitors on the motility of APEC O78. Motility was assessed by measuring the halo on a semisolid agar. Except C9 and C10, all compounds resulted in complete inhibition (did not form detectable motility halos) in comparison to the DMSO treated control. *Significant difference between AI-2 inhibitors treated compared to DMSO treated control ($P<0.05$).

Motility and chemotaxis allow bacteria to migrate towards favorable environments in response to stress and thus contribute to bacterial fitness and virulence. The effect of AI-2 inhibitors on motility of APEC O78 was determined using 100 μM of each AI-2 inhibitors. Except C9 and C10, all compounds resulted in inhibition (did not form detectable motility halos) of APEC O78 motility after 6 h of incubation in comparison to the DMSO treated control (FIG. 10B). Notably, the diameter of the motility halos reduced from 8 mm in DMSO treated control to 2 mm (on an average) in AI-2 inhibitors treated wells.

Figure 11A:
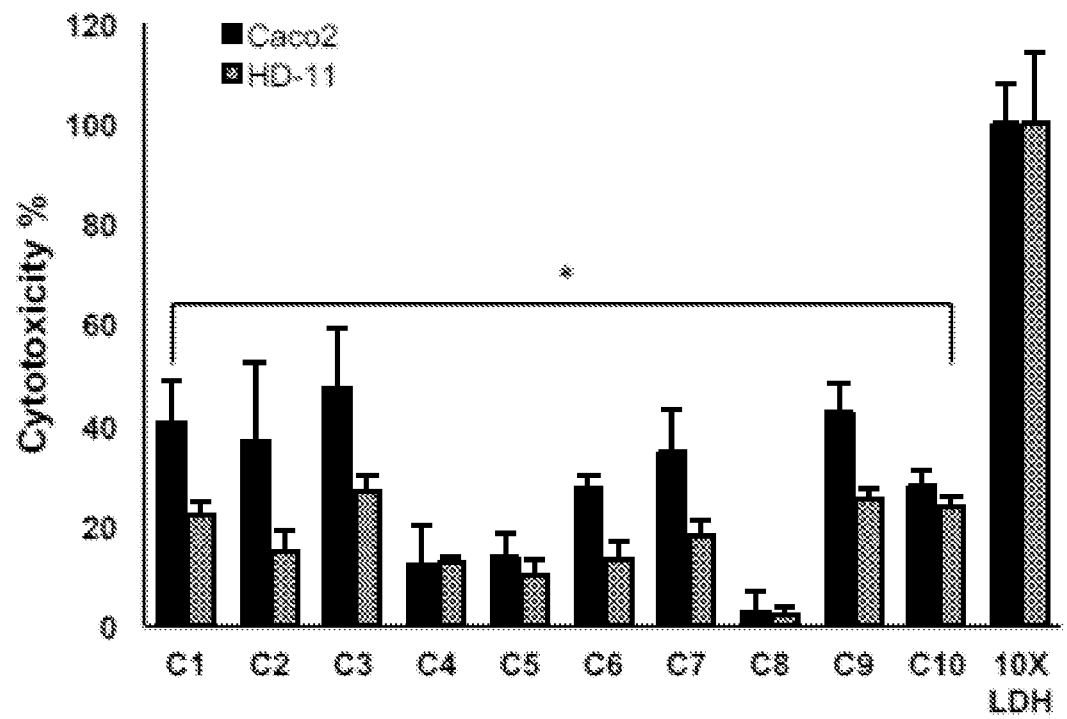
FIG. 11A shows the cytotoxicity of the selected AI-2 inhibitors. Cytotoxicity was assessed using Caco-2 and HD-11 cells. 100 µM of each compound was used in the assays. Most of the compounds showed significantly less cytotoxicity ($P≤0.05$) compared to DMSO treated control. Two independent experiments were conducted with triplicate wells in each experiment and the average is shown. *Significant difference between AI-2 inhibitors treated wells compared to 10×LDH.

The AI-2 inhibitors showed low toxicity on human colonic adenocarcinoma epithelial cells (Caco-2) and chicken macrophage cells (HD-11) and no hemolytic activity on sheep and chickens red blood cells (RBCs). The toxicity of the selected AI-2 inhibitors was assessed on Caco-2 and HD-11 cells using LDH assay. When treated with 100 μM of SMs, C8 and C4 exhibited 2% and 12% toxicity, respectively; while C6 and C10 exhibited 27% toxicity and C1-C3, C7, and C9 displayed 36% to 42% toxicity on Caco-2 cells. Further, on HD-11 cells, C5 and C8 exhibited less than 10% toxicity while C2, C4, C6, and C7 exhibited toxicity between 12% and 18%, and C1, C3, C9 and C10 exhibited toxicity between 22% and 27% (FIG. 11A).

Figure 11B:
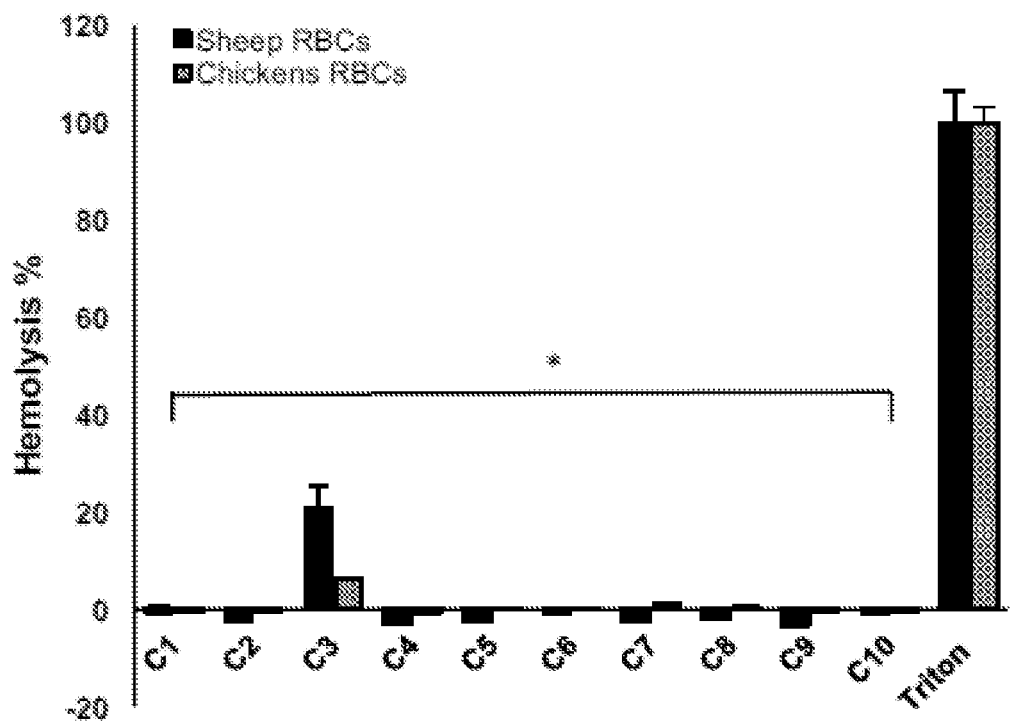
FIG. 11B shows the hemolytic activity of the selected AI-2 inhibitors. Hemolytic activity was determined using sheep and chicken RBCs. 100 µM of each compound was used in the assays. Most of the compounds showed significantly less hemolytic activity ($P≤0.05$) compared to DMSO treated control. Two independent experiments were conducted with triplicate wells in each experiment and the average is shown. *Significant difference between AI-2 inhibitors treated wells compared to Triton X-100.

Additionally, toxicity of the selected AI-2 inhibitors to sheep and chicken RBCs were also tested using 100 μM of each compound. Notably, all compounds exhibited no hemolytic activity against sheep or chicken RBCs except C3, which exhibited 20.6% and 6.4% hemolytic activity to sheep and chicken RBCs, respectively (FIG. 11B).

Figure 12A:
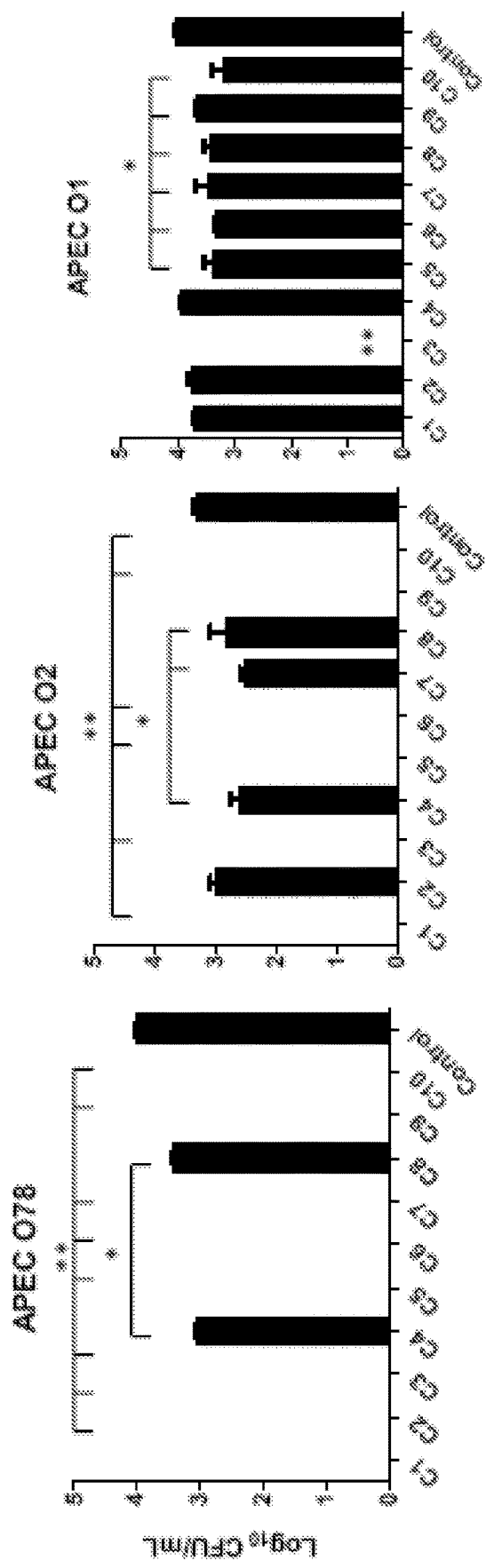
FIG. 12A shows the effect of the AI-2 inhibitors on the intracellular survival of different APEC O78, O2, and O1 in HD-11 cells. Cells were infected with APEC strains at MOI=100, treated for 6 h with 1 µL (100 µM) of each compound and the internalized bacteria were determined. Two independent experiments were conducted with triplicate wells in each experiment and the average is shown. *Significant difference between AI-2 inhibitors treated cells ($P<0.05$) compared to DMSO treated control. **Significant difference between AI-2 inhibitors treated cells ($P<0.001$) compared to DMSO treated control.

The selected AI-2 inhibitors reduced the survival of APEC O78, O2, and O1 in chicken and human macrophage cells. The invasion of APEC into phagocytic cells (macrophages and heterophils) facilitates its intracellular survival and systemic spread to different organs which is critical for APEC pathogenesis. Therefore, it is important that QS AI-2 inhibitors induce their antimicrobial activity on APEC in infected macrophages. HD-11, and acute human leukemia macrophage (THP-1 cells) were used to determine the effect of the AI-2 inhibitors (100 μM) on internalized APEC O78, O1 and O2 (the most predominant APEC serotypes) inside the cells. In HD-11 cells, C1-C3, C5-7, C9 and C10 exhibited 100% clearance of APEC O78 (4 logs reduction; $P<0.001$); while C4 and C8 significantly reduced its intracellular survival (up to 1 log; $P<0.05$) when compared to DMSO treated control. Whereas C1-C3, C5, C6, C9 and C10 exhibited 100% clearance of APEC O2 (3.3 logs reduction; $P<0.001$), and C4, C7 and C8 significantly reduced its intracellular survival (up to 0.8 log; $P<0.05$). Only C3 exhibited 100% clearance of APEC O1 (4 logs reduction; $P<0.001$), while C5-C8 and C10 significantly reduced its intracellular survival (up to 0.9 log; $P<0.05$) (FIG. 12A).

Figure 12B:
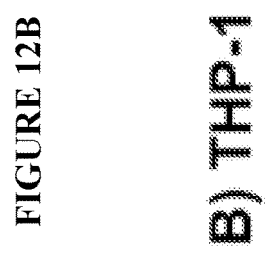
FIG. 12B shows the effect of the AI-2 inhibitors on the intracellular survival of different APEC O78, O2, and O1 in THP-1 cells. Cells were infected with APEC strains at MOI=100, treated for 6 h with 1 µL (100 µM) of each compound and the internalized bacteria were determined. Two independent experiments were conducted with triplicate wells in each experiment and the average is shown. *Significant difference between AI-2 inhibitors treated cells ($P<0.05$) compared to DMSO treated control. **Significant difference between AI-2 inhibitors treated cells ($P<0.001$) compared to DMSO treated control.
Figure 12B:
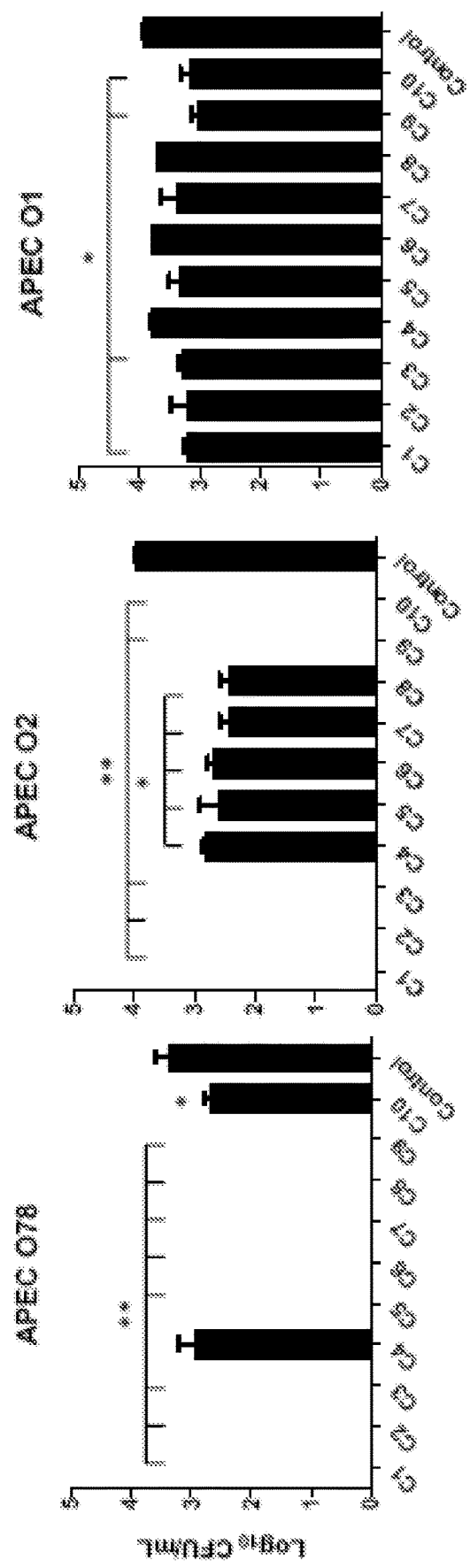

Similarly, in THP-1 cells, C1-C3, and C5-C9 exhibited 100% clearance of APEC O78 (3.4 logs reduction; $P<0.001$) while C10 significantly reduced its intracellular survival (up to 0.7 log; $P<0.05$). Whereas C1-C3, C9 and C10 exhibited 100% clearance of APEC O2 (4 logs reduction; $P<0.001$), and C4-C8 significantly reduced its intracellular survival (up to 1.5 logs; $P<0.05$). Similarly, C1, C9 and C10 significantly reduced the intracellular survival of APEC O1 (up to 0.9 log; $P<0.05$) (FIG. 12B). Interestingly, we observed varying effects of the AI-2 inhibitors on different internalized APEC serotypes in HD-11 and THP-1 cells. Specifically, some AI-2 inhibitors were less effective against O1 and O2. This variation might be due to differences in their capsule composition. Both the O1 and O2 possess K1 (sialic acid) containing capsule, which confers protection against host immunity and increase resistant to the bactericidal effect of serum as compared to O78 which expresses different capsular antigens. In addition, O1 also contains pathogenicity island (PAI $I_{APEC\text{-}O1}$) that carries pap operon (putative virulence genes of APEC), invasion determinant protein encoding gene tia and iron-regulated outer membrane protein encoding gene ireA which are likely to contribute to increased virulence of APEC O1 thus the lower efficicacy of SMs.

Figure 13A:
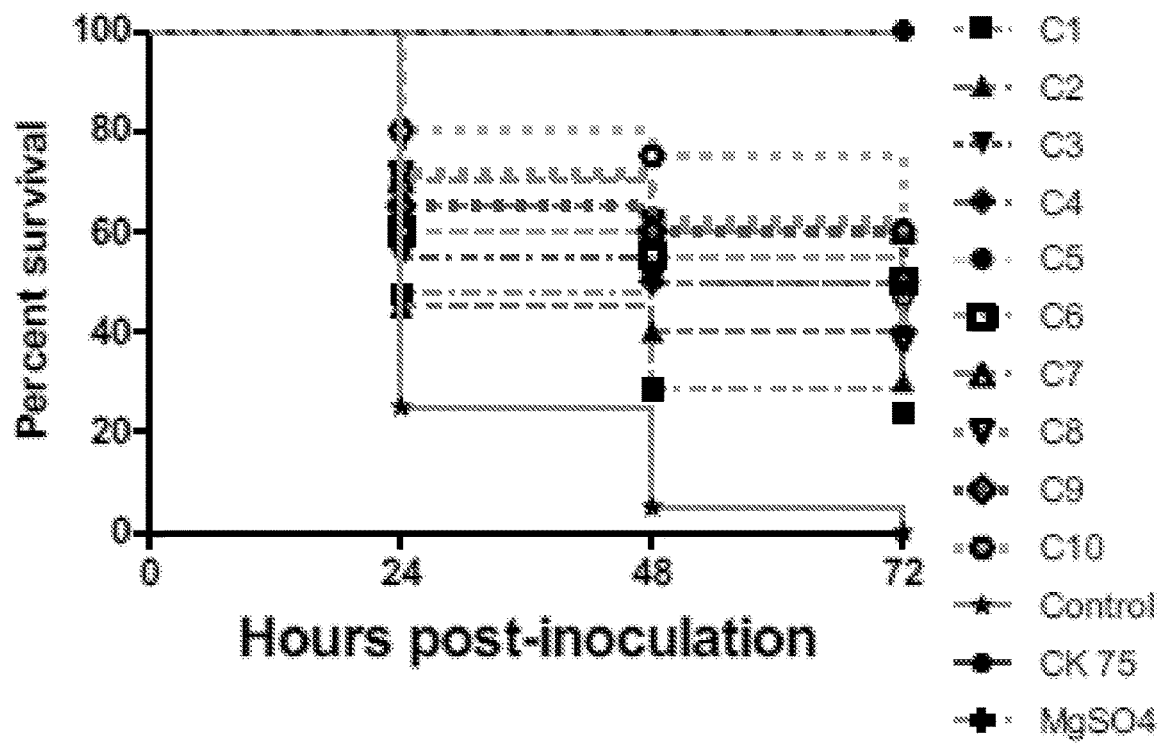
FIGS. 13A-13C show the effect of the AI-2 inhibitors on *G. mellonella* larvae infected with APEC O78.

The AI-2 inhibitors increased the survival of APEC infected G. mellonella larvae. The in vivo efficacy of the AI-2 inhibitors was evaluated using wax moth larval model, which has been previously used to evaluate drug efficacy and bacterial pathogenesis. Treatment of the infected larvae with C1 and C2 resulted in 23% and 30% increase in larval survival, respectively; while compounds C3-10 resulted in 40-60% increase in larval survival in comparison to DMSO treated control (FIG. 13A).

Figure 13B:
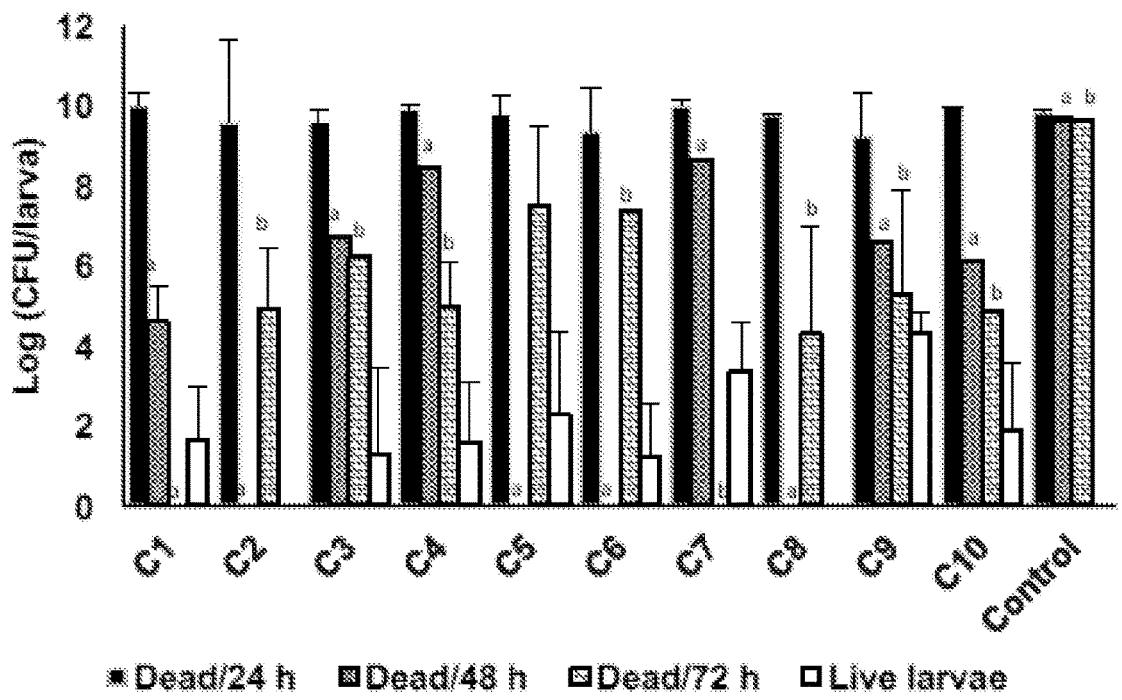

Treatment of the wax moth with the AI-2 inhibitors also reduced APEC O78 population load in both dead and live larvae in comparison to DMSO control. At 72 h post treatment, the bacterial load in dead larvae in all treated groups except C1 and C7 (showed no larval death) were significantly reduced (4.3-7.5 logs; $P<0.05$) in comparison to DMSO treated control. However, in live larvae, C2 and C8 resulted in 100% clearance of APEC (up to 5 logs; $P<0.001$), while C4-C6 and C10 significantly reduced the bacterial load (up to 3.5-6 logs; $P<0.05$) in comparison to dead larvae. Further, at 48 h post treatment, C2, C5, C6 and C8 treated groups showed no larval death while the rest of the compounds resulted in significant reduction of the APEC O78 load (1.2-3.5 logs; $P<0.05$) in comparison to DMSO treated control (FIG. 13B). However, those larvae died at 24 h post treatment possessed APEC load similar to DMSO treated control. These results indicated that the bacterial load in all AI-2 inhibitors treated groups except C9 were significantly decreased over time ($r \leq -0.87$; $p \leq 0.001$) in comparison to DMSO treated control.

Figure 13C:
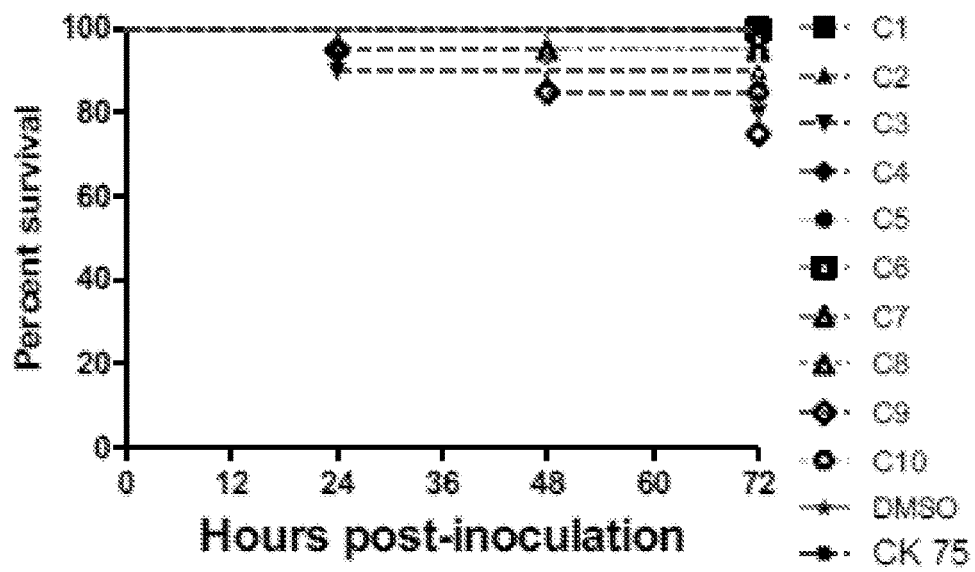

Notably, all AI-2 inhibitors showed no or low toxicity to larvae. The survival of larvae treated with C1 and C6 was 100%. Whereas the survival of larvae was more than 75% for the rest of the AI-2 inhibitors (FIG. 13C). These results suggest that the larval death is not due to the toxic effect of AI-2 inhibitors rather due to APEC O78 infection. Thus, the wax moth model may serve as rapid screening tool to assess the efficacy of potential antimicrobials against APEC for SMs selection for in vivo studies in poultry.

The QS AI-2 inhibitors affected the expression of virulence, biofilm formation and motility-associated genes of APEC. The effective QSI has been proposed to cause efficient reduction of the expression of QS regulated and virulence-associated genes. Therefore, genes representing multiple physiological processes regulated by QS (Table 5) such as AI-2 synthesis (2 genes), small molecules metabolism (5 genes), virulence factors (6 genes), biofilm formation, cell motility and exopolysaccharide formation (11 genes), and cell division, DNA processing, and morphology (5 genes), were analyzed to elucidate mechanisms of how the AI-2 inhibitors might attenuate APEC pathogenicity.

Figure 14A:
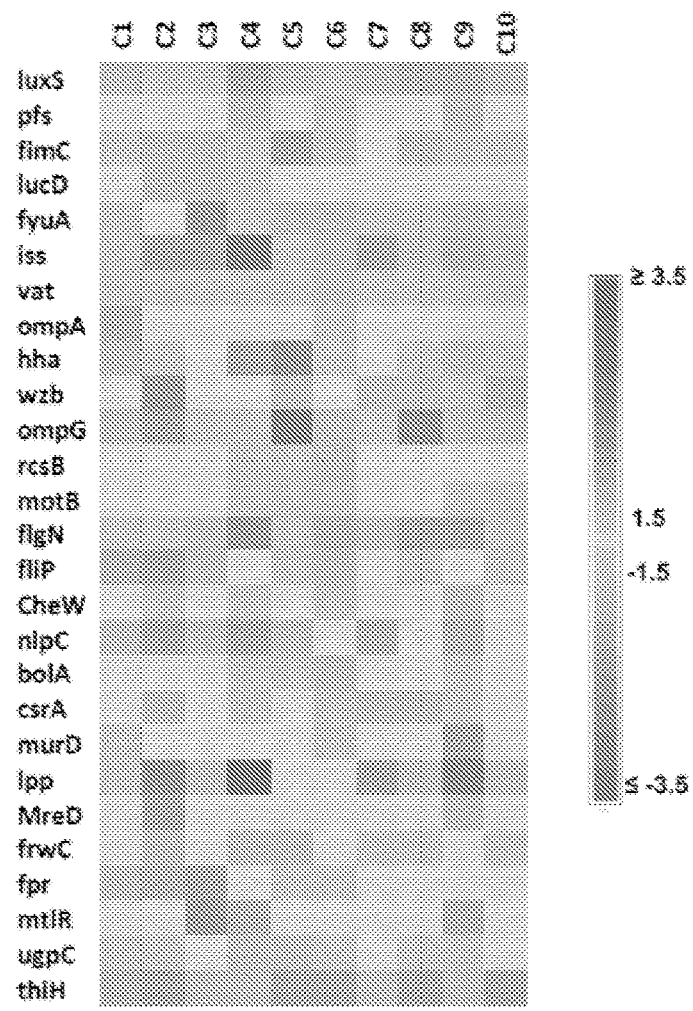
FIGS. 14A-14B show the effect of the AI-2 inhibitors on expression of QS and virulence-associated genes.

Interestingly, all compounds except C4, down-regulated the expression of cytosolic S-ribosylhomocysteine lyase gene (luxS), which mediates AI-2 synthesis. Notably, C4 also up-regulated the expression of 5'-methylthioadenosine/S-adenosylhomocysteine nucleosidase gene (pfs), which also mediates AI-2 synthesis (FIG. 14A). Further, AI-2 inhibitors affected group of genes that influence AI-2 production and degradation and small-molecules metabolism. These genes have not been directly implicated in cell-cell communication, but provide a link between QS and central metabolism. The AI-2 inhibitors down-regulated genes encoding inner membrane sugar transport fructose-like-2 IIC component (frwC; by C5-C8 and C10), and carbohydrate transport sn-glycerol-3-phosphate import ATP-binding protein (ugpC; by C1, C2, C4-C6, C8 and C9), and cytoplasmic ferredoxin-NADP reductase (fpr; by C3, C5 and C6), and thiazole biosynthesis protein (thiH; by C1 and C3-C10) (FIG. 14A).

Since the expression of virulence factors by APEC is among many traits controlled by QS, inhibition of these virulence factors by QSI will render APEC avirulent and non-pathogenic. Notably, AI-2 inhibitors down-regulated the expression of genes encoding periplasm fimbrial chaperone protein gene (type 1 pili fimC; by C1-C6, and C8-C10), iron uptake chelate gene D (iucD; by C4), ferric yersiniabactin uptake A (fyuA; by C3-C10), serum survival protein gene (iss; by C1, C5-C8, and C10), and vacuolating autotransporter toxin gene (vat; by C1-C10). However, C2-C4 and C9 up-regulated the expression of iss gene (FIG. 14A).

AI-2 inhibitors also affected the expression of biofilm formation, motility and exopolysaccharide formation associated genes. The AI-2 inhibitors down-regulated the expression of genes encoding hemolysin expression modulating protein (hha; by C1, C2, C5, C6 and C8-C10), transcriptional regulator protein (rcsB; by C4-C6), outer membrane protein G precursor (ompG; by C2-C10), and tyrosine-phosphatase protein (wzb; by C5, and C7-C10). Both hha and rcsB are located in the cytosol and shown to be involved in biofilm formation; while ompG and wzb contributes to exopolysacchride formation. Likewise, genes associated with chemotaxis and motility, such as cytoplasmic flagellar synthesis chaperone protein (flgN; by C1-10), chemotaxis protein (cheW; by C4, C6, and C9), flagellar motor protein B (motB; by C4-C6, and C9-C10) and flagellar biosynthesis protein (fliP; by C5, C6, C8, and C10) were also down-regulated by AI-2 inhibitors (FIG. 14A). However, C1-C5, C7, and C9 up-regulated the expression of cell membrane probable endopeptidase (nlpC).

Quorum sensing has also been implicated in the regulation of multiple physiological processes such as DNA replication, cell division and cell morphology. The AI-2 inhibitors down-regulated the expression of genes encoding transcriptional regulators such as cytosolic DNA-binding transcriptional regulator gene (bolA; by C4-C6, and C9), and carbon storage regulator A (csrA; by C4, C6, and C9), and UDP-N-acetylmuramoylalanine-D-glutamate ligase (murD; by C1, C6, and C9). However, C2-C4, and C7-C10 up-regulated the expression of major outer membrane lipoprotein precursor gene (lpp) (FIG. 14A).

Figure 14B:
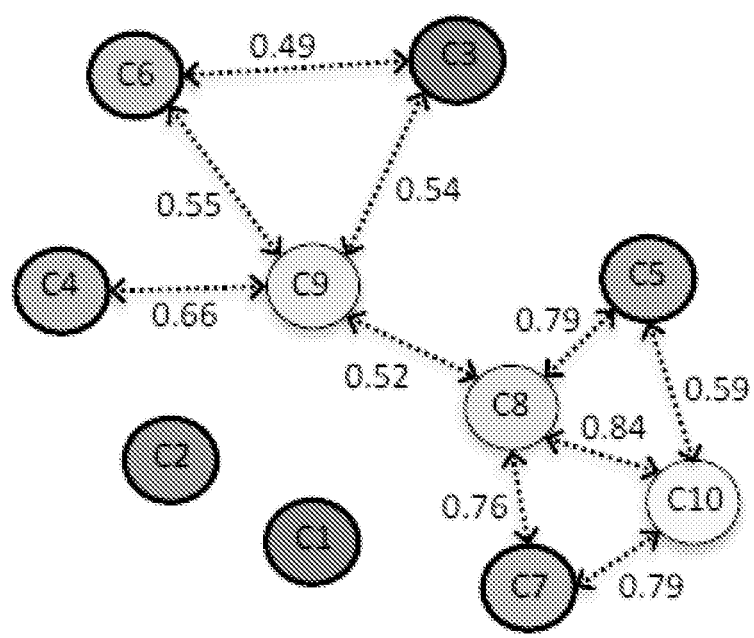

Principal component and multivariate analysis were performed to determine the genes expression profiling of APEC treated with the AI-2 inhibitors. The expression profiling divided the AI-2 inhibitors into 2 groups ($r>0.49$; $P<0.01$). The first group composed of C5, C7, C8 and C10 ($0.59 \leq r \leq 0.84$) while the second group composed of C3, C4, C6 and C9 ($0.49 \leq r \leq 0.66$). The C9 and C8 showed high correlation with other AI-2 inhibitors ($r=0.52$; $P=0.005$) and they connected these two groups together (FIG. 14B). Further, C5 to C10 displayed similarity in their expression profile ($r>0.4$; $P<0.05$), while C1 and C2 showed no significant expression profiles similarity with the other AI-2 inhibitors ($r<0.33$) (FIG. 14B). Despite the high similarity scores between certain AI-2 inhibitors, the gene expression profiles differed between AI-2 inhibitors, suggesting that each AI-2 inhibitors might interact with different target(s) that potentially share common biological pathways within APEC.

Discussion

Increase in antibiotic resistance APEC, limited effect of the current vaccine, and the ability of APEC to establish persistent infections through the formation of biofilms, emphasize the need for alternate control strategies for APEC. A great effort has been made to develop antipathogenic drugs by reducing the bacterial virulence through QSIs, which proves to be an intriguing target for future antimicrobial chemotherapy. In this example, we identified, using *V. harveyi* BB170 AI-2 indicator bacteria, 69 novel QS AI-2 inhibiting compounds that do not, per se, inhibit APEC growth, but interfere with QS-regulated processes including virulence factors release, biofilm formation, motility, exopolysaccharide synthesis, stress survival, cell division and pathogenesis in APEC. Use of QSI to attenuate APEC pathogenicity rather than its growth is attractive as this approach is less likely to result in development of resistant APEC.

In this example, all 10 compounds, except C4, were found to attenuate the AI-2-production and down-regulate the expression of luxS. Specifically, knockout of luxS has been reported to affect AI-2 activity, down-regulate virulence-associated genes, and reduce adherence and invasion abilities of APEC O78 and consequently survival in the cultured cells. Adherence and invasion are important for APEC pathogenesis and mediate colonization, survival and spread of pathogens in the host. These results suggest that AI-2 inhibitors, except C4 might interfere with synthesis, secretion, and/or transport of AI-2 through their effect on the luxS; thus, affecting the interspecies QS and the APEC pathogenicity. The fact that C4 also inhibited the AI-2 production suggest that the C4 might intervene at various points in the AI-2 production cycle without having a direct effect on the luxS.

Interestingly, AI-2 activity has been reported to regulate genes specifying several functions in different pathogens including virulence factors, motility and biofilm formation, DNA replication and cell division, metabolism, and protein biosynthesis, antibiotic production, and AI-2 ATP binding cassette transporter. In this example, C2-C9 were found to reduce biofilm formation of APEC O78 (FIG. 14A). This result was supported by the inhibitory effect of these compounds on biofilm formation-associated genes (FIG. 14A) such as hha which influences persister cell formation and bacterial resistance to antibiotics; rcsB, ompG and wzb which are involved in colanic acid capsule biosynthesis that protects the cells against contact-dependent growth inhibition and cell division; bolA and murD which are involved in the production of fimbria-like adhesins, curli and colanic acid and regulate cell morphology, cell wall formation, permeability, cell growth and division, motility and peptidoglycan biosynthesis; and csrA which regulates central carbohydrate metabolism, glycogen synthesis, gluconeogenesis, cell size and surface properties, motility and flagellum biosynthesis. These findings suggest that the identified AI-2 inhibitors possess anti-biofilm effect against APEC O78 likely through the down-regulation of biofilm- and capsular polysaccharides-associated genes which are important for bacterial adherence, interactions with host cells, and resistance to host immunity. Previously, QSI such as furanone C-30 has been reported to inhibit biofilm formation of *Streptococcus mutans* through the inhibition of QS-regulated genes. Likewise, bacterial motility plays an important role in virulence, biofilm formation and pathogenicity of the bacteria. Therefore, the flagellar motility is considered as an attractive target for QS AI-2 inhibitors for preventing and/or blocking the infection process. In this study, C1-C8 inhibited APEC O78 motility (FIG. 10B). This result was supported by the inhibitory effect of these compounds on motility-regulating genes (FIG. 14A) such as flgN, motB and flip. Previously, motility inhibitors have been used to control *V. cholera* and *S. typhimurium* that function through down-regulation of flagellar synthesis genes.

It is known that APEC pathogenesis is controlled by a number of virulence factors and inhibition of these virulence factors by QS AI-2 inhibitors can render APEC avirulent and attenuate its pathogenicity. Previously, QSIs such as: furanone C-30 has been reported to control virulence of *P. aeruginosa* through the reduction of QS-regulated virulence factors such as protease, pyoverdin and chitinase and their associated genes; hamamelitannin through the inhibition of *S. aureus* RNAIIIS part of the agr QS system; and virstatin through inhibition of *V. chorerae* virulence factors such as cholera toxin and toxin coregulated pilus. Interestingly, AI-2 inhibitors in this example also down-regulated a group of the virulence associated genes (FIG. 14B) such as adhesion fimC, plays an important role in APEC adherence to the cells through the regulation of adhesion of type 1 fimbriae, iron uptake receptors (fyuA and lucD) which are involved in biofilm formation, iss which plays a role in resistance against serum complements, and vat which regulates the motility, agglutination, and biofilm formation of APEC. This indicated that the AI-2 inhibitors might interfere with bacterial iron acquisition, metabolism, adhesion and invasion, serum survival; thus, modulate APEC infection of host cells. Importantly, all AI-2 inhibitors, except C4 reduced intracellular APEC O78 in chicken and/or human macrophages (FIG. 12A; 12B), enhanced *G. mellonella* survival and reduced APEC load inside (FIG. 13B).

Figure 15:
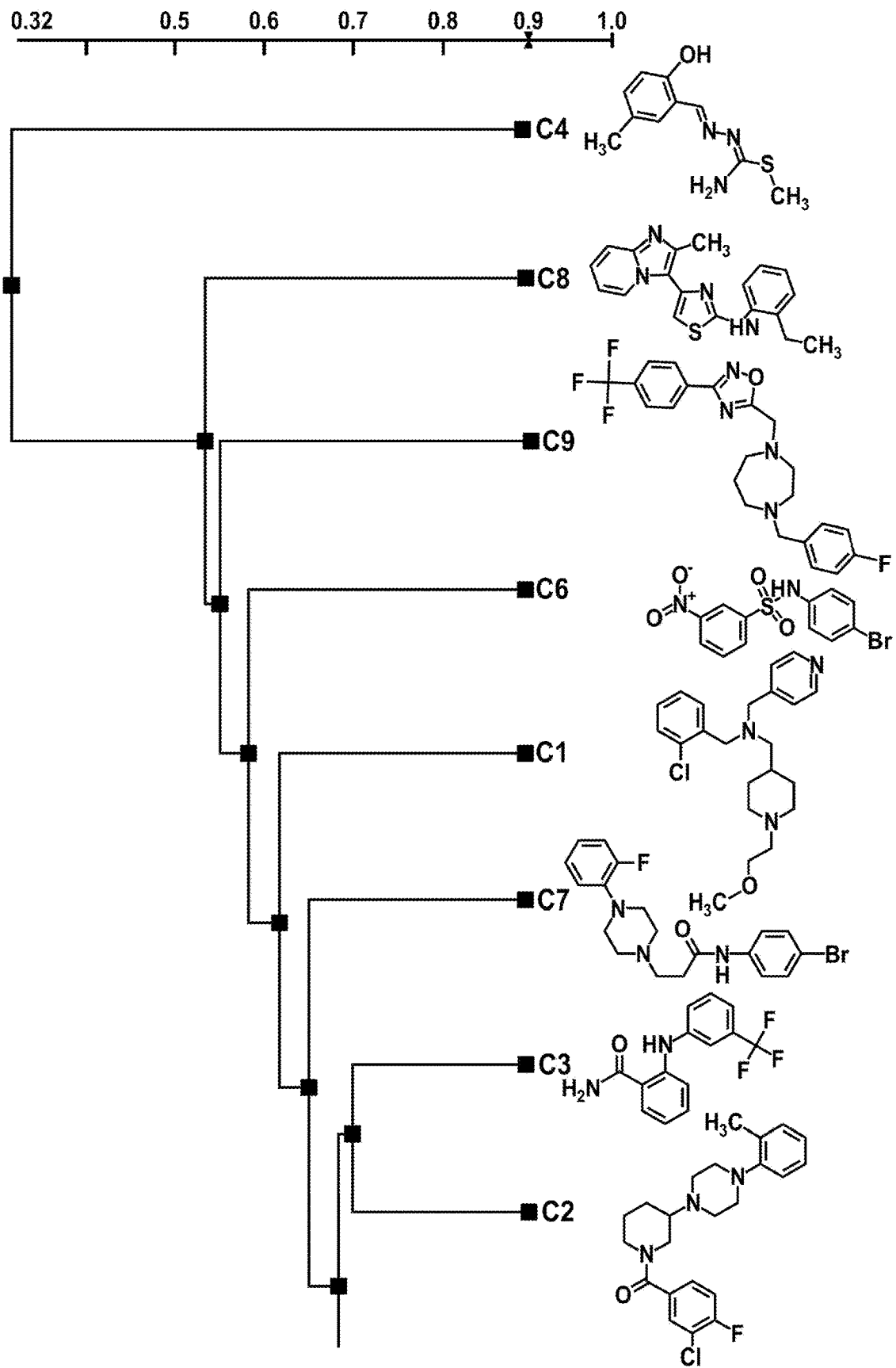
FIG. 15 shows the alignment and the chemical structures of the top 10 AI-2 inhibitors using 2D Tanimoto similarity scoring method. A similarity score of 0.68 is statistically significant at the 95% confidence interval.
Figure 15:
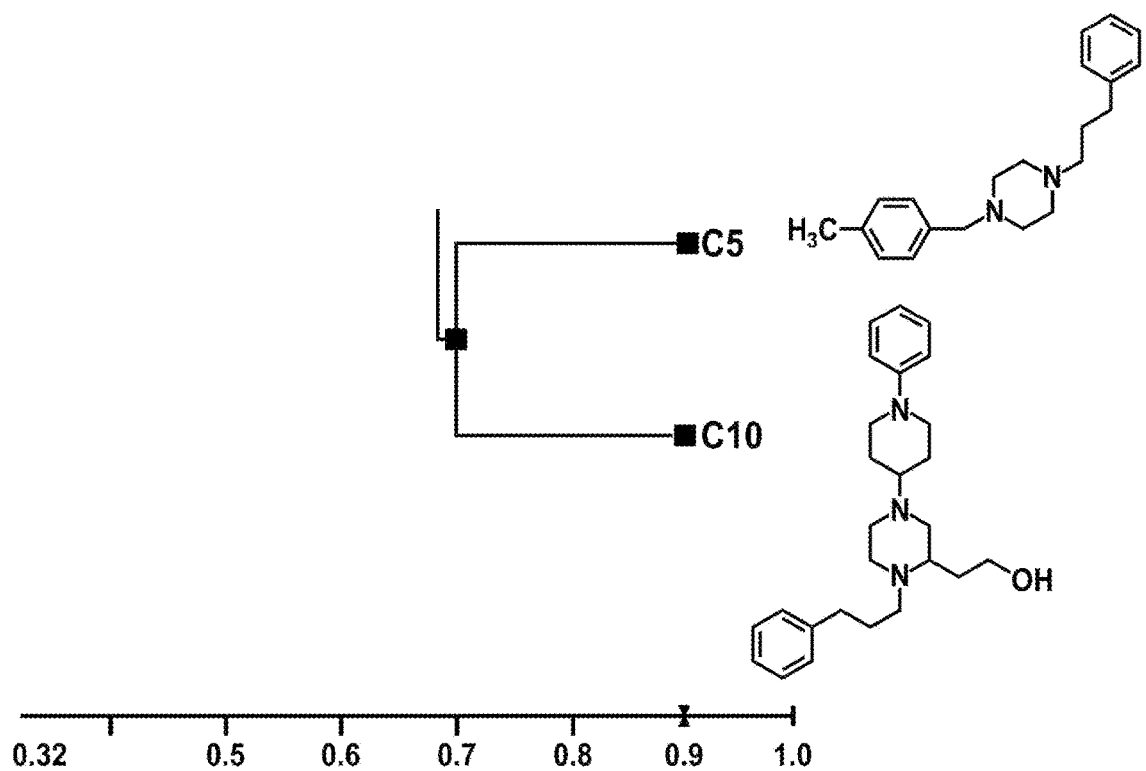

The two-dimensional structure of the 10 selected AI-2 inhibitors was analyzed using a 2D Tanimoto scoring method. The 10 AI-2 inhibitors were divided into two clusters; the large cluster composed of nine compounds (C1-C3 and C5-C10) while the small cluster was formed only by C4 (FIG. 15). All nine compounds within in the larger cluster inhibited the luxS expression while C4 did not, suggesting a potential association between the chemical structure and the mode of action of the compounds in APEC. Four compounds (C2, C3, C5, C10) possess high structural similarities between each other (score=0.71). C5 and C10 are both composed of a phenylpropyl piperazinyl phenyl structure and showed similarity in their effect on expression profile (r>0.4; P<0.05, FIG. 14A; 14B) of QS and virulence associated genes. Interestingly, C5 resulted in greater inhibition of APEC motility compared to C10 (FIG. 10B). C10 also contains piperidinyl and propanol radicals which might explain its lower inhibitory effect on motility. Similarly, both C2 and C10 are composed of a sequence of piperidinyl phenyl piperazinyl groups; however, C2 displayed better in vitro effect compared to C10, while C10 displayed better in vivo efficacy in wax moth compared to C2 (FIG. 13A). These findings suggest that the sequence of phenyl piperazinyl functional groups might be the key groups contributing to the AI-2 inhibitory activity of C2, C5 and C10.

Figure 16:
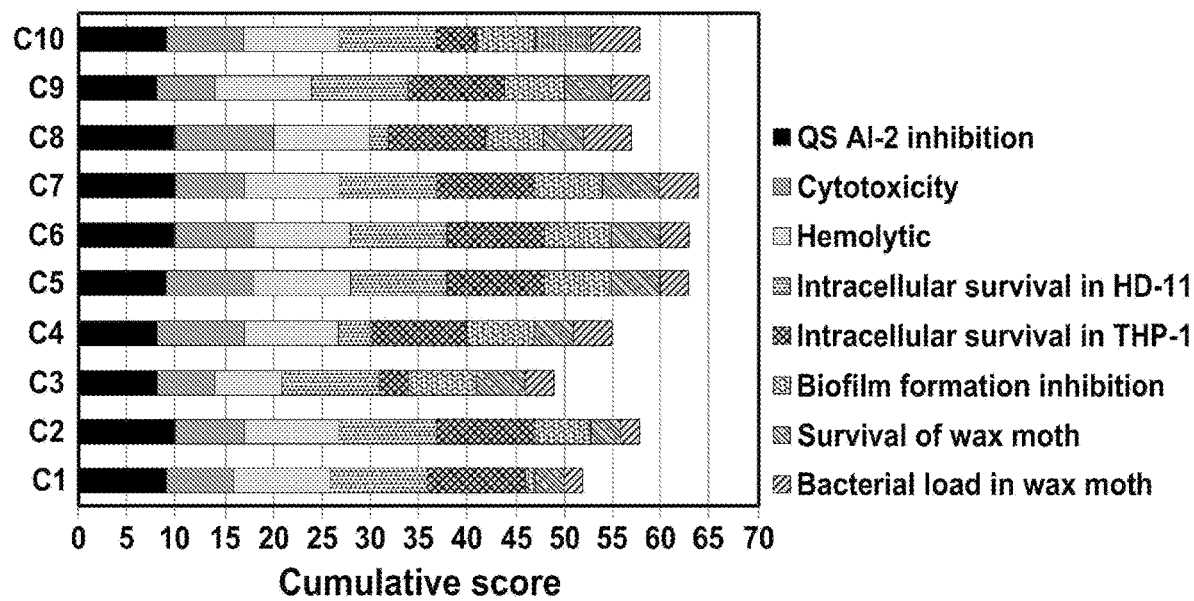
FIG. 16 shows the cumulative scores based on the in vitro and in vivo activities of the AI-2 inhibitors. In vitro (AI-2 inhibition, cytotoxicity, hemolytic activity, intracellular survival in HD11 and THP-1, biofilm formation, survival of wax moth and bacterial load in wax moth) and in vivo (wax moth larval model) effects were scored (1 to 10).

Notably, C5, C6 and C7 possessed highest efficacy in all in vitro assays and also increased the survival of wax moth in vivo (≥50%; score>60; FIG. 16). Although, both C5 and C7 contain piperazinyl functional group (score=0.58), C6 contain nitrobenzene sulfonamide functional group; however, C6 and C7 have some structural similarity (contain 4-bromophenyl group; score=0.59), which could explain their similar effect both in vitro and in vivo. On the other hand, C1, C2 and C10 contain piperidine functional group (score=0.61) but C1 displayed no effect on biofilm formation (FIG. 10A) and lower efficacy in vivo compared to C2 and C10 (FIG. 13A). This might be due to the presence of piperazine functional group in addition to piperidine functional group in both C2 and C10 suggesting that presence of piperazine functional group might contribute to the activity of these compounds. The chemical structures of the AI-2 inhibitors are shown in FIG. 15. Previously, piperazine based derivatives have been reported to inhibit *V. cholera* and *P. aeruginosa* through down-regulation of RND efflux virulence factor and AHL-LasR QS-dependent factors, respectively.

Conclusion

The potential AI-2 inhibitors identified in this example possessed suitable properties in vitro and also differentially affected the expression of QS associated with virulence, biofilm, motility, exopolysaccharide synthesis genes of APEC which likely contributed to APEC survival in vitro (cell culture) and in vivo (wax moth). The C5, C6, C7 displayed highest efficacy in both in vitro and in vivo and activity seems to be related to piperazine based functional group (C2, C5, C7, and C10). Discovery of novel antimicrobials that do not affect the bacterial growth is less likely to impose a selective pressure for resistance development by the bacteria and therefore represent ideal antibiotic independent approach. Further in vivo studies in chickens and target identification of these potential leads will facilitate development of novel therapeutics to augment APEC control in poultry and its potential zoonotic transmission.

Example 3. In Vivo Efficacy of Growth Inhibitors Against APEC

Figure 17A:
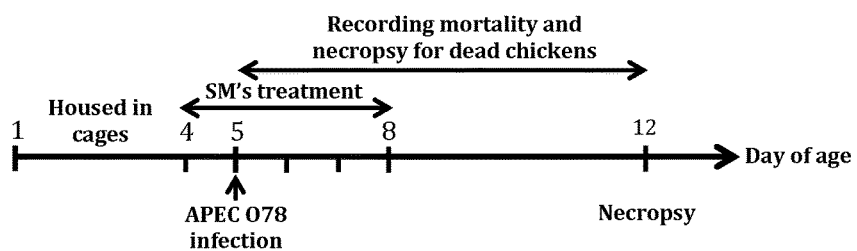
FIG. 17A is a schematic illustration of the experimental design used to evaluate the in vivo activity of growth inhibitors against APEC.

The efficacy of SM's to control APEC infection was assessed using one-day-old broiler chickens (n=6) (Cornish Rock; Meyer Hatchery, Polk, Ohio). After arrival, chickens were housed in cages under required brooding conditions and without further handling for 3 days to allow them to acclimatize in the provided environment. The schematic diagram of the experimental design is displayed in FIG. 17A. SM's were dissolved in water (100 μL) containing 25% DMSO and administered through oral gavage twice a day from day 4 (one day before APEC challenge) to day 8 (3 days post-challenge). The dose of each SM's is described in Table 7. The doses correspond to 50× in vitro MBC of SM's and were also selected based on previous lab experiments. The positive (DMSO treated) and negative (non-infected and non-treated) control chickens were included.

On day 5, chickens were infected subcutaneously (s/c) with rifampicin resistant (Rif$^r$) APEC O78 (1×10$^7$ CFU/chicken) using insulin syringe (1 mL, 27 gauze, 0.5 inch). This dose was selected based on a preliminary study with different infection routes (s/c, intra-tracheal and intra-air-sacs) and doses (10$^6$, 10$^7$ and 10$^8$ CFU/chicken) to determine the appropriate route and dose for APEC infection in chickens. To prepare the APEC inoculum, overnight grown (37° C., 200 rpm) Rif$^r$ APEC O78 (50 μg/mL rifampicin) in LB was grown to logarithmic phase in fresh LB medium, washed twice with PBS and adjusted to 0.1 OD$_{600}$. The clinical signs and mortality of chickens were recorded until 7 days post-infection. Chickens that die during this period were necropsied on the same day, lesions in internal organs (liver, heart, lung, and air-sacs) were scored and the APEC load was quantified in internal organs (liver, heart, lung, and kidney) using MacConkey agar plates containing 50 μg/mL rifampicin. At day 12, all live birds were euthanized, lesions were scored, and the APEC load was quantified on internal organs as described above. The body weight of chickens was measured before the SM's treatment and until the necropsy.

A total of 8 SM's (SM-1, SM-2, SM-3, SM-6, SM-7, SM-8, SM-9 and SM-10) were tested in two independent experiments. Four SM's were included in each trial. Approved husbandry practices were followed throughout the experiments. Feed was provided ad libitum.

TABLE 7

Dose of SM's administered to chickens

| | Weight of SM/chick/dose (μg)† |
|---|---|
| SM-1 | 173.35 |
| SM-2 | 108.65 |
| SM-3 | 99.625 |
| SM-6 | 54.6875 |
| SM-7 | 109.625 |
| SM-8 | 28.5 |
| SM-9 | 90.725 |
| SM-10 | 108.375 |

†equals to 50X in vitro MBC initial concentration in 100 μL oral gavage.

SM's Reduced the Mortality, APEC Lesions Severity and APEC Load in Chickens

Figure 17B:
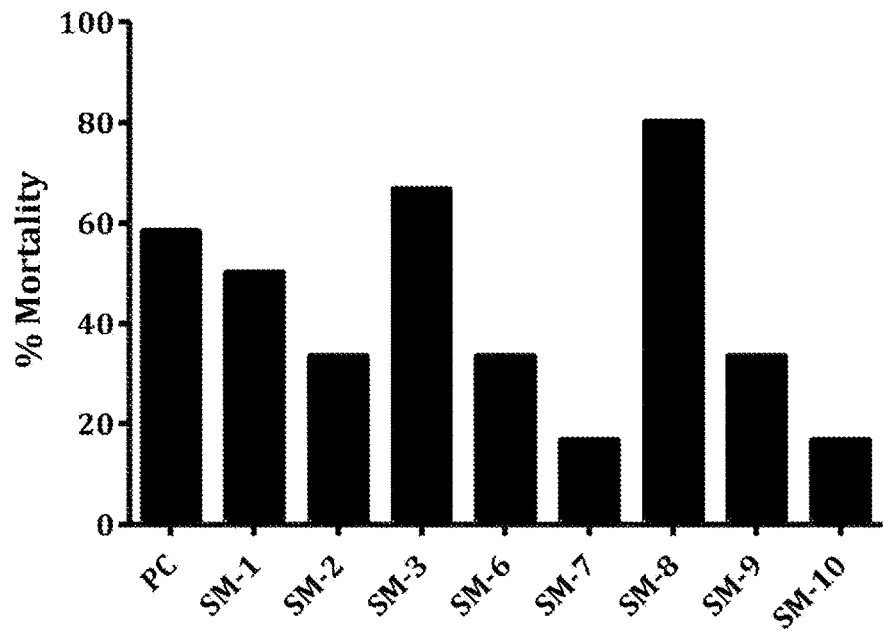
FIG. 17B is a plot showing the impact of various growth inhibitors on the mortality of chickens.

Treatment of APEC infected broiler chickens with SM's, twice a day, for 5 days, reduced the APEC induced mortality of broiler chickens by 42.86% to 71.42% compared to untreated (DMSO treated) control. For calculation of mortality reduction, mortality observed in untreated control (58.34%) was normalized to 100%. The mortality observed in each treatment group is displayed in FIG. 17B. SM-7 and SM-10 reduced the mortality by 71.42%; whereas, SM-2, SM-6 and SM-9 reduced the mortality by 42.86%. Only 14.28% reduction in mortality was observed in SM-1 treated group.

Figure 18B:
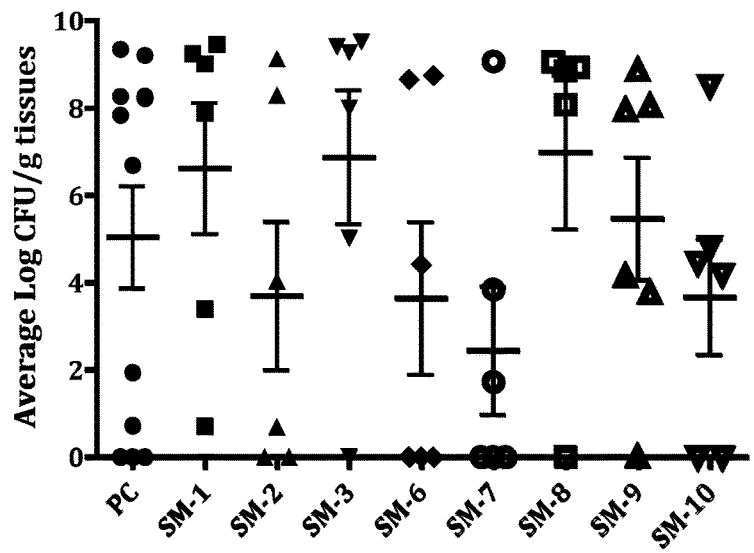
FIG. 18B shows the effect of treatment with growth inhibitors on APEC load in infected chickens.
Figure 18A:
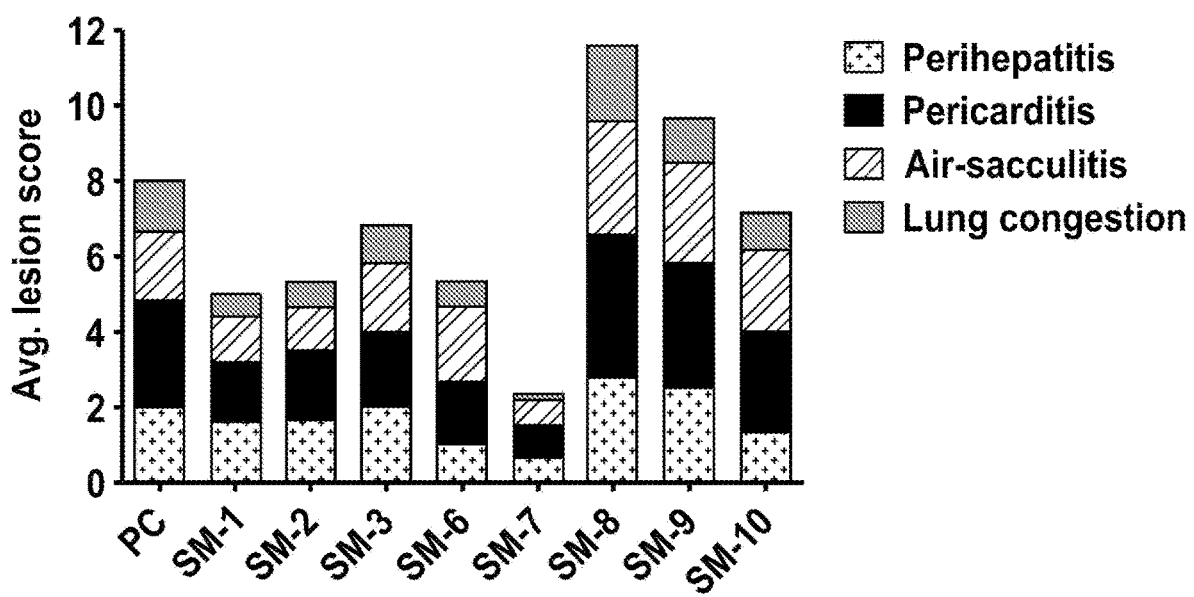
FIG. 18A is a plot summarizing the average lesion score for internal organs (liver, heart, lung and air-sacs) of infected chickens upon treatment with various growth inhibitors.
Figure 19:
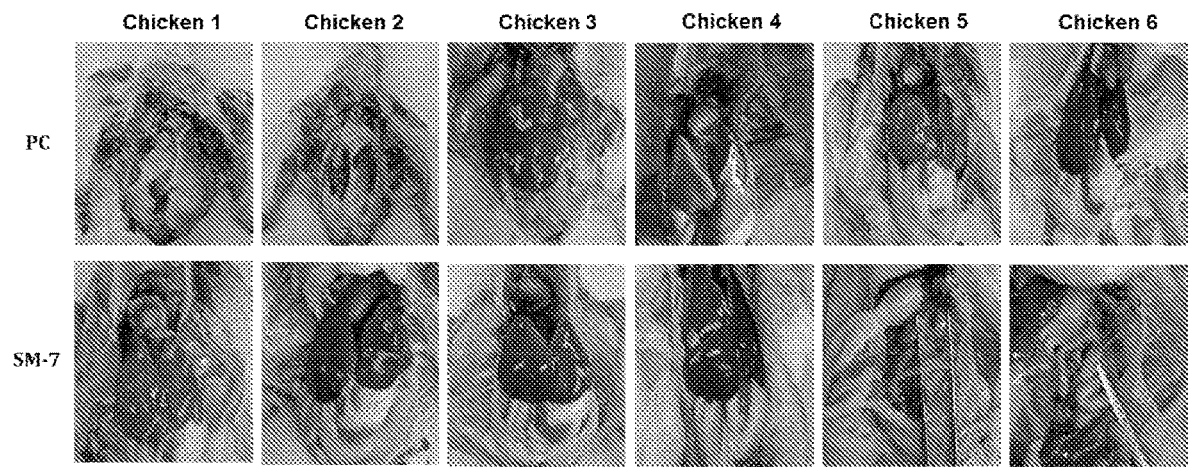
FIG. 19 includes images of representative livers of APEC-infected chickens without treatment and upon treatment with SM-7.

To assess the impact of SM's on APEC induced pathology, severity of APEC lesions in the internal organs (liver, heart, lung and air-sacs) of infected chickens was measured. The average lesions scores were calculated for each group and displayed as cumulative lesions scores (FIG. 18A). The untreated chickens had cumulative lesions score of 6.2; whereas, SM-7 treated chickens had cumulative lesions score of 2.4 (P<0.01). Similarly, SM-2 and SM-6 treated chickens had cumulative lesions score of 5.4 (P≤0.1). The treatment of APEC infected chickens with SM-2, SM-6 and SM-7 reduced the severity of perihepatitis, pericarditis, airsacculitis and lung congestion by 13.5% to 62% in infected chickens. For calculation of lesions severity reduction, lesions scores in untreated control were considered as 100%. In SM-7 treated chickens, the perihepatitis severity was reduced by 60%; whereas, SM-6 and SM-10 reduced 4 by 0% and 20%, respectively (Table 8). Similarly, the pericarditis severity was reduced by 60% in SM-7 treated chickens; whereas; SM-2 and SM-6 reduced by 12% and 20%, respectively. SM-7 also reduced the airsacculitis severity by 52.9%; whereas, SM-2 reduced by 17.7%. Lung congestion was reduced by 83.3% in SM-7 treated chickens; whereas, SM-1, SM-2 and SM-6 reduced by 33.3%. The representative images of gross pathological lesions in internal organs of APEC infected and SM-7 (most effective) treated and untreated chickens are displayed in FIG. 19. Three of the untreated (PC-1, PC-2 and PC-3) chickens showed severe APEC lesions (perihepatitis and pericarditis). Whereas, only one of the SM-7 (SM7-1) treated chickens showed mild APEC lesions.

TABLE 8

SM's reduction of APEC lesions severity (%) in the internal organs of chickens.

|       | Liver | Heart | Lung  | Air-sacs |
|-------|-------|-------|-------|----------|
| SM-1  | −20   | 33.3  | 4     | −5.9     |
| SM-2  | 0     | 33.3  | 12    | 17.7     |
| SM-3  | −20   | 4     | 0     | −29.4    |
| SM-6  | 40    | 20    | 33.3  | −41.2    |
| SM-7  | 60    | 60    | 83.3  | 52.9     |
| SM-8  | −68   | −82.4 | −100  | −111.8   |
| SM-9  | −50   | −60   | −16.7 | −88.2    |
| SM-10 | 20    | −28   | 0     | −52.9    |

To assess the impact of SM's on APEC load, bacterial burden was quantified from different internal organs (liver, heart, lung and kidney) of infected chickens. Treatment of APEC infected broiler chickens with SM-2, SM-6, SM-7 and SM-10 reduced the APEC load in internal organs of infected chickens by 1.3 to 2.6 logs (on an average) as compared to untreated control (FIG. 18B). Average APEC load was calculated by averaging the APEC load from all internal organs. SM-2 and SM-10 reduced the APEC load by 1.3 logs; whereas, SM-6 reduced 1.4 logs and SM-7 reduced 2.6 logs (P≤0.1). In liver, SM-2 reduced 1.3 logs; whereas, SM-6, SM-7 and SM-10 reduced 1.2, 2.5 and 0.8 logs, respectively (Table 9). In lung, SM-2 reduced 1.5 logs; whereas, SM-6, SM-7 and SM-10 reduced 1.2, 2.4 and 1.4 logs, respectively. In heart, SM-2 reduced 0.8 logs; whereas, SM-6, SM-7 and SM-10 reduced 1.3, 2.3 and 1.0 logs, respectively. In kidney, SM-2 reduced 1.8 logs; whereas, SM-6, SM-7 and SM-10 reduced 1.9, 3.2 and 2.4 logs respectively. On the contrary, SM-1, SM-3, SM-8 and SM-9 either exacerbated or did not reduce the APEC load in the internal organs of infected chickens.

None of the SM's affected the BWG of chickens (P>0.05), except SM-2 (Table 10). SM-7 treated group had the indistinguishable BWG as compared to non-treated and non-infected chickens.

TABLE 9

SM's reduction of APEC load (log CFU/g of tissues) in the internal organs of chickens

|       | Liver | Heart | Lung | Kidney |
|-------|-------|-------|------|--------|
| SM-1  | −2.0  | −1.8  | −1.4 | −1.1   |
| SM-2  | 1.2   | 0.8   | 1.5  | 1.8    |
| SM-3  | −1.8  | −2.1  | −2.0 | −1.4   |
| SM-6  | 1.2   | 1.3   | 1.2  | 1.9    |
| SM-7  | 2.5   | 2.3   | 2.4  | 3.2    |
| SM-8  | −2.2  | −2.0  | −2.0 | −1.6   |
| SM-9  | −0.1  | −0.5  | −0.9 | −0.2   |
| SM-10 | 0.8   | 1.0   | 1.4  | 2.4    |

TABLE 10

Body weight gain (BWG) of chickens.

|       | BWG†              |
|-------|-------------------|
| SM-1  | 165.62 ± 69.17    |
| SM-2  | 125.48 ± 34.66[b] |
| SM-3  | 254.58 ± 95.03    |
| SM-6  | 222.18 ± 54.01    |
| SM-7  | 261.30 ± 20.43    |
| SM-8  | 246.82 ± 0.00     |
| SM-9  | 214.93 ± 31.88    |
| SM-10 | 220.75 ± 38.93    |
| NC    | 279.78 ± 13.88[a] |

†weight of live chickens before necropsy was subtracted to weight of chickens before treatment.

Example 4. Screening of Quorum Sensing Inhibitors In Vivo

Seven quorum sensing inhibitors (C1, C2, C5, C6, C7 C8, C10) were evaluated for in vivo activity against APEC. These compounds were selected based on the AI-2 inhibition level in vitro. The efficacy of the SMs to control APEC infection was assessed using one-day-old broiler chickens (n=6) (Cornish Rock; Meyer Hatchery, Polk, Ohio). After arrival, chickens were housed in cages under required brooding conditions and without further handling for 3 days to allow them to acclimatize in the provided environment. SMs were dissolved in water (100 μL) containing 25% DMSO and administered through oral gavage once a day from day 4 (one day before APEC challenge) to day 8 (3 days post-challenge). The dose of each SM's is described in Table 11. The positive (DMSO treated) and negative (non-infected and non-treated) control chickens were included. On day 5, chickens were infected subcutaneously (s/c) with rifampicin resistant (Rif) APEC O78 ($1\times10^7$ CFU/chicken) using insulin syringe (1 mL, 27 gauze, 0.5 inch). This dose was selected based on a preliminary study with different infection routes (s/c, intra-tracheal and intra-airsacs) and doses ($10^6$, $10^7$ and $10^8$ CFU/chicken) to determine the appropriate route and dose for APEC infection in chickens. To prepare the APEC inoculum, overnight grown (37° C., 200 rpm) Rif$^r$ APEC O78 (50 μg/mL rifampicin) in LB was grown to logarithmic phase in fresh LB medium, washed twice with PBS and adjusted to 0.1 $OD_{600}$. The clinical signs and mortality of chickens were recorded until 8 days post-infection. Chickens that die during this period were necropsied on the same day, lesions in internal organs (liver, heart, lung, and air-sacs) were scored and the APEC load was quantified in internal organs (liver, heart, lung, and kidney) using MacConkey agar plates containing 50 μg/mL rifampicin. At day 12, all live birds were euthanized, lesions were scored, and the APEC load was quantified on internal organs as described above. The body weight of chickens was measured before the SM's treatment and until the necropsy. Approved husbandry practices were followed throughout the experiments. Feed was provided ad libitum.

TABLE 11

Treatment groups and the dose of each AI-2 inhibitors

| Groups           | SM dose  | APEC O78 |
|------------------|----------|----------|
| C1               | 116.4    | Yes      |
| C2               | 128      | Yes      |
| C5               | 92.6     | Yes      |
| C6               | 107.2    | Yes      |
| C7               | 121.89   | Yes      |
| C8               | 100.32   | Yes      |
| C10              | 122.28   | Yes      |
| Positive control | 25% DMSO | Yes      |
| Negative control | None     | Yes      |

Figure 20A:
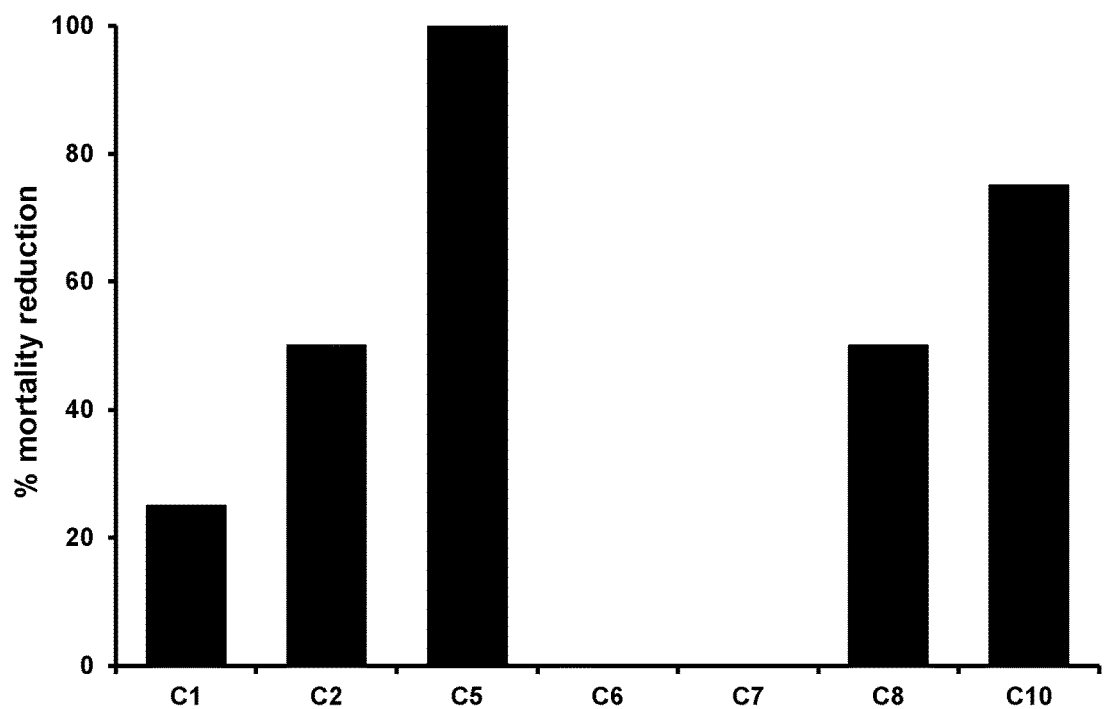
FIG. 20A-20D show the effect of QS AI-2 inhibitors on APEC-infected chickens.
Figure 20B:
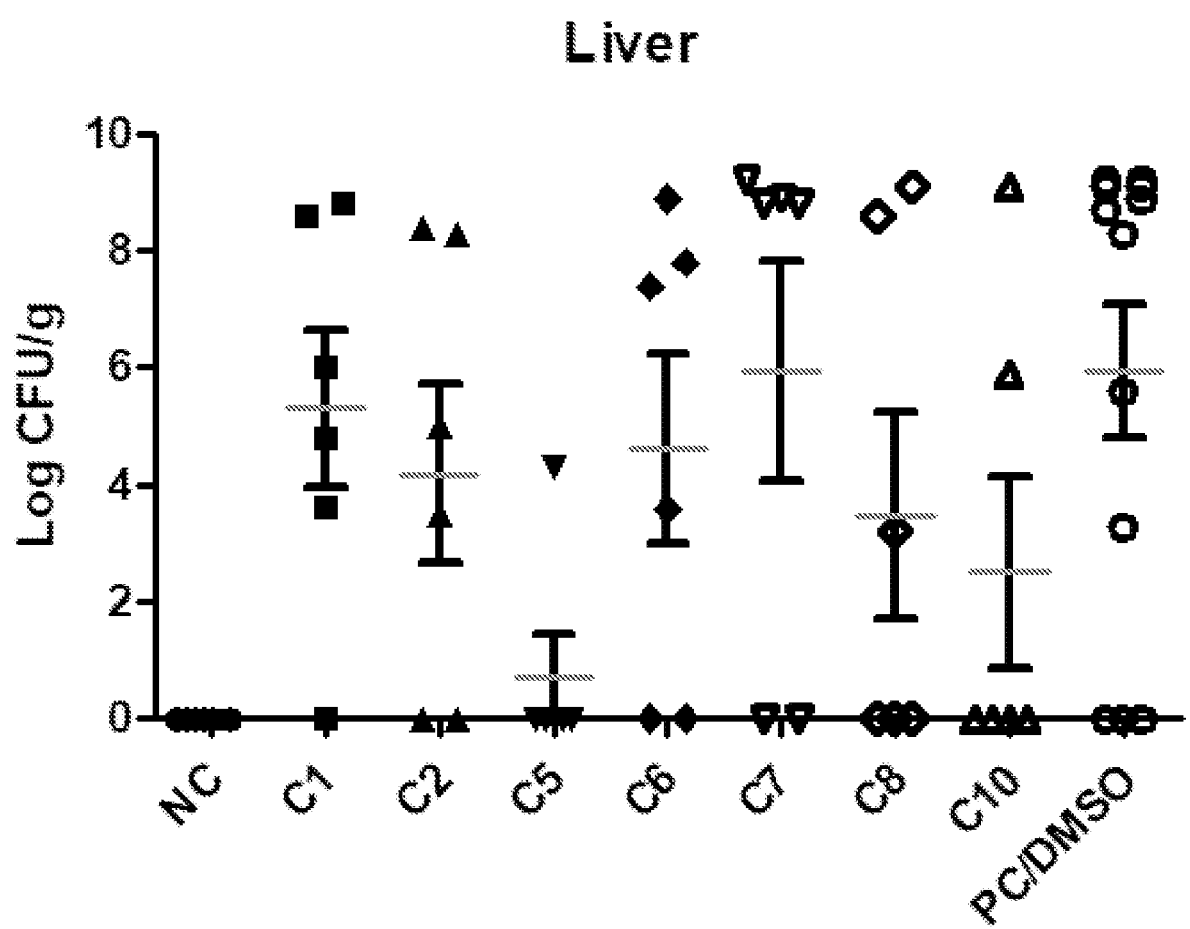
Figure 20C:
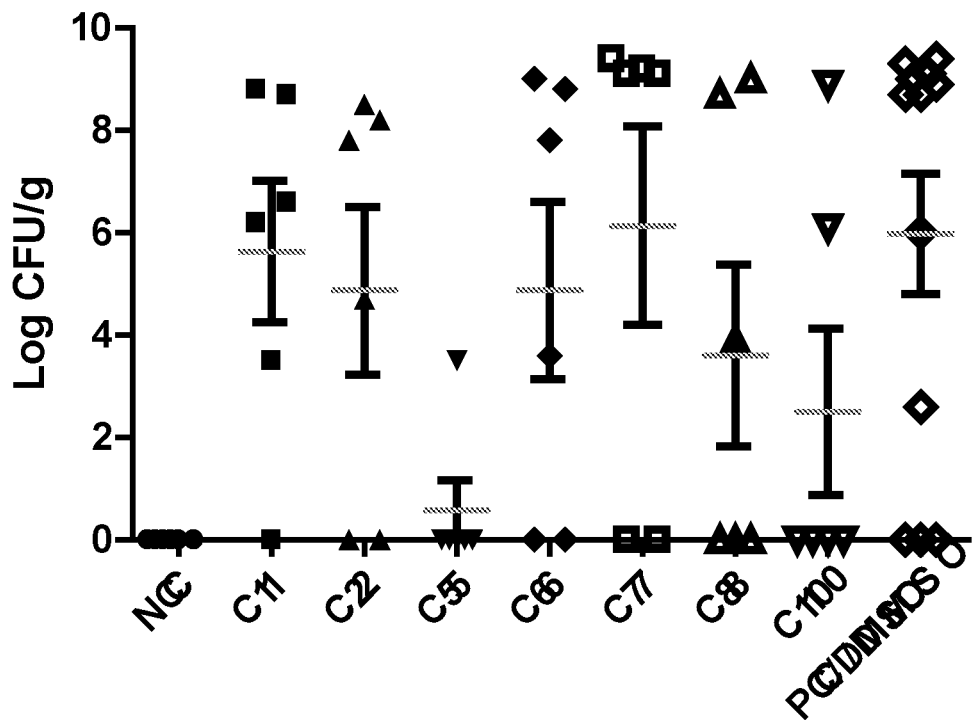
Figure 20D:
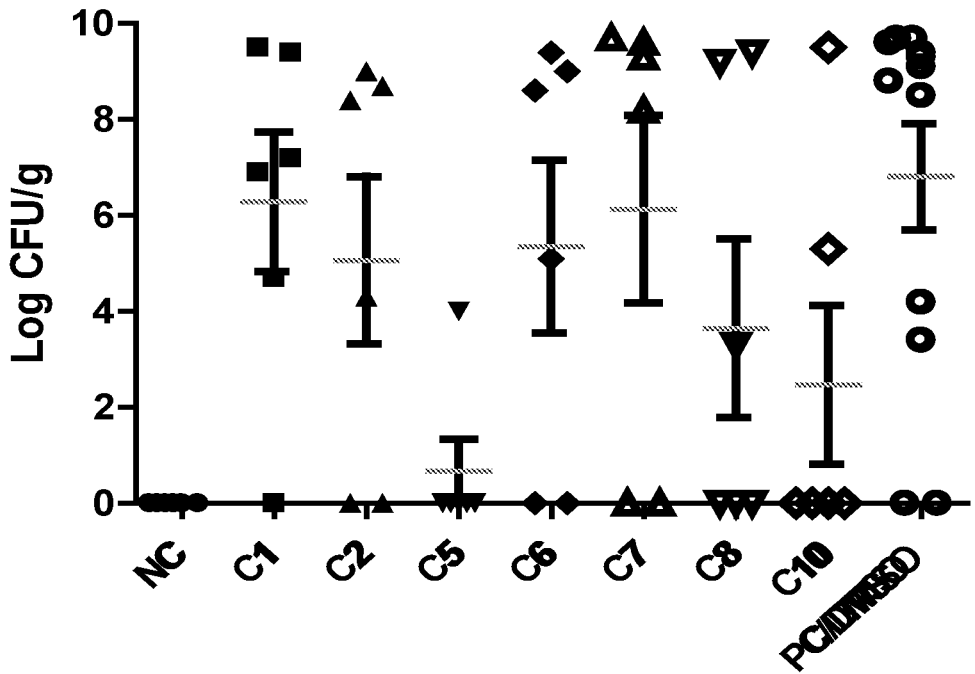
Figure 20E:
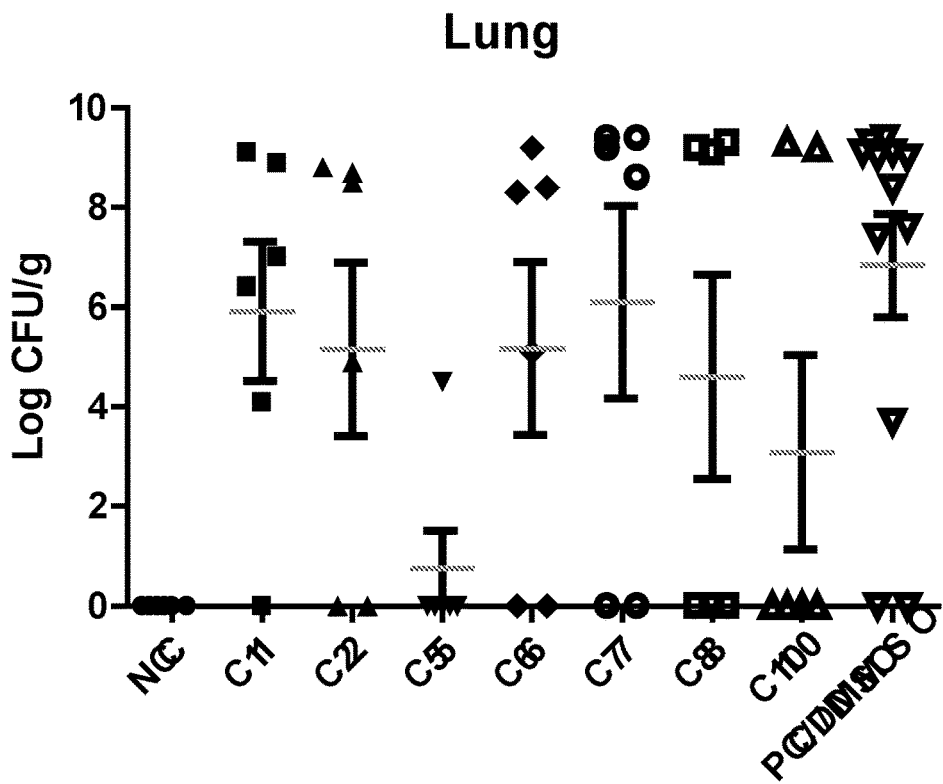
Figure 20F:
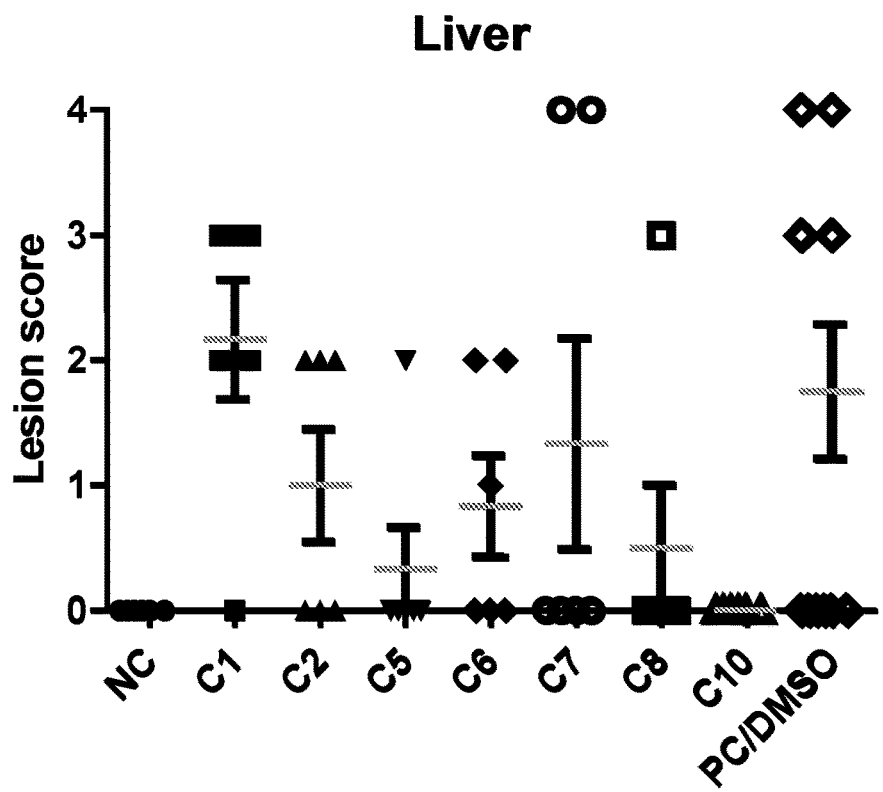
FIG. 20F-20I is a plot showing APEC lesion severity in the internal organs (liver (FIG. 20F), heart (FIG. 20G), airsacs (FIG. 20H), and lung (FIG. 20I)) of compounds treated groups compared to DMSO control group.
Figure 20G:
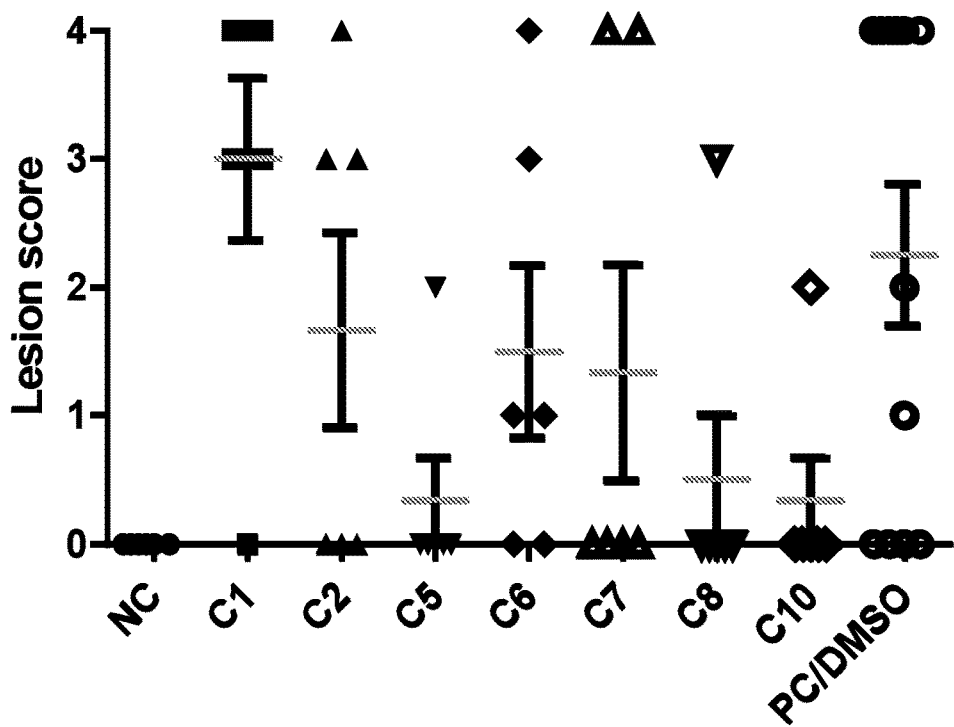
Figure 20H:
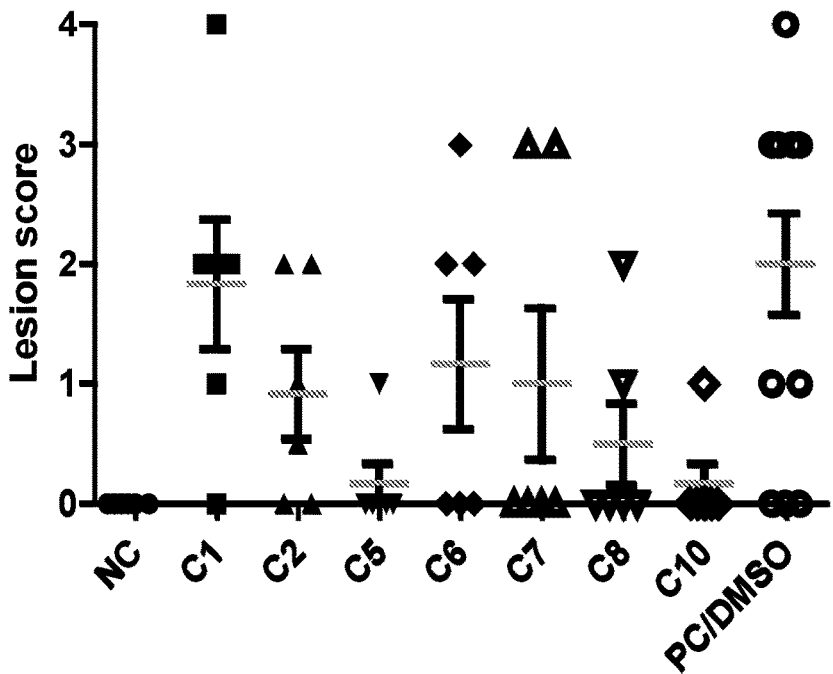
Figure 20I:
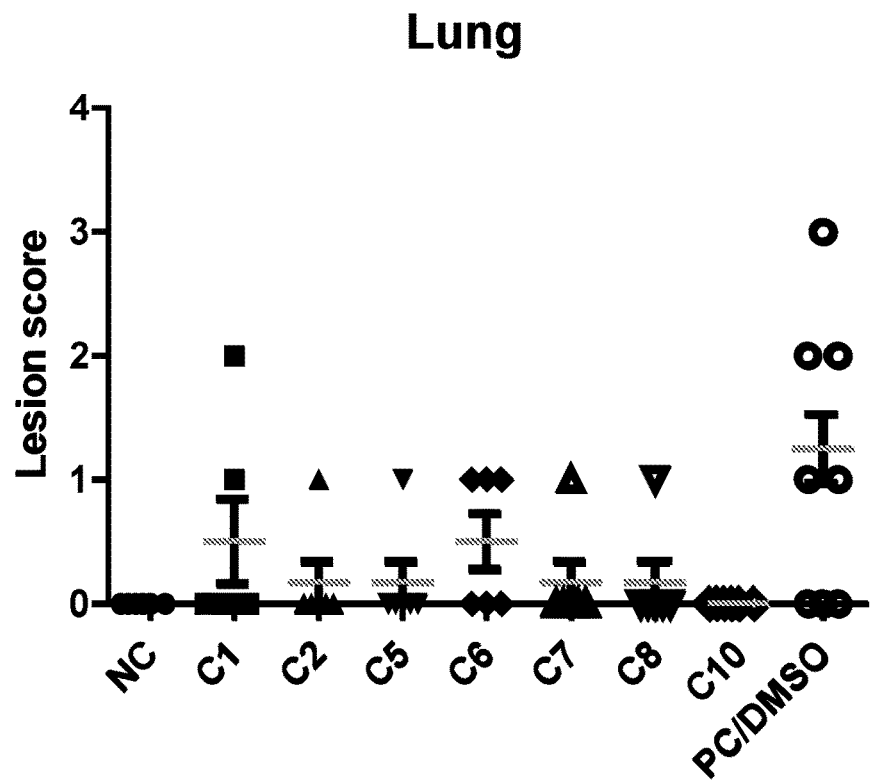

SMs Reduced the Mortality, APEC Load and Pathological Lesions Severity in Chickens Treatment of APEC-infected chickens with C5 resulted in 0% mortality in comparison to 66.7% mortality in the DMSO treated control group; while treatment with C10 resulted in 16.6% mortality. Further, treatment of chickens with C2 and C8 resulted in 33.3% mortality; while treatment with C1 resulted in 50% mortality. Treatment of chickens with C6 and C7 resulted in 66.7% mortality (Table 12). After normalization of the mortality in the DMSO control group to 100%, we found that treatment of the infected chickens with C5 and C10 resulted in 100% and 75% reduction in chicken mortality, respectively; while C2 and C8 resulted in a 50% reduction in chicken's mortality in comparison to DMSO treated control. The treatment with C1 resulted in a 25% reduction in the chicken's mortality, while C6 and C7 did not reduce chicken's mortality in comparison to DMSO treated control (FIG. 20A).

TABLE 12

Mortality rate in APEC- treated chickens

| | C1 | C2 | C5 | C6 | C7 | C8 | C10 | DMSO |
|---|---|---|---|---|---|---|---|---|
| Mortality rate (%) | 50 | 33.3 | 0 | 66.7 | 66.7 | 33.3 | 16.6 | 66.7 |

Treatment of chickens with C5 and C10 reduced the bacterial load up to 5.2-6.1 logs and 3.4-4.3 log CFU/g, respectively in internal organs (liver, lung, heart, and kidney) compared to the DMSO control group; while treatment of chickens with C8 reduced the bacterial load up to 2.2-3.1 log CFU/g comparing to the DMSO control group. Further, C2 and C6 reduced the APEC load up to 1.1-1.8 log CFU/g in infected chickens (FIGS. 20B-20E).

To assess the impact of SMs on the severity of pathological lesions caused by APEC in the internal organs (liver, heart, lung and airsac) of infected chickens, the average lesions scores were calculated for each group and compared to the DMSO treated control group. The average lesion score reduction was (2.1-2.3) and (1.5-2.3) in C5 and C10 treated groups, respectively in comparison to DMSO treated group; while the average lesion score reduction was (0.5-1.6) in C2 and C7 treated groups. The average lesion score reduction was (0.7-1.3) and (1.0-2.0) in C6 and C8 treated groups, respectively in comparison to DMSO treated group (FIGS. 20F-20I). Additionally, for calculation of lesions severity reduction, lesions scores in DMSO treated control group were considered as 100%. Treatment of chickens with C5 reduced the severity of pathological lesions between 78% and 93% in internal organs (liver, heart, lung and airsac) in comparison to DMSO treated control; while the reduction in pathological lesions in the C10 treated group was 83.3% to 100% in comparison to DMSO treated control. Treatment of chickens with C8 resulted in 66.7 to 83.3% reduction in the pathological lesions severity (Table 13).

Figure 20J:
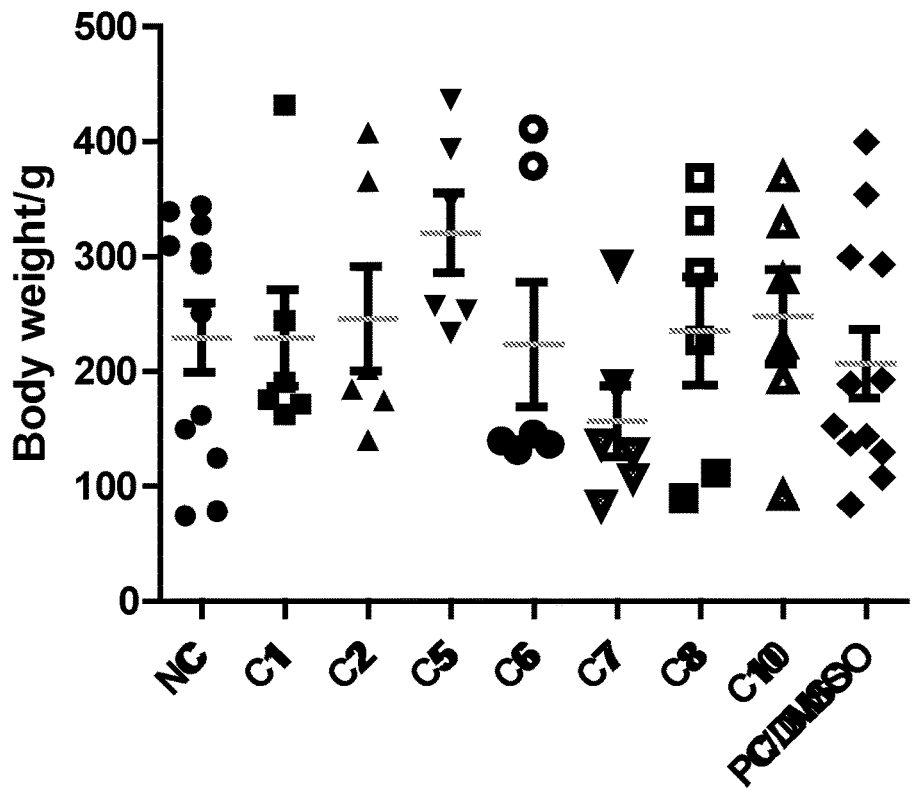
FIG. 20J is a plot summarizing body weight gain. *Significant difference between treated chickens ($P<0.05$) and DMSO control group.

None of the SM's affected the body weight gain of treated chickens, except C5. Treatment of the chickens with C5 increased BWG (P>0.05) in comparison to non-treated and non-infected control group (FIG. 20J).

TABLE 13

Reduction in APEC lesions severity (%) in the internal organs of chickens in comparison to DMSO treated control.

| | Liver (%) | Lung (%) | Heart (%) | Air-sacs (%) |
|---|---|---|---|---|
| C1 | 0 | 66.7 | 0 | 26.7 |
| C2 | 45.5 | 88.9 | 37.5 | 63.3 |
| C5 | 81.8 | 88.9 | 87.5 | 93.3 |
| C6 | 54.5 | 66.7 | 43.8 | 53.3 |
| C7 | 33.3 | 83.3 | 33.3 | 33.3 |
| C8 | 75 | 83.3 | 75 | 66.7 |
| C10 | 100 | 100 | 83.3 | 88.9 |

The compounds, compositions and methods of the appended claims are not limited in scope by the specific compounds, compositions and methods described herein, which are intended as illustrations of a few aspects of the claims. Any compounds, compositions and methods that are functionally equivalent are intended to fall within the scope of the claims. Various modifications of the compounds, compositions and methods in addition to those shown and described herein are intended to fall within the scope of the appended claims. Further, while only certain representative compounds, compositions, components, and method steps disclosed herein are specifically described, other combinations of the compounds, compositions, components, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A method of treating or preventing a bacterial infection in an avian subject, the method comprising administering a therapeutically effective amount of an anti-APEC agent to the avian subject, wherein the anti-APEC agent is a growth inhibitor defined by Formula I, wherein Formula I is defined by the structure below

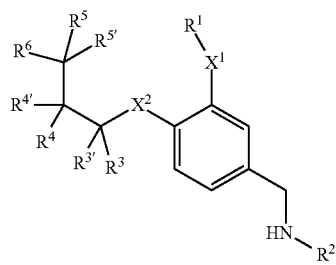

Formula I or a pharmaceutically acceptable salt, ester, or prodrug thereof, wherein $X^1$ and $X^2$ are independent selected from —O— and —S—;

$R^1$ is selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^x$ groups;

$R^2$ is —$(CR^7R^{7'})_nR^8$;

$R^3$, $R^{3'}$, $R^4$, $R^{4'}$, $R^5$, and $R^{5'}$ are each selected from H, OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkyl sulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^6$ is selected from a $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^x$ groups;

each $R^7$ and $R^{7'}$, when present, are each independently selected from H, OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkyl sulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^8$ is selected from $C_{3-10}$ cycloalkyl, $C_{6-10}$ aryl, 4-10 membered heterocycloalkyl, and 5-10 membered heteroaryl, wherein the $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^X$ groups;

each $R^X$, when present, are each independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkyl sulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5.

2. The method of claim 1, wherein the bacterial infection comprises avian pathogenic *E. coli* (APEC).

3. The method of claim 1, wherein the method further comprises administering an antibiotic selected from a tetracycline, a sulfonamide, an aminoglycoside, a β-lactam antimicrobial, a quinolone, and a combination thereof to the avian subject.

4. The method of claim 1, wherein the method further comprises administering a therapeutically effective amount of a quorum sensing inhibitor.

5. The method of claim 1, wherein administering the therapeutically effective amount of the anti-APEC agent to avian subject comprises adding the therapeutically effective amount of the anti-APEC agent to feed consumed by the avian subject.

6. The method of claim 1, wherein administering the therapeutically effective amount of the anti-APEC agent to the avian subject poultry flock comprises adding the therapeutically effective amount of the anti-APEC agent to water consumed by the avian subject.

7. The method of claim 1, wherein the avian subject comprises a chicken.

8. The method of claim 7, wherein the chicken comprises a broiler.

9. The method of claim 7, wherein the chicken comprises a layer.

10. The method of claim 1, wherein the avian subject comprises a turkey.

11. The method of claim 1, wherein $X^1$ and $X^2$ are both O.

12. The method of claim 1, wherein $R_1$ is $C_{1-6}$ alkyl.

13. The method of claim 12, wherein $R^1$ is methyl.

14. The method of claim 1, wherein $R^3$, $R^{3'}$, $R^5$, and $R^{5'}$ are all H.

15. The method of claim 1, wherein $R^4$ is selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkyl sulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and $R^{4'}$ is H.

16. The method of claim 15, wherein $R^4$ is OH and $R^{4'}$ is H.

17. The method of claim 1, wherein $R^6$ comprises a $C_5$ cycloalkyl group or a 5-membered heterocycloalkyl group.

18. The method of claim 17, wherein $R^6$ comprises a pyrrolidine ring.

19. The method of claim 1, wherein
n is 1 or 2;
$R^7$ and $R^{7'}$ are H in all occurrences;
$R^8$ comprises a $C_{6-10}$ aryl ring optionally substituted by 1, 2, 3, or 4 independently selected $R^X$ groups; and
$R^X$, when present, is selected from halo, $C_{1-6}$ alkyl, and $C_{1-4}$ haloalkyl.

20. The method of claim 19, wherein $R^8$ comprises a phenyl ring optionally substituted by 1, 2, 3, or 4 independently selected $R^X$ groups.

21. The method of claim 1, wherein the anti-APEC agent comprises SM7, the structure of which is shown below

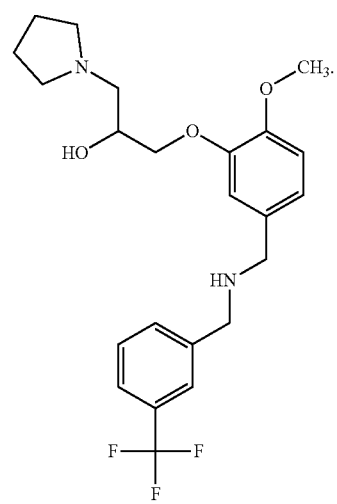 [SMILES: COc1ccc(CNCc2cccc(C(F)(F)F)c2)cc1OCC(O)CN1CCCC1]

* * * * *

SEQUENCE LISTING

<160> NUMBER OF SEQ ID NOS: 56

<210> SEQ ID NO 1
<211> LENGTH: 20
<212> TYPE: DNA
<213> ORGANISM: Artificial Sequence

```
<220> FEATURE:
<223> OTHER INFORMATION: synthetic construct

<400> SEQUENCE: 1
acgagtgcat ctggtaagtg                                              20

<210> SEQ ID NO 2
<211> LENGTH: 21
<212> TYPE: DNA
<213> ORGANISM: Artificial Sequence
<220> FEATURE:
<223> OTHER INFORMATION: synthetic construct

<400> SEQUENCE: 2
caatggaaga cgtgctgaaa g                                            21

<210> SEQ ID NO 3
<211> LENGTH: 22
<212> TYPE: DNA
<213> ORGANISM: Artificial Sequence
<220> FEATURE:
<223> OTHER INFORMATION: synthetic construct

<400> SEQUENCE: 3
cggcagaacc ggtgttaata at                                           22

<210> SEQ ID NO 4
<211> LENGTH: 21
<212> TYPE: DNA
<213> ORGANISM: Artificial Sequence
<220> FEATURE:
<223> OTHER INFORMATION: synthetic construct

<400> SEQUENCE: 4
tgaaatcggg catcggtaaa g                                            21

<210> SEQ ID NO 5
<211> LENGTH: 20
<212> TYPE: DNA
<213> ORGANISM: Artificial Sequence
<220> FEATURE:
<223> OTHER INFORMATION: synthetic construct

<400> SEQUENCE: 5
gtgatctgcg gctgagtaaa                                              20

<210> SEQ ID NO 6
<211> LENGTH: 18
<212> TYPE: DNA
<213> ORGANISM: Artificial Sequence
<220> FEATURE:
<223> OTHER INFORMATION: synthetic construct

<400> SEQUENCE: 6
acgtcgttgc cagacaat                                                18

<210> SEQ ID NO 7
<211> LENGTH: 21
<212> TYPE: DNA
<213> ORGANISM: Artificial Sequence
<220> FEATURE:
<223> OTHER INFORMATION: synthetic construct

<400> SEQUENCE: 7
tcgttatccc agtgaccaaa c                                            21
```

<210> SEQ ID NO 8
<211> LENGTH: 21
<212> TYPE: DNA
<213> ORGANISM: Artificial Sequence
<220> FEATURE:
<223> OTHER INFORMATION: synthetic construct

<400> SEQUENCE: 8
gtgtcgcaac tatgacctga t                                              21

<210> SEQ ID NO 9
<211> LENGTH: 21
<212> TYPE: DNA
<213> ORGANISM: Artificial Sequence
<220> FEATURE:
<223> OTHER INFORMATION: synthetic construct

<400> SEQUENCE: 9
cggttggctg tcgatgtata a                                              21

<210> SEQ ID NO 10
<211> LENGTH: 22
<212> TYPE: DNA
<213> ORGANISM: Artificial Sequence
<220> FEATURE:
<223> OTHER INFORMATION: synthetic construct

<400> SEQUENCE: 10
aggtatattg cagacccgtt tc                                             22

<210> SEQ ID NO 11
<211> LENGTH: 22
<212> TYPE: DNA
<213> ORGANISM: Artificial Sequence
<220> FEATURE:
<223> OTHER INFORMATION: synthetic construct

<400> SEQUENCE: 11
caagtacatc aagcgccatt tc                                             22

<210> SEQ ID NO 12
<211> LENGTH: 24
<212> TYPE: DNA
<213> ORGANISM: Artificial Sequence
<220> FEATURE:
<223> OTHER INFORMATION: synthetic construct

<400> SEQUENCE: 12
cccttcgata tccagatcca atac                                           24

<210> SEQ ID NO 13
<211> LENGTH: 22
<212> TYPE: DNA
<213> ORGANISM: Artificial Sequence
<220> FEATURE:
<223> OTHER INFORMATION: synthetic construct

<400> SEQUENCE: 13
aggctaatac ggttgggaat ac                                             22

<210> SEQ ID NO 14
<211> LENGTH: 21
<212> TYPE: DNA
<213> ORGANISM: Artificial Sequence
<220> FEATURE:
<223> OTHER INFORMATION: synthetic construct

```
<400> SEQUENCE: 14
agaatcgccc gatgtttaga a                                              21

<210> SEQ ID NO 15
<211> LENGTH: 21
<212> TYPE: DNA
<213> ORGANISM: Artificial Sequence
<220> FEATURE:
<223> OTHER INFORMATION: synthetic construct

<400> SEQUENCE: 15
ccagtaacca gccgttatgt t                                              21

<210> SEQ ID NO 16
<211> LENGTH: 22
<212> TYPE: DNA
<213> ORGANISM: Artificial Sequence
<220> FEATURE:
<223> OTHER INFORMATION: synthetic construct

<400> SEQUENCE: 16
tacgcaggaa agaacccaat ac                                             22

<210> SEQ ID NO 17
<211> LENGTH: 20
<212> TYPE: DNA
<213> ORGANISM: Artificial Sequence
<220> FEATURE:
<223> OTHER INFORMATION: synthetic construct

<400> SEQUENCE: 17
agccattcag cgaagagaaa                                                20

<210> SEQ ID NO 18
<211> LENGTH: 22
<212> TYPE: DNA
<213> ORGANISM: Artificial Sequence
<220> FEATURE:
<223> OTHER INFORMATION: synthetic construct

<400> SEQUENCE: 18
gtctggcaaa caaccctaaa tc                                             22

<210> SEQ ID NO 19
<211> LENGTH: 20
<212> TYPE: DNA
<213> ORGANISM: Artificial Sequence
<220> FEATURE:
<223> OTHER INFORMATION: synthetic construct

<400> SEQUENCE: 19
catccacctg gctgaactta                                                20

<210> SEQ ID NO 20
<211> LENGTH: 20
<212> TYPE: DNA
<213> ORGANISM: Artificial Sequence
<220> FEATURE:
<223> OTHER INFORMATION: synthetic construct

<400> SEQUENCE: 20
gtaacacgga ttgcgaacac                                                20

<210> SEQ ID NO 21
```

<211> LENGTH: 21
<212> TYPE: DNA
<213> ORGANISM: Artificial Sequence
<220> FEATURE:
<223> OTHER INFORMATION: synthetic construct

<400> SEQUENCE: 21
gcatcgtcac aaccacaaat c                                             21

<210> SEQ ID NO 22
<211> LENGTH: 20
<212> TYPE: DNA
<213> ORGANISM: Artificial Sequence
<220> FEATURE:
<223> OTHER INFORMATION: synthetic construct

<400> SEQUENCE: 22
ggtttgaacg accagctaca                                               20

<210> SEQ ID NO 23
<211> LENGTH: 20
<212> TYPE: DNA
<213> ORGANISM: Artificial Sequence
<220> FEATURE:
<223> OTHER INFORMATION: synthetic construct

<400> SEQUENCE: 23
tgaccgaaac ggtaggaaac                                               20

<210> SEQ ID NO 24
<211> LENGTH: 21
<212> TYPE: DNA
<213> ORGANISM: Artificial Sequence
<220> FEATURE:
<223> OTHER INFORMATION: synthetic construct

<400> SEQUENCE: 24
ggaataccag tggaccaaca a                                             21

<210> SEQ ID NO 25
<211> LENGTH: 22
<212> TYPE: DNA
<213> ORGANISM: Artificial Sequence
<220> FEATURE:
<223> OTHER INFORMATION: synthetic construct

<400> SEQUENCE: 25
gctggcaggt atcctgatat tc                                            22

<210> SEQ ID NO 26
<211> LENGTH: 20
<212> TYPE: DNA
<213> ORGANISM: Artificial Sequence
<220> FEATURE:
<223> OTHER INFORMATION: synthetic construct

<400> SEQUENCE: 26
tgccctgccg gataaattac                                               20

<210> SEQ ID NO 27
<211> LENGTH: 20
<212> TYPE: DNA
<213> ORGANISM: Artificial Sequence
<220> FEATURE:
<223> OTHER INFORMATION: synthetic construct

```
<400> SEQUENCE: 27
gtccggagaa gcctgaaata                                              20

<210> SEQ ID NO 28
<211> LENGTH: 20
<212> TYPE: DNA
<213> ORGANISM: Artificial Sequence
<220> FEATURE:
<223> OTHER INFORMATION: synthetic construct

<400> SEQUENCE: 28
gagaagcggc ggaaataaac                                              20

<210> SEQ ID NO 29
<211> LENGTH: 22
<212> TYPE: DNA
<213> ORGANISM: Artificial Sequence
<220> FEATURE:
<223> OTHER INFORMATION: synthetic construct

<400> SEQUENCE: 29
cttcccttcc ggttcgttaa tc                                           22

<210> SEQ ID NO 30
<211> LENGTH: 22
<212> TYPE: DNA
<213> ORGANISM: Artificial Sequence
<220> FEATURE:
<223> OTHER INFORMATION: synthetic construct

<400> SEQUENCE: 30
ggtacagccc aaacaccata tc                                           22

<210> SEQ ID NO 31
<211> LENGTH: 21
<212> TYPE: DNA
<213> ORGANISM: Artificial Sequence
<220> FEATURE:
<223> OTHER INFORMATION: synthetic construct

<400> SEQUENCE: 31
cgctctggca atgcttatta c                                            21

<210> SEQ ID NO 32
<211> LENGTH: 22
<212> TYPE: DNA
<213> ORGANISM: Artificial Sequence
<220> FEATURE:
<223> OTHER INFORMATION: synthetic construct

<400> SEQUENCE: 32
gaaatgatgg gtgatggttt cc                                           22

<210> SEQ ID NO 33
<211> LENGTH: 20
<212> TYPE: DNA
<213> ORGANISM: Artificial Sequence
<220> FEATURE:
<223> OTHER INFORMATION: synthetic construct

<400> SEQUENCE: 33
ctgaaccgcg tccagattat                                              20

<210> SEQ ID NO 34
```

```
<211> LENGTH: 20
<212> TYPE: DNA
<213> ORGANISM: Artificial Sequence
<220> FEATURE:
<223> OTHER INFORMATION: synthetic construct

<400> SEQUENCE: 34
actccacggc aggaaatatg                                              20

<210> SEQ ID NO 35
<211> LENGTH: 22
<212> TYPE: DNA
<213> ORGANISM: Artificial Sequence
<220> FEATURE:
<223> OTHER INFORMATION: synthetic construct

<400> SEQUENCE: 35
cagtactttA gcggaggaac tc                                           22

<210> SEQ ID NO 36
<211> LENGTH: 21
<212> TYPE: DNA
<213> ORGANISM: Artificial Sequence
<220> FEATURE:
<223> OTHER INFORMATION: synthetic construct

<400> SEQUENCE: 36
caacccttcc cactccttaa t                                            21

<210> SEQ ID NO 37
<211> LENGTH: 22
<212> TYPE: DNA
<213> ORGANISM: Artificial Sequence
<220> FEATURE:
<223> OTHER INFORMATION: synthetic construct

<400> SEQUENCE: 37
ccggtctgaa agagacgtta at                                           22

<210> SEQ ID NO 38
<211> LENGTH: 19
<212> TYPE: DNA
<213> ORGANISM: Artificial Sequence
<220> FEATURE:
<223> OTHER INFORMATION: synthetic construct

<400> SEQUENCE: 38
ttccgcaacc tcgcattat                                               19

<210> SEQ ID NO 39
<211> LENGTH: 21
<212> TYPE: DNA
<213> ORGANISM: Artificial Sequence
<220> FEATURE:
<223> OTHER INFORMATION: synthetic construct

<400> SEQUENCE: 39
gtaactggac tgctgggatt t                                            21

<210> SEQ ID NO 40
<211> LENGTH: 21
<212> TYPE: DNA
<213> ORGANISM: Artificial Sequence
<220> FEATURE:
<223> OTHER INFORMATION: synthetic construct
```

<400> SEQUENCE: 40
ccaggtacgt attggcgtaa a                                              21

<210> SEQ ID NO 41
<211> LENGTH: 21
<212> TYPE: DNA
<213> ORGANISM: Artificial Sequence
<220> FEATURE:
<223> OTHER INFORMATION: synthetic construct

<400> SEQUENCE: 41
gcgtggttaa tgctgatgat g                                              21

<210> SEQ ID NO 42
<211> LENGTH: 22
<212> TYPE: DNA
<213> ORGANISM: Artificial Sequence
<220> FEATURE:
<223> OTHER INFORMATION: synthetic construct

<400> SEQUENCE: 42
cctgctgatg attcaggtga ta                                             22

<210> SEQ ID NO 43
<211> LENGTH: 22
<212> TYPE: DNA
<213> ORGANISM: Artificial Sequence
<220> FEATURE:
<223> OTHER INFORMATION: synthetic construct

<400> SEQUENCE: 43
cggtaatcct gggttctact ct                                             22

<210> SEQ ID NO 44
<211> LENGTH: 21
<212> TYPE: DNA
<213> ORGANISM: Artificial Sequence
<220> FEATURE:
<223> OTHER INFORMATION: synthetic construct

<400> SEQUENCE: 44
tgctcagctg gtcaacttta g                                              21

<210> SEQ ID NO 45
<211> LENGTH: 19
<212> TYPE: DNA
<213> ORGANISM: Artificial Sequence
<220> FEATURE:
<223> OTHER INFORMATION: synthetic construct

<400> SEQUENCE: 45
agcagggcag cattgttat                                                 19

<210> SEQ ID NO 46
<211> LENGTH: 22
<212> TYPE: DNA
<213> ORGANISM: Artificial Sequence
<220> FEATURE:
<223> OTHER INFORMATION: synthetic construct

<400> SEQUENCE: 46
gcaaatcagc atgaaggcat ag                                             22

<210> SEQ ID NO 47

```
<211> LENGTH: 23
<212> TYPE: DNA
<213> ORGANISM: Artificial Sequence
<220> FEATURE:
<223> OTHER INFORMATION: synthetic construct

<400> SEQUENCE: 47
gttcctgcat cagaggtaga tag                                            23

<210> SEQ ID NO 48
<211> LENGTH: 20
<212> TYPE: DNA
<213> ORGANISM: Artificial Sequence
<220> FEATURE:
<223> OTHER INFORMATION: synthetic construct

<400> SEQUENCE: 48
tacagcgatt ggcccttatt                                                20

<210> SEQ ID NO 49
<211> LENGTH: 21
<212> TYPE: DNA
<213> ORGANISM: Artificial Sequence
<220> FEATURE:
<223> OTHER INFORMATION: synthetic construct

<400> SEQUENCE: 49
cgtcattaac cgccaggaat a                                              21

<210> SEQ ID NO 50
<211> LENGTH: 21
<212> TYPE: DNA
<213> ORGANISM: Artificial Sequence
<220> FEATURE:
<223> OTHER INFORMATION: synthetic construct

<400> SEQUENCE: 50
gttcaccaaa gggtccaagt a                                              21

<210> SEQ ID NO 51
<211> LENGTH: 21
<212> TYPE: DNA
<213> ORGANISM: Artificial Sequence
<220> FEATURE:
<223> OTHER INFORMATION: synthetic construct

<400> SEQUENCE: 51
ctgatcgtgg gtaacgtaga g                                              21

<210> SEQ ID NO 52
<211> LENGTH: 21
<212> TYPE: DNA
<213> ORGANISM: Artificial Sequence
<220> FEATURE:
<223> OTHER INFORMATION: synthetic construct

<400> SEQUENCE: 52
gcagtgttcc tgtttgatga g                                              21

<210> SEQ ID NO 53
<211> LENGTH: 22
<212> TYPE: DNA
<213> ORGANISM: Artificial Sequence
<220> FEATURE:
<223> OTHER INFORMATION: synthetic construct
```

```
<400> SEQUENCE: 53
gcataagtcg cctcgtgata tg                                      22

<210> SEQ ID NO 54
<211> LENGTH: 22
<212> TYPE: DNA
<213> ORGANISM: Artificial Sequence
<220> FEATURE:
<223> OTHER INFORMATION: synthetic construct

<400> SEQUENCE: 54
gacggaatac gccgagttaa ag                                      22

<210> SEQ ID NO 55
<211> LENGTH: 21
<212> TYPE: DNA
<213> ORGANISM: Artificial Sequence
<220> FEATURE:
<223> OTHER INFORMATION: synthetic construct

<400> SEQUENCE: 55
cggtaccgtt gaagtgaaag a                                       21

<210> SEQ ID NO 56
<211> LENGTH: 22
<212> TYPE: DNA
<213> ORGANISM: Artificial Sequence
<220> FEATURE:
<223> OTHER INFORMATION: synthetic construct

<400> SEQUENCE: 56
acttcgtccc atttcaggtt ag                                      22
```

UNITED STATES PATENT AND TRADEMARK OFFICE
CERTIFICATE OF CORRECTION

| | |
|---|---|
| PATENT NO. | : 11,660,294 B2 |
| APPLICATION NO. | : 17/260140 |
| DATED | : May 30, 2023 |
| INVENTOR(S) | : Gireesh Rajashekara et al. |

It is certified that error appears in the above-identified patent and that said Letters Patent is hereby corrected as shown below:

In the Claims

In Column 86, Line 53 of Claim 1, delete "alkyl sulfonyl," and insert -- alkylsulfonyl, --
In Column 87, Line 24 of Claim 1, delete "alkyl sulfonyl," and insert -- alkylsulfonyl, --
In Column 87 Line 51 of Claim 6, after "subject" delete "poultry flock"
In Column 88, Lines 11-12 of Claim 15, delete "alkyl sulfonyl," and insert -- alkylsulfonyl, --

Signed and Sealed this
Twelfth Day of September, 2023

Katherine Kelly Vidal
*Director of the United States Patent and Trademark Office*